(12) United States Patent
Spiegelman et al.

(10) Patent No.: US 10,717,992 B2
(45) Date of Patent: Jul. 21, 2020

(54) COMPOSITIONS AND METHODS FOR REGULATING THERMOGENESIS AND MUSCLE INFLAMMATION USING METRNL AND METRN

(71) Applicant: Dana-Farber Cancer Institute, Inc., Boston, MA (US)

(72) Inventors: Bruce M. Spiegelman, Waban, MA (US); Rajesh R. Rao, Norwood, MA (US); Jonathan Z. Long, Cambridge, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 663 days.

(21) Appl. No.: 14/762,375

(22) PCT Filed: Jan. 21, 2014

(86) PCT No.: PCT/US2014/012243
§ 371 (c)(1),
(2) Date: Jul. 21, 2015

(87) PCT Pub. No.: WO2014/116556
PCT Pub. Date: Jul. 31, 2014

(65) Prior Publication Data
US 2015/0322460 A1 Nov. 12, 2015

Related U.S. Application Data

(60) Provisional application No. 61/756,856, filed on Jan. 25, 2013.

(51) Int. Cl.
| | | |
|---|---|---|
| *A61K 38/18* | (2006.01) | |
| *A61K 48/00* | (2006.01) | |
| *A61P 3/00* | (2006.01) | |
| *C07K 14/52* | (2006.01) | |
| *C12N 15/86* | (2006.01) | |
| *C12Q 1/6876* | (2018.01) | |
| *C07K 14/47* | (2006.01) | |

(52) U.S. Cl.
CPC .............. *C12N 15/86* (2013.01); *C07K 14/47* (2013.01); *C07K 14/52* (2013.01); *C12Q 1/6876* (2013.01); *C12N 2710/10042* (2013.01); *C12Q 2600/136* (2013.01); *C12Q 2600/158* (2013.01)

(58) Field of Classification Search
CPC ........ C07K 14/47; C07K 14/52; C12N 15/86; C12N 2710/10042; C12Q 1/6876; C12Q 2600/136; C12Q 2600/158
See application file for complete search history.

(56) References Cited

U.S. PATENT DOCUMENTS

| | | | |
|---|---|---|---|
| 5,981,277 A * | 11/1999 | Fransen ................. | C07K 14/52 435/252.3 |
| 8,334,264 B2 | 12/2012 | Jorgensen et al. | |
| 2003/0018165 A1* | 1/2003 | Fransen ................. | C07K 14/52 530/350 |
| 2011/0112035 A1* | 5/2011 | Jorgensen ............ | C07K 14/475 514/17.8 |

FOREIGN PATENT DOCUMENTS

WO WO-2008/136541 A1 11/2008
WO WO-2010/009732 A1 1/2010

OTHER PUBLICATIONS

Fumoto et al, Targeted Gene Delivery: Importance of Administration Routes, Chapter 1, Intech, 2013, pp. 3-31.*
Bruno et al, Basics and recent advances in peptide and protein drug delivery, TherDeliv. Nov. 2013 ; 4(11): 1443-1467.*
Hackman, D.G., Translating animal research into clinical benefit: Poor methodological standards in animal studies mean that positive results may not translate to the clinical domain, BMJ, 2007, pp. 163-168.*
Zuriga et al, Humans and Mice Display Opposing Patterns of "Browning" Gene Expression in Visceral and Subcutaneous White Adipose, Frontiers in Cardiovascular Medicine, 2017, p. 1-5.*
Pedersen, B.K., "Muscles and their myokines," J. Exp. Biol., 214:337-346 (2011).
Ramialison et al., "Rapid identification of PAX2/5/8 direct downstream targets in the otic vesicle by combinatorial use of bioinformatics tools," Genome Biology, 9:R145 (2008).
International Search Report dated Nov. 23, 2015 from PCT/US2014/012243.

* cited by examiner

Primary Examiner — Maria Marvich
(74) Attorney, Agent, or Firm — Foley Hoag LLP

(57) ABSTRACT

The invention provides compositions and methods for regulating thermogenesis and muscle inflammation through modulation of Metrnl and/or Metrn activity and/or expression. Also provided are methods for preventing or treating metabolic disorders and muscle inflammation disorders in a subject through modulation of Metrnl and/or Metrn activity and/or expression. Further provided are methods for identifying compounds that are capable of treating metabolic disorders and muscle inflammation disorders by modulating Metrnl and/or Metrn activity and/or expression.

9 Claims, 3 Drawing Sheets
Specification includes a Sequence Listing.

A

B

SEQUENCE LISTING

```
<160> NUMBER OF SEQ ID NOS: 30

<210> SEQ ID NO 1
<211> LENGTH: 936
<212> TYPE: DNA
<213> ORGANISM: Mus musculus

<400> SEQUENCE: 1
atgcggggtg cggtgtgggc ggcccggagg cgcgcggggc agcagtggcc tcggtccccg      60
ggccctgggc cgggtccgcc cccgccgcca ccgctgctgt tgctgctact actgctgctg     120
ggcggcgcga gcgctcagta ctccagcgac ctgtgcagct ggaaggggag tgggctcacc     180
cgagaggcac gcagcaagga ggtggagcag gtgtacctgc gctgctccgc aggctctgtg     240
gagtggatgt acccaactgg ggcgctcatt gttaacctac ggcccaacac cttctcacct     300
gcccagaact tgactgtgtg catcaagcct ttcagggact cctctggagc caatatttat     360
ttggaaaaaa ctggagaact aagactgttg gtgcgggaca tcagaggtga gcctggccaa     420
gtgcagtgct tcagcctgga gcagggaggc ttatttgtgg aggcgacacc ccaacaggac     480
atcagcagaa ggaccacagg cttccagtat gagctgatga gtgggcagag gggactggac     540
ctgcacgtgc tgtctgcccc ctgtcggcct tgcagtgaca ctgaggtcct ccttgccatc     600
tgtaccagtg actttgttgt ccgaggcttc attgaggacg tcacacatgt accagaacag     660
caagtgtcag tcatctacct gcgggtgaac aggcttcaca ggcagaagag cagggtcttc     720
cagccagctc ctgaggacag tggccactgg ctgggccatg tcacaacact gctgcagtgt     780
ggagtacgac cagggcatgg ggaattcctc ttcactggac atgtgcactt tggggaggca     840
caacttggat gtgccccacg ctttagtgac tttcaaagga tgtacaggaa agcagaagaa     900
atgggcataa accctgtga  aatcaatatg gagtga                               936

<210> SEQ ID NO 2
<211> LENGTH: 311
<212> TYPE: PRT
<213> ORGANISM: Mus musculus

<400> SEQUENCE: 2

Met Arg Gly Ala Val Trp Ala Ala Arg Arg Ala Gly Gln Gln Trp
1               5                   10                  15

Pro Arg Ser Pro Gly Pro Gly Pro Pro Pro Pro Pro Pro Leu
                20                  25                  30

Leu Leu Leu Leu Leu Leu Leu Leu Gly Gly Ala Ser Ala Gln Tyr Ser
```

```
               35                  40                  45
Ser Asp Leu Cys Ser Trp Lys Gly Ser Gly Leu Thr Arg Glu Ala Arg
 50                  55                  60

Ser Lys Glu Val Glu Gln Val Tyr Leu Arg Cys Ser Ala Gly Ser Val
 65                  70                  75                  80

Glu Trp Met Tyr Pro Thr Gly Ala Leu Ile Val Asn Leu Arg Pro Asn
                     85                  90                  95

Thr Phe Ser Pro Ala Gln Asn Leu Thr Val Cys Ile Lys Pro Phe Arg
                100                 105                 110

Asp Ser Ser Gly Ala Asn Ile Tyr Leu Glu Lys Thr Gly Glu Leu Arg
                115                 120                 125

Leu Leu Val Arg Asp Ile Arg Gly Glu Pro Gly Gln Val Gln Cys Phe
130                 135                 140

Ser Leu Glu Gln Gly Gly Leu Phe Val Glu Ala Thr Pro Gln Gln Asp
145                 150                 155                 160

Ile Ser Arg Arg Thr Thr Gly Phe Gln Tyr Glu Leu Met Ser Gly Gln
                165                 170                 175

Arg Gly Leu Asp Leu His Val Leu Ser Ala Pro Cys Arg Pro Cys Ser
                180                 185                 190

Asp Thr Glu Val Leu Leu Ala Ile Cys Thr Ser Asp Phe Val Val Arg
                195                 200                 205

Gly Phe Ile Glu Asp Val Thr His Val Pro Gln Gln Val Ser Val
210                 215                 220

Ile Tyr Leu Arg Val Asn Arg Leu His Arg Gln Lys Ser Arg Val Phe
225                 230                 235                 240

Gln Pro Ala Pro Glu Asp Ser Gly His Trp Leu Gly His Val Thr Thr
                245                 250                 255

Leu Leu Gln Cys Gly Val Arg Pro Gly His Gly Glu Phe Leu Phe Thr
                260                 265                 270

Gly His Val His Phe Gly Glu Ala Gln Leu Gly Cys Ala Pro Arg Phe
                275                 280                 285

Ser Asp Phe Gln Arg Met Tyr Arg Lys Ala Glu Glu Met Gly Ile Asn
290                 295                 300

Pro Cys Glu Ile Asn Met Glu
305                 310

<210> SEQ ID NO 3
<211> LENGTH: 936
<212> TYPE: DNA
<213> ORGANISM: Homo sapiens

<400> SEQUENCE: 3
atgcggggcg cggcgcgggc ggcctggggg cgcgcggggc agccgtggcc gcgaccccc       60 gccccgggcc cgccccgcc gccgctcccg ctgctgctcc tgctcctggc cgggctgctg    120
ggcggcgcgg gcgcgcagta ctccagcgac cggtgcagct ggaagggag cgggctgacg     180 cacgaggcac acaggaagga ggtggagcag gtgtatctgc gctgtgcggc gggtgccgtg    240
gagtggatgt acccaacagg tgctctcatc gttaacctgc ggcccaacac cttctcgcct    300
gcccggcacc tgaccgtgtg catcaggtcc ttcacggact cctcgggggc caatattat     360 ttggaaaaaa ctggagaact gagactgctg gtaccggacg gggacggcag gcccggccgg    420
gtgcagtgtt ttggcctgga gcagggcggc ctgttcgtgg aggccacgcc gcagcaggat    480
atcggccgga ggaccacagg cttccagtac gagctggtta ggaggcacag ggcgtcggac    540
```

```
ctgcacgagc tgtctgcgcc gtgccgtccc tgcagtgaca ccgaggtgct cctagccgtc    600
tgcaccagcg acttcgccgt tcgaggctcc atccagcaag ttacccacga gcctgagcgg    660
caggactcag ccatccacct gcgcgtgagc agactctatc ggcagaaaag cagggtcttc    720
gagccggtgc ccgagggtga cggccactgg caggggcgcg tcaggacgct gctggagtgt    780
ggcgtgcggc cggggcatgg cgacttcctc ttcactggcc acatgcactt cggggaggcg    840
cggctcggct gtgccccacg cttcaaggac ttccagagga tgtacaggga tgcccaggag    900
agggggctga acccttgtga ggttggcacg gactga                              936
```

<210> SEQ ID NO 4
<211> LENGTH: 311
<212> TYPE: PRT
<213> ORGANISM: Homo sapiens

<400> SEQUENCE: 4

```
Met Arg Gly Ala Ala Arg Ala Ala Trp Gly Arg Ala Gly Gln Pro Trp
1               5                   10                  15

Pro Arg Pro Pro Ala Pro Gly Pro Pro Pro Leu Pro Leu Leu
            20                  25                  30

Leu Leu Leu Leu Ala Gly Leu Leu Gly Gly Ala Gly Ala Gln Tyr Ser
        35                  40                  45

Ser Asp Arg Cys Ser Trp Lys Gly Ser Gly Leu Thr His Glu Ala His
    50                  55                  60

Arg Lys Glu Val Glu Gln Val Tyr Leu Arg Cys Ala Ala Gly Ala Val
65                  70                  75                  80

Glu Trp Met Tyr Pro Thr Gly Ala Leu Ile Val Asn Leu Arg Pro Asn
                85                  90                  95

Thr Phe Ser Pro Ala Arg His Leu Thr Val Cys Ile Arg Ser Phe Thr
            100                 105                 110

Asp Ser Ser Gly Ala Asn Ile Tyr Leu Glu Lys Thr Gly Glu Leu Arg
        115                 120                 125

Leu Leu Val Pro Asp Gly Asp Gly Arg Pro Gly Arg Val Gln Cys Phe
    130                 135                 140

Gly Leu Glu Gln Gly Gly Leu Phe Val Glu Ala Thr Pro Gln Gln Asp
145                 150                 155                 160

Ile Gly Arg Arg Thr Thr Gly Phe Gln Tyr Glu Leu Val Arg Arg His
                165                 170                 175

Arg Ala Ser Asp Leu His Glu Leu Ser Ala Pro Cys Arg Pro Cys Ser
            180                 185                 190

Asp Thr Glu Val Leu Leu Ala Val Cys Thr Ser Asp Phe Ala Val Arg
        195                 200                 205

Gly Ser Ile Gln Gln Val Thr His Glu Pro Glu Arg Gln Asp Ser Ala
    210                 215                 220

Ile His Leu Arg Val Ser Arg Leu Tyr Arg Gln Lys Ser Arg Val Phe
225                 230                 235                 240

Glu Pro Val Pro Glu Gly Asp Gly His Trp Gln Gly Arg Val Arg Thr
                245                 250                 255

Leu Leu Glu Cys Gly Val Arg Pro Gly His Gly Asp Phe Leu Phe Thr
            260                 265                 270

Gly His Met His Phe Gly Glu Ala Arg Leu Gly Cys Ala Pro Arg Phe
        275                 280                 285

Lys Asp Phe Gln Arg Met Tyr Arg Asp Ala Gln Glu Arg Gly Leu Asn
    290                 295                 300
```

Pro Cys Glu Val Gly Thr Asp
305                 310

<210> SEQ ID NO 5
<211> LENGTH: 861
<212> TYPE: DNA
<213> ORGANISM: Gallus gallus

<400> SEQUENCE: 5

```
atgccgctat ttacttcttt tctgaactcc tttggactgc tgacaattga tgcgtcctta      60
atccccgcga atccacttca aggcgagtcc gttcgtggct taactcacga gtctcacaag     120
aaggatgttg aacaggtcta cctccgctgt tccgaaggct ccatagagtg gatgtatccc     180
acgggagcgc tcatagtcaa cctgcgaccc aacacttcac ctgcctccta caaacatttg     240
actgtttgca taaagccctt caaggactct gcaggagcaa atatttattt ggaaaaaact     300
ggagaactca aactcttggt ccgagatgga gagcgcagcc ccagcaaggt gtactgcttt     360
ggctacgacc agggggggct gtttgtcgag gccaccccc agcaggacat tagcaggaag     420
atcacaggct ccagtacga actgatgagc agggggattg catctgattt gcacacagtt     480
tctgctccat gccgaccatg cagtgacaca gaggtcctct tggccgtctg cactagtgat     540
ttcgtgatca gaggctccat tcaagatgta acaaatgagg cagaagagca agaatccata     600
attcacgttg gcgtcaacaa actgtacagg cagaagagca agtctttca gctcacgggg      660
gagagtggga actggcgagg acaaataaag accctgctgg agtgtggggt gagaccagga     720
gatggagact tcctcttcac gggacgcatg cactttgggg aagccaggtt aggctgtgcc     780
cctcgattta aagacttcca aaggatgtac aaagaagcaa aagacaaagg gctaaatcca     840
tgtgaaattg gcccagattg a                                                861
```

<210> SEQ ID NO 6
<211> LENGTH: 286
<212> TYPE: PRT
<213> ORGANISM: Gallus gallus

<400> SEQUENCE: 6

Met Pro Leu Phe Thr Ser Phe Leu Asn Ser Phe Gly Leu Leu Thr Ile
1               5                   10                  15

Asp Ala Ser Leu Ile Pro Ala Asn Pro Leu Gln Gly Glu Ser Val Arg
            20                  25                  30

Gly Leu Thr His Glu Ser His Lys Lys Asp Val Glu Gln Val Tyr Leu
        35                  40                  45

Arg Cys Ser Glu Gly Ser Ile Glu Trp Met Tyr Pro Thr Gly Ala Leu
    50                  55                  60

Ile Val Asn Leu Arg Pro Asn Thr Ser Pro Ala Ser Tyr Lys His Leu
65                  70                  75                  80

Thr Val Cys Ile Lys Pro Phe Lys Asp Ser Ala Gly Ala Asn Ile Tyr
                85                  90                  95

Leu Glu Lys Thr Gly Glu Leu Lys Leu Leu Val Arg Asp Gly Glu Arg
            100                 105                 110

Ser Pro Ser Lys Val Tyr Cys Phe Gly Tyr Asp Gln Gly Gly Leu Phe
        115                 120                 125

Val Glu Ala Thr Pro Gln Gln Asp Ile Ser Arg Lys Ile Thr Gly Phe
    130                 135                 140

Gln Tyr Glu Leu Met Ser Arg Gly Ile Ala Ser Asp Leu His Thr Val
145                 150                 155                 160

```
Ser Ala Pro Cys Arg Pro Cys Ser Asp Thr Glu Val Leu Leu Ala Val
                165                 170                 175

Cys Thr Ser Asp Phe Val Ile Arg Gly Ser Ile Gln Asp Val Thr Asn
            180                 185                 190

Glu Ala Glu Gln Glu Ser Ile Ile His Val Gly Val Asn Lys Leu
        195                 200                 205

Tyr Arg Gln Lys Ser Lys Val Phe Gln Leu Thr Gly Glu Ser Gly Asn
        210                 215                 220

Trp Arg Gly Gln Ile Lys Thr Leu Leu Glu Cys Gly Val Arg Pro Gly
225                 230                 235                 240

Asp Gly Asp Phe Leu Phe Thr Gly Arg Met His Phe Gly Glu Ala Arg
                245                 250                 255

Leu Gly Cys Ala Pro Arg Phe Lys Asp Phe Gln Arg Met Tyr Lys Glu
            260                 265                 270

Ala Lys Asp Lys Gly Leu Asn Pro Cys Glu Ile Gly Pro Asp
            275                 280                 285

<210> SEQ ID NO 7
<211> LENGTH: 861
<212> TYPE: DNA
<213> ORGANISM: Danio rerio

<400> SEQUENCE: 7
atgctctcgc cgttcttggc gtatttgctg tcggttgtgc ttctgtgtcg gattgcgcgc      60
tcccagtact caagtgatca gtgcagctgg aggggcagtg gactgaccca tgagggacac     120
actcggggtg tggagcaggt gtatctccgc tgcgcccagg ggttcctgga gtggctgtac     180
cccactggcg caatcatcgt caacctgcgg ccaaacacgc tgtcacccgc agcgtctctt     240
ctctccgtct gcatcaaacc ctccaaggag tccagcggga cccacatcta ccttgacaga     300
ctgggaaaat gcgactgct cctcagcgaa ggggatcagg ccgagggtaa agtgcactgc      360
ttcaacatcc aggatgggc gctcttcatc gaagctgtgc ctcaaaggga catcagccga     420
aaaatcacag ccttccagta tgagctggtc aaccacagac caggagcaga tccacagtca     480
ttatctgctc cctgccaacc gtgtacagat gcagaggtcc tgctggccgt ctgcaccagt     540
gactttgtgg cgcggggag aattcttggt gtatccgagg aggatgaaca gacctcagtc     600
acagtgtcct taagtcacct atatagacag aagactcaag tgtttgtgtc agggggcggc     660
cgggctaaac gctggacagg cttttgtgaag atgtccaggc agtgcggggt taaaccaggg     720
gacggcgagt tcttttcac cgggactgtg cgattcggag aggcctggct cagctgcgct     780
ccacgctaca aggacttcct tagggtgtac caggacgcgc ggcagcaagg gaccaacccc     840
tgtcatttgg aaacagactg a                                               861

<210> SEQ ID NO 8
<211> LENGTH: 286
<212> TYPE: PRT
<213> ORGANISM: Danio rerio

<400> SEQUENCE: 8

Met Leu Ser Pro Phe Leu Ala Tyr Leu Leu Ser Val Val Leu Leu Cys
1               5                   10                  15

Arg Ile Ala Arg Ser Gln Tyr Ser Ser Asp Gln Cys Ser Trp Arg Gly
            20                  25                  30

Ser Gly Leu Thr His Glu Gly His Thr Arg Gly Val Glu Gln Val Tyr
        35                  40                  45
```

```
Leu Arg Cys Ala Gln Gly Phe Leu Glu Trp Leu Tyr Pro Thr Gly Ala
 50                  55                  60
Ile Ile Val Asn Leu Arg Pro Asn Thr Leu Ser Pro Ala Ala Ser Leu
 65                  70                  75                  80
Leu Ser Val Cys Ile Lys Pro Ser Lys Glu Ser Ser Gly Thr His Ile
                 85                  90                  95
Tyr Leu Asp Arg Leu Gly Lys Leu Arg Leu Leu Ser Glu Gly Asp
            100                 105                 110
Gln Ala Glu Gly Lys Val His Cys Phe Asn Ile Gln Asp Gly Ala Leu
            115                 120                 125
Phe Ile Glu Ala Val Pro Gln Arg Asp Ile Ser Arg Lys Ile Thr Ala
130                 135                 140
Phe Gln Tyr Glu Leu Val Asn His Arg Pro Gly Ala Asp Pro Gln Ser
145                 150                 155                 160
Leu Ser Ala Pro Cys Gln Pro Cys Thr Asp Ala Glu Val Leu Leu Ala
                165                 170                 175
Val Cys Thr Ser Asp Phe Val Ala Arg Gly Arg Ile Leu Gly Val Ser
            180                 185                 190
Glu Glu Asp Glu Gln Thr Ser Val Thr Val Ser Leu Ser His Leu Tyr
            195                 200                 205
Arg Gln Lys Thr Gln Val Phe Val Ser Gly Gly Arg Ala Lys Arg
210                 215                 220
Trp Thr Gly Phe Val Lys Met Ser Arg Gln Cys Gly Val Lys Pro Gly
225                 230                 235                 240
Asp Gly Glu Phe Leu Phe Thr Gly Thr Val Arg Phe Gly Glu Ala Trp
                245                 250                 255
Leu Ser Cys Ala Pro Arg Tyr Lys Asp Phe Leu Arg Val Tyr Gln Asp
            260                 265                 270
Ala Arg Gln Gln Gly Thr Asn Pro Cys His Leu Glu Thr Asp
            275                 280                 285

<210> SEQ ID NO 9
<211> LENGTH: 936
<212> TYPE: DNA
<213> ORGANISM: Rattus norvegicus

<400> SEQUENCE: 9
atgcggggtg tggtgtgggc ggcccggagg cgcgcggggc agcagtggcc tcggtccccg      60
ggccctgggc cgggtccgcc cccgccgcca ccgctgctgt tgctgctact gctgctgctg     120
ggcggcgcga gcgcgcagta ctccagcgac ctgtgcagct ggaaggggag tgggctcacc     180
cgggaggcac acagcaagga ggtggagcag gtgtacctgc gctgctcagc aggctctgtg     240
gaatggatgt acccaaccgg ggcgctcatt gttaacctac ggcccaacac cttctcacct     300
gcccagaact tgactgtgtg catcaagcct tcagggact cctctgggc caatatttat      360 ttggaaaaaa ctggagaact aagactgttg gtgcggatg tcagaggcga acctggccaa     420
gtgcagtgct tcagcctaga gcagggaggc ttatttgtgg aggccacacc ccagcaggac     480
atcagcagaa ggaccacagg cttccagtat gagctgatga gtgggcagag gggactggac     540
ctgcacgtgc tctctgcccc ctgtcgacct tgcagcgaca ctgaggtcct ccttgccatc     600
tgcaccagtg actttgttgt ccgaggcttc atcgaggatg tcacccatgt accagaacag     660
caagtgtcag tcattcacct acgggtgagc aggctccaca ggcagaagag cagggtcttc     720
cagccagctc ctgaggacag tggccactgg ctgggccatg tcacaacact gttgcagtgt     780
```

-continued

```
ggagtacgac cagggcatgg agaattcctc ttcactggac atgtgcactt tggggaggca    840
caacttggat gtgccccacg ctttagtgac tttcaaaaga tgtacaggaa agcagaagaa    900
aggggcataa accttgtga aataaatatg gagtga                               936
```

```
<210> SEQ ID NO 10
<211> LENGTH: 311
<212> TYPE: PRT
<213> ORGANISM: Rattus norvegicus

<400> SEQUENCE: 10
```

| | | | | | | | | | | | | | | |
|---|---|---|---|---|---|---|---|---|---|---|---|---|---|---|
| Met | Arg | Gly | Val | Val | Trp | Ala | Ala | Arg | Arg | Ala | Gly | Gln | Gln | Trp |
| 1 | | | | 5 | | | | | 10 | | | | | 15 |
| Pro | Arg | Ser | Pro | Gly | Pro | Gly | Pro | Pro | Pro | Pro | Pro | Pro | Pro | Leu |
| | | | 20 | | | | | 25 | | | | | 30 | |
| Leu | Leu | Leu | Leu | Leu | Leu | Leu | Leu | Gly | Gly | Ala | Ser | Ala | Gln | Tyr | Ser |
| | | | 35 | | | | | 40 | | | | | 45 | | |
| Ser | Asp | Leu | Cys | Ser | Trp | Lys | Gly | Ser | Gly | Leu | Thr | Arg | Glu | Ala | His |
| 50 | | | | | 55 | | | | | 60 | | | | | |
| Ser | Lys | Glu | Val | Glu | Gln | Val | Tyr | Leu | Arg | Cys | Ser | Ala | Gly | Ser | Val |
| 65 | | | | | 70 | | | | | 75 | | | | | 80 |
| Glu | Trp | Met | Tyr | Pro | Thr | Gly | Ala | Leu | Ile | Val | Asn | Leu | Arg | Pro | Asn |
| | | | | 85 | | | | | 90 | | | | | 95 | |
| Thr | Phe | Ser | Pro | Ala | Gln | Asn | Leu | Thr | Val | Cys | Ile | Lys | Pro | Phe | Arg |
| | | | 100 | | | | | 105 | | | | | 110 | | |
| Asp | Ser | Ser | Gly | Ala | Asn | Ile | Tyr | Leu | Glu | Lys | Thr | Gly | Glu | Leu | Arg |
| | | | 115 | | | | | 120 | | | | | 125 | | |
| Leu | Leu | Val | Arg | Asp | Val | Arg | Gly | Glu | Pro | Gly | Gln | Val | Gln | Cys | Phe |
| 130 | | | | | 135 | | | | | 140 | | | | | |
| Ser | Leu | Glu | Gln | Gly | Gly | Leu | Phe | Val | Glu | Ala | Thr | Pro | Gln | Gln | Asp |
| 145 | | | | | 150 | | | | | 155 | | | | | 160 |
| Ile | Ser | Arg | Arg | Thr | Thr | Gly | Phe | Gln | Tyr | Glu | Leu | Met | Ser | Gly | Gln |
| | | | | 165 | | | | | 170 | | | | | 175 | |
| Arg | Gly | Leu | Asp | Leu | His | Val | Leu | Ser | Ala | Pro | Cys | Arg | Pro | Cys | Ser |
| | | | 180 | | | | | 185 | | | | | 190 | | |
| Asp | Thr | Glu | Val | Leu | Leu | Ala | Ile | Cys | Thr | Ser | Asp | Phe | Val | Val | Arg |
| | | | 195 | | | | | 200 | | | | | 205 | | |
| Gly | Phe | Ile | Glu | Asp | Val | Thr | His | Val | Pro | Gln | Gln | Val | Ser | Val |
| 210 | | | | | 215 | | | | | 220 | | | | | |
| Ile | His | Leu | Arg | Val | Ser | Arg | Leu | His | Arg | Gln | Lys | Ser | Arg | Val | Phe |
| 225 | | | | | 230 | | | | | 235 | | | | | 240 |
| Gln | Pro | Ala | Pro | Glu | Asp | Ser | Gly | His | Trp | Leu | Gly | His | Val | Thr | Thr |
| | | | | 245 | | | | | 250 | | | | | 255 | |
| Leu | Leu | Gln | Cys | Gly | Val | Arg | Pro | Gly | His | Gly | Glu | Phe | Leu | Phe | Thr |
| | | | 260 | | | | | 265 | | | | | 270 | | |
| Gly | His | Val | His | Phe | Gly | Glu | Ala | Gln | Leu | Gly | Cys | Ala | Pro | Arg | Phe |
| | | | 275 | | | | | 280 | | | | | 285 | | |
| Ser | Asp | Phe | Gln | Lys | Met | Tyr | Arg | Lys | Ala | Glu | Glu | Arg | Gly | Ile | Asn |
| 290 | | | | | 295 | | | | | 300 | | | | | |
| Pro | Cys | Glu | Ile | Asn | Met | Glu |
| 305 | | | | 310 | | |

```
<210> SEQ ID NO 11
<211> LENGTH: 930
<212> TYPE: DNA
<213> ORGANISM: Bos taurus
```

<400> SEQUENCE: 11

```
atgcggggcg cgacgcgggc ggctgggggg cgcgcgggc agctgtggcc gaggcccccc      60
gccccgggcc ctggaccgcc gccgctgctg ctgctgctgg ccgtgctact gggcggcgcg     120
ggcgcgcagt actcgagcga cctgtgcagc tggaagggga gcgggctgac acacgaggcc    180
cacaggaagg aggtggagca agtttacctg cgctgctcgg cgggcaccgt cgagtggatg    240
tacccgaccg gggcgctcat cgtgaaccta cggcccaaca ccttctcgcc ctcccggaac    300
ctgactctgt gcatcaagcc ccttaggggc tcctcggggg ccaatattta tttggaaaag    360
actggagaac tgaaactgct ggtgagggat ggggacctcg ggcccggcca ggcgccgtgc    420
tttggcttcg agcaggggg cctgtttgtg gaggcgacgc cacagcaaga catcagcagg    480
aggaccacgg gcttccagta cgagctgacc agcaggcgca cggggccgga cctgcacgcc    540
ctgttggccc cgtgccgccc ttgcagccac acagaggttc tcttggccgt ctgcaccagc    600
gactttgtcg tccgaggctc catccagaaa gtcacccacg agccgagcg gcaggagtcg    660
gccatccacc tgaacgtgag ccggctctac cggcagaaga gcagggtgtt ccggccggcc    720
cctgagggcg agggcggcgg ctggcggggg gcgtctcca cgctactgga gtgcggcgtc    780
cggcctgggc acggcgagtt tctcttcacc ggccacatgc actttgggga ggcctggctt    840
ggctgcgccc cacgcttcaa ggatttccaa aggatgtaca gggacgctga ggagagggg    900
ctgaaccct gcgagatggg cacggagtga                                       930
```

<210> SEQ ID NO 12
<211> LENGTH: 309
<212> TYPE: PRT
<213> ORGANISM: Bos taurus

<400> SEQUENCE: 12

```
Met Arg Gly Ala Thr Arg Ala Ala Gly Gly Arg Ala Gly Gln Leu Trp
1               5                   10                  15

Pro Arg Pro Pro Ala Pro Gly Pro Gly Pro Pro Leu Leu Leu Leu Leu
            20                  25                  30

Leu Ala Val Leu Leu Gly Gly Ala Gly Ala Gln Tyr Ser Ser Asp Leu
        35                  40                  45

Cys Ser Trp Lys Gly Ser Gly Leu Thr His Glu Ala His Arg Lys Glu
    50                  55                  60

Val Glu Gln Val Tyr Leu Arg Cys Ser Ala Gly Thr Val Glu Trp Met
65                  70                  75                  80

Tyr Pro Thr Gly Ala Leu Ile Val Asn Leu Arg Pro Asn Thr Phe Ser
                85                  90                  95

Pro Ser Arg Asn Leu Thr Leu Cys Ile Lys Pro Leu Arg Gly Ser Ser
            100                 105                 110

Gly Ala Asn Ile Tyr Leu Glu Lys Thr Gly Glu Leu Lys Leu Leu Val
        115                 120                 125

Arg Asp Gly Asp Leu Gly Pro Gly Gln Ala Pro Cys Phe Gly Phe Glu
    130                 135                 140

Gln Gly Gly Leu Phe Val Glu Ala Thr Pro Gln Gln Asp Ile Ser Arg
145                 150                 155                 160

Arg Thr Thr Gly Phe Gln Tyr Glu Leu Thr Ser Arg Arg Thr Gly Pro
                165                 170                 175

Asp Leu His Ala Leu Leu Ala Pro Cys Arg Pro Cys Ser His Thr Glu
            180                 185                 190
```

```
Val Leu Leu Ala Val Cys Thr Ser Asp Phe Val Val Arg Gly Ser Ile
            195                 200                 205

Gln Lys Val Thr His Glu Pro Glu Arg Gln Glu Ser Ala Ile His Leu
    210                 215                 220

Asn Val Ser Arg Leu Tyr Arg Gln Lys Ser Arg Val Phe Arg Pro Ala
225                 230                 235                 240

Pro Glu Gly Glu Gly Gly Trp Arg Gly Arg Val Ser Thr Leu Leu
                245                 250                 255

Glu Cys Gly Val Arg Pro Gly His Gly Glu Phe Leu Phe Thr Gly His
                260                 265                 270

Met His Phe Gly Glu Ala Trp Leu Gly Cys Ala Pro Arg Phe Lys Asp
            275                 280                 285

Phe Gln Arg Met Tyr Arg Asp Ala Glu Glu Arg Gly Leu Asn Pro Cys
            290                 295                 300

Glu Met Gly Thr Glu
305

<210> SEQ ID NO 13
<211> LENGTH: 861
<212> TYPE: DNA
<213> ORGANISM: Xenopus laevis

<400> SEQUENCE: 13
atgttaagga ggggtctgct gagcttcttt atggtgattc ttatagacag agggacctca    60
cagctgtact ccagcgacat gtgcaattgg aaaggaagcg gcttgaccca tgagggccac   120
acgaaagatg ttgagcaagt ttacctccgc tgctccgaag ttctgttgga gtggctctac   180
ccaactggcg ccatggttat taacctgagg cctaacacct taacgtccgc ctacaaacac   240
ctaacagttt gcatcaaacc ttttaaagac tccaagggag ctaatattta ttccgaaaaa   300
actggagaac tcaaacttgt ggtgccagat ggagagaaca atccacacaa agtctattgc   360
tttggcctgg atcgaggggg tctgtatatt gaggccaccc cccagcaaga cattagtcgc   420
aaaatcactg gtttccagta tgaactgatc agccagagga ctctctcgga tttgcacaca   480
gtttctgatc cctgccgccc ctgcagtgat acagaagtcc tgctagctgt ctgtattagt   540
gatttcgttg tgaaagggac aatcagcgct gtgaccaatg atgaggagtt gcaggaatct   600
ctgatcaacg tcacggtgga taaactgtac aggcagaaga gtaaaatctt ccttcccaaa   660
gacaatgggg gatgggaggg aatgatacgg actcctctgg aatgtggggt taagacggga   720
atgggcagct tcttgttcac gggacgcatg cactttgggg agcccagatt gggctgcacg   780
cccgggtata aggactttaa aaggatatac ctagaagcga aaaagcaagg gttaaaccca   840
tgtgaaatca gcacggactg a                                            861

<210> SEQ ID NO 14
<211> LENGTH: 286
<212> TYPE: PRT
<213> ORGANISM: Xenopus laevis

<400> SEQUENCE: 14

Met Leu Arg Arg Gly Leu Leu Ser Phe Phe Met Val Ile Leu Ile Asp
1               5                   10                  15

Arg Gly Thr Ser Gln Leu Tyr Ser Ser Asp Met Cys Asn Trp Lys Gly
                20                  25                  30

Ser Gly Leu Thr His Glu Gly His Thr Lys Asp Val Glu Gln Val Tyr
            35                  40                  45
```

```
Leu Arg Cys Ser Glu Gly Ser Val Glu Trp Leu Tyr Pro Thr Gly Ala
 50                  55                  60
Met Val Ile Asn Leu Arg Pro Asn Thr Leu Thr Ser Ala Tyr Lys His
 65                  70                  75                  80
Leu Thr Val Cys Ile Lys Pro Phe Lys Asp Ser Lys Gly Ala Asn Ile
                 85                  90                  95
Tyr Ser Glu Lys Thr Gly Glu Leu Lys Leu Val Val Pro Asp Gly Glu
            100                 105                 110
Asn Asn Pro His Lys Val Tyr Cys Phe Gly Leu Asp Arg Gly Gly Leu
            115                 120                 125
Tyr Ile Glu Ala Thr Pro Gln Gln Asp Ile Ser Arg Lys Ile Thr Gly
130                 135                 140
Phe Gln Tyr Glu Leu Ile Ser Gln Arg Thr Leu Ser Asp Leu His Thr
145                 150                 155                 160
Val Ser Asp Pro Cys Arg Pro Cys Ser Asp Thr Glu Val Leu Leu Ala
                165                 170                 175
Val Cys Ile Ser Asp Phe Val Val Lys Gly Thr Ile Ser Ala Val Thr
            180                 185                 190
Asn Asp Glu Glu Leu Gln Glu Ser Leu Ile Asn Val Thr Val Asp Lys
            195                 200                 205
Leu Tyr Arg Gln Lys Ser Lys Ile Phe Leu Pro Lys Asp Asn Gly Gly
210                 215                 220
Trp Glu Gly Met Ile Arg Thr Pro Leu Glu Cys Gly Val Lys Thr Gly
225                 230                 235                 240
Met Gly Ser Phe Leu Phe Thr Gly Arg Met His Phe Gly Glu Pro Arg
                245                 250                 255
Leu Gly Cys Thr Pro Arg Tyr Lys Asp Phe Lys Arg Ile Tyr Leu Glu
            260                 265                 270
Ala Lys Lys Gln Gly Leu Asn Pro Cys Glu Ile Ser Thr Asp
            275                 280                 285

<210> SEQ ID NO 15
<211> LENGTH: 1044
<212> TYPE: DNA
<213> ORGANISM: Artificial Sequence
<220> FEATURE:
<223> OTHER INFORMATION: Mouse Metrnl cDNA Sequence With C-Terminal V5
      Epitope Tag

<400> SEQUENCE: 15
atgcggggtg cggtgtgggc ggcccggagg cgcgcggggc agcagtggcc tcggtccccg    60
ggccctgggc cgggtccgcc cccgccgcca ccgctgctgt tgctgctact actgctgctg   120
ggcggcgcga cgctcagta ctccagcgac ctgtgcagct ggaaggggag tgggctcacc    180
cgagaggcac gcagcaagga ggtggagcag gtgtacctgc gctgctccgc aggctctgtg   240
gagtggatgt acccaactgg ggcgctcatt gttaacctac ggcccaacac cttctcacct   300
gcccagaact tgactgtgtg catcaagcct ttcagggact cctctggagc caatatttat   360
ttggaaaaaa ctggagaact aagactgttg gtgcgggaca tcagaggtga gcctggccaa   420
gtgcagtgct tcagcctgga gcagggaggc ttatttgtgg aggcgacacc ccaacaggac   480
atcagcagaa ggaccacagg cttccagtat gagctgatga gtgggcagag gggactggac   540
ctgcacgtgc tgtctgcccc ctgtcggcct gcagtgaca ctgaggtcct ccttgccatc    600
tgtaccagtg actttgttgt ccgaggcttc attgaggacg tcacacatgt accagaacag   660
caagtgtcag tcatctacct gcgggtgaac aggcttcaca ggcagaagag cagggtcttc   720
```

```
cagccagctc ctgaggacag tggccactgg ctgggccatg tcacaacact gctgcagtgt    780
ggagtacgac cagggcatgg ggaattcctc ttcactggac atgtgcactt tggggaggca    840
caacttggat gtgccccacg ctttagtgac tttcaaagga tgtacaggaa agcagaagaa    900
atgggcataa accctgtgaa atcaatatg gaggacccag ctttcttgta caaagtggtt     960
gatctagagg gcccgcggtt cgaaggtaag cctatcccta accctctcct cggtctcgat   1020
tctacgcgta ccggttagta atga                                           1044
```

<210> SEQ ID NO 16
<211> LENGTH: 345
<212> TYPE: PRT
<213> ORGANISM: Artificial Sequence
<220> FEATURE:
<223> OTHER INFORMATION: Mouse Metrnl Amino Acid Sequence With
      C-Terminal V5 Epitope Tag

<400> SEQUENCE: 16

```
Met Arg Gly Ala Val Trp Ala Ala Arg Arg Ala Gly Gln Gln Trp
1               5                   10                  15

Pro Arg Ser Pro Gly Pro Gly Pro Gly Pro Pro Pro Pro Pro Leu
                20                  25                  30

Leu Leu Leu Leu Leu Leu Leu Leu Gly Gly Ala Ser Ala Gln Tyr Ser
            35                  40                  45

Ser Asp Leu Cys Ser Trp Lys Gly Ser Gly Leu Thr Arg Glu Ala Arg
50                  55                  60

Ser Lys Glu Val Glu Gln Val Tyr Leu Arg Cys Ser Ala Gly Ser Val
65                  70                  75                  80

Glu Trp Met Tyr Pro Thr Gly Ala Leu Ile Val Asn Leu Arg Pro Asn
                85                  90                  95

Thr Phe Ser Pro Ala Gln Asn Leu Thr Val Cys Ile Lys Pro Phe Arg
            100                 105                 110

Asp Ser Ser Gly Ala Asn Ile Tyr Leu Glu Lys Thr Gly Glu Leu Arg
        115                 120                 125

Leu Leu Val Arg Asp Ile Arg Gly Glu Pro Gly Gln Val Gln Cys Phe
130                 135                 140

Ser Leu Glu Gln Gly Gly Leu Phe Val Glu Ala Thr Pro Gln Asp
145                 150                 155                 160

Ile Ser Arg Arg Thr Thr Gly Phe Gln Tyr Glu Leu Met Ser Gly Gln
                165                 170                 175

Arg Gly Leu Asp Leu His Val Leu Ser Ala Pro Cys Arg Pro Cys Ser
            180                 185                 190

Asp Thr Glu Val Leu Leu Ala Ile Cys Thr Ser Asp Phe Val Val Arg
        195                 200                 205

Gly Phe Ile Glu Asp Val Thr His Val Pro Glu Gln Gln Val Ser Val
210                 215                 220

Ile Tyr Leu Arg Val Asn Arg Leu His Arg Gln Lys Ser Arg Val Phe
225                 230                 235                 240

Gln Pro Ala Pro Glu Asp Ser Gly His Trp Leu Gly His Val Thr Thr
                245                 250                 255

Leu Leu Gln Cys Gly Val Arg Pro Gly His Gly Glu Phe Leu Phe Thr
            260                 265                 270

Gly His Val His Phe Gly Glu Ala Gln Leu Gly Cys Ala Pro Arg Phe
        275                 280                 285

Ser Asp Phe Gln Arg Met Tyr Arg Lys Ala Glu Glu Met Gly Ile Asn
```

```
                290             295             300
Pro Cys Glu Ile Asn Met Glu Asp Pro Ala Phe Leu Tyr Lys Val Val
305                 310                 315                 320

Asp Leu Glu Gly Pro Arg Phe Glu Gly Lys Pro Ile Pro Asn Pro Leu
                325                 330                 335

Leu Gly Leu Asp Ser Thr Arg Thr Gly
            340                 345

<210> SEQ ID NO 17
<211> LENGTH: 876
<212> TYPE: DNA
<213> ORGANISM: Mus musculus

<400> SEQUENCE: 17
atgctggtag ccacgcttct ttgcgcgctc tgttgcggcc tcctggccgc gtccgctcac      60
gctggctact cggaagaccg ctgcagctgg aggggcagcg gtttgaccca ggagcctggc     120 agcgtgggc agctgaccct ggactgtact gagggcgcta tcgagtggct gtacccagct     180
ggggcgctgc gcctgaccct gggcggcccc gatccgggca cacggcccag catcgtctgt     240
ctgcgcccag agcggccctt cgctggtgcc caggtcttcg ctgaacgtat gaccggcaat     300
ctagagttgc tactggccga gggcccggac ctggctgggg gccgctgcat gcgctggggt     360
ccccgcgagc gccgagccct tttcctgcag gccacaccac accgcgacat cagccgcaga     420
gttgctgcct tccgttttga actgcacgag gaccaacgtg cagaaatgtc tccccaggct     480
caaggtcttg gtgtggatgg tgcctgcagg ccctgcagtg atgccgagct cctcctggct     540
gcatgcacca gtgattttgt gatccacggg accatccatg gggtcgccca tgacacagag     600
ctgcaagaat cagtcatcac tgtggtggtt gctcgtgtca tccgccagac actgccactg     660
ttcaaggaag ggagctcgga gggccaaggc cgggcctcca ttcgtacctt gctgcgctgt     720
ggtgtgcgtc ctggcccagg ctccttcctc ttcatgggct ggagccgatt ggcgaagct      780 tggctgggct gtgctccccg cttccaagag ttcagccgtg tctattcagc tgctctcacg     840
acccatctca acccatgtga gatggcactg gactga                               876

<210> SEQ ID NO 18
<211> LENGTH: 291
<212> TYPE: PRT
<213> ORGANISM: Mus musculus

<400> SEQUENCE: 18

Met Leu Val Ala Thr Leu Leu Cys Ala Leu Cys Cys Gly Leu Leu Ala
1               5                   10                  15

Ala Ser Ala His Ala Gly Tyr Ser Glu Asp Arg Cys Ser Trp Arg Gly
            20                  25                  30

Ser Gly Leu Thr Gln Glu Pro Gly Ser Val Gly Gln Leu Thr Leu Asp
        35                  40                  45

Cys Thr Glu Gly Ala Ile Glu Trp Leu Tyr Pro Ala Gly Ala Leu Arg
    50                  55                  60

Leu Thr Leu Gly Gly Pro Asp Pro Gly Thr Arg Pro Ser Ile Val Cys
65                  70                  75                  80

Leu Arg Pro Glu Arg Pro Phe Ala Gly Ala Gln Val Phe Ala Glu Arg
                85                  90                  95

Met Thr Gly Asn Leu Glu Leu Leu Leu Ala Glu Gly Pro Asp Leu Ala
            100                 105                 110

Gly Gly Arg Cys Met Arg Trp Gly Pro Arg Glu Arg Arg Ala Leu Phe
```

```
                    115                 120                 125
Leu Gln Ala Thr Pro His Arg Asp Ile Ser Arg Arg Val Ala Ala Phe
    130                 135                 140

Arg Phe Glu Leu His Glu Asp Gln Arg Ala Glu Met Ser Pro Gln Ala
145                 150                 155                 160

Gln Gly Leu Gly Val Asp Gly Ala Cys Arg Pro Cys Ser Asp Ala Glu
                165                 170                 175

Leu Leu Leu Ala Ala Cys Thr Ser Asp Phe Val Ile His Gly Thr Ile
                180                 185                 190

His Gly Val Ala His Asp Thr Glu Leu Gln Glu Ser Val Ile Thr Val
            195                 200                 205

Val Val Ala Arg Val Ile Arg Gln Thr Leu Pro Leu Phe Lys Glu Gly
    210                 215                 220

Ser Ser Glu Gly Gln Gly Arg Ala Ser Ile Arg Thr Leu Leu Arg Cys
225                 230                 235                 240

Gly Val Arg Pro Gly Pro Gly Ser Phe Leu Phe Met Gly Trp Ser Arg
                245                 250                 255

Phe Gly Glu Ala Trp Leu Gly Cys Ala Pro Arg Phe Gln Glu Phe Ser
                260                 265                 270

Arg Val Tyr Ser Ala Ala Leu Thr Thr His Leu Asn Pro Cys Glu Met
            275                 280                 285

Ala Leu Asp
    290

<210> SEQ ID NO 19
<211> LENGTH: 882
<212> TYPE: DNA
<213> ORGANISM: Homo sapiens

<400> SEQUENCE: 19 atgggggttcc cggccgcggc gctgctctgc gcgctgtgct gcggcctcct ggccccggct    60
gcccgcgccg gctactccga ggagcgctgc agctggaggg gcagcggcct cacccaggag   120
cccggcagcg tggggcagct ggccctggcc tgtgcggagg gcgcggttga gtggctgtac   180
ccggctgggg cgctgcgcct gaccctgggc ggccccgatc ccagagcgcg gcccggcatc   240
gcctgtctgc ggccggtgcg gcccttcgcg ggcgcccagg tcttcgcgga gcgcgcaggg   300
ggcgccctgg agctgctgct ggccgagggc ccgggcccgg caggggggccg ctgcgtgcgc   360 tggggtcccc gcgagcgccg ggccctcttc ctgcaggcca cgccgcacca ggacatcagc   420
cgccgcgtgg ccgccttccg ctttgagctg cgcgaggacg gcgccccga gctgcccccg   480 caggcccacg tctcggcgt agacggtgcc tgcaggccct gcagcgacgc tgagctgctc   540
ctggccgcat gcaccagcga cttcgtaatt cacgggatca tccatggggt cacccatgac   600
gtggagctgc aggagtctgt catcactgtg gtggccgccc gtgtcctccg ccagacaccg   660
ccgctgttcc aggcggggcg atccggggac caggggctga cctccattcg taccccactg   720
cgctgtggcg tccacccggg cccaggcacc ttcctcttca tgggctggag ccgctttggg   780
gaggcccggc tgggctgtgc ccacgattc aggagttcc gccgtgccta cgaggctgcc   840
cgtgctgccc acctccaccc ctgcgaggtg gcgctgcact ga                      882

<210> SEQ ID NO 20
<211> LENGTH: 293
<212> TYPE: PRT
<213> ORGANISM: Homo sapiens
```

<400> SEQUENCE: 20

```
Met Gly Phe Pro Ala Ala Ala Leu Leu Cys Ala Leu Cys Cys Gly Leu
1               5                   10                  15

Leu Ala Pro Ala Ala Arg Ala Gly Tyr Ser Glu Glu Arg Cys Ser Trp
            20                  25                  30

Arg Gly Ser Gly Leu Thr Gln Glu Pro Gly Ser Val Gly Gln Leu Ala
        35                  40                  45

Leu Ala Cys Ala Glu Gly Ala Val Glu Trp Leu Tyr Pro Ala Gly Ala
    50                  55                  60

Leu Arg Leu Thr Leu Gly Gly Pro Asp Pro Arg Ala Arg Pro Gly Ile
65                  70                  75                  80

Ala Cys Leu Arg Pro Val Arg Pro Phe Ala Gly Ala Gln Val Phe Ala
                85                  90                  95

Glu Arg Ala Gly Gly Ala Leu Glu Leu Leu Ala Glu Gly Pro Gly
            100                 105                 110

Pro Ala Gly Gly Arg Cys Val Arg Trp Gly Pro Arg Glu Arg Arg Ala
            115                 120                 125

Leu Phe Leu Gln Ala Thr Pro His Gln Asp Ile Ser Arg Arg Val Ala
    130                 135                 140

Ala Phe Arg Phe Glu Leu Arg Glu Asp Gly Arg Pro Glu Leu Pro Pro
145                 150                 155                 160

Gln Ala His Gly Leu Gly Val Asp Gly Ala Cys Arg Pro Cys Ser Asp
                165                 170                 175

Ala Glu Leu Leu Leu Ala Ala Cys Thr Ser Asp Phe Val Ile His Gly
            180                 185                 190

Ile Ile His Gly Val Thr His Asp Val Glu Leu Gln Glu Ser Val Ile
        195                 200                 205

Thr Val Val Ala Ala Arg Val Leu Arg Gln Thr Pro Pro Leu Phe Gln
    210                 215                 220

Ala Gly Arg Ser Gly Asp Gln Gly Leu Thr Ser Ile Arg Thr Pro Leu
225                 230                 235                 240

Arg Cys Gly Val His Pro Gly Pro Gly Thr Phe Leu Phe Met Gly Trp
                245                 250                 255

Ser Arg Phe Gly Glu Ala Arg Leu Gly Cys Ala Pro Arg Phe Gln Glu
            260                 265                 270

Phe Arg Arg Ala Tyr Glu Ala Ala Arg Ala Ala His Leu His Pro Cys
    275                 280                 285

Glu Val Ala Leu His
    290
```

<210> SEQ ID NO 21
<211> LENGTH: 882
<212> TYPE: DNA
<213> ORGANISM: Pan troglodytes

<400> SEQUENCE: 21

| | | |
|---|---|---|
| atgggggttcc cggccgcggc gctgctctgc gcgctgtgct gcggcctcct ggccccggcc | 60 |
| gcccgcgccg gctactccga ggagcgctgc agctggaggg gcagcggcct cacccaggag | 120 |
| cctggcagcg tggggcagct ggccctggcc tgtgcggagg gcgcggttga gtggctgtac | 180 |
| cccgctgggg cgctgcgcct gaccctgggc ggccccgatc ccagagcgcg gcccggcatc | 240 |
| gcctgtctgc ggccggtgcg gcccttcgcg ggcgcccagg tcttcgcgga gcgcgcaggg | 300 |
| ggcgccctgg agctgctgct ggccgagggc ccgggcccgg caggggggccg ctgcgtgcgc | 360 |

-continued

```
tggggtcccc gcgagcgccg ggccctcttc ctgcaggcca cgccgcaccg ggacatcagc      420
cgccgcgtgg ccgccttccg ctttgagctg cgcgaggacg ggcgcccga gctgcccccg       480 caggcccacg gtctcggcgt agacggtgcc tgcaggccct gcagcgatgc tgagctgctc      540
ctggccgcat gcaccagcga cttcgtaatt cacgggatca tccatggggt cgcccatgac      600
gtggagctgc aggaatctgt catcaccgtg gtggccgccc gtgtcctccg ccagacaccg      660
ccgctgttcc aggcggggcg atccggggac caggggctga cctccattcg tactccactg      720
cgctgtggcg tccgcccggg cccaggcacc ttcctcttca tgggctggag ccgcttcggg      780
gaggcctggc tgggctgtgc cccacgattc caggagttcc gccgtgccta cgaggctgcc      840
cgtgctgccc acctccaccc ctgcgaggtg gcgctgcact ga                         882
```

<210> SEQ ID NO 22
<211> LENGTH: 293
<212> TYPE: PRT
<213> ORGANISM: Pan troglodytes

<400> SEQUENCE: 22

```
Met Gly Phe Pro Ala Ala Ala Leu Leu Cys Ala Leu Cys Cys Gly Leu
1               5                   10                  15

Leu Ala Pro Ala Ala Arg Ala Gly Tyr Ser Glu Glu Arg Cys Ser Trp
                20                  25                  30

Arg Gly Ser Gly Leu Thr Gln Glu Pro Gly Ser Val Gly Gln Leu Ala
            35                  40                  45

Leu Ala Cys Ala Glu Gly Ala Val Glu Trp Leu Tyr Pro Ala Gly Ala
        50                  55                  60

Leu Arg Leu Thr Leu Gly Gly Pro Asp Pro Arg Ala Arg Pro Gly Ile
65                  70                  75                  80

Ala Cys Leu Arg Pro Val Arg Pro Phe Ala Gly Ala Gln Val Phe Ala
                85                  90                  95

Glu Arg Ala Gly Gly Ala Leu Glu Leu Leu Ala Glu Gly Pro Gly
            100                 105                 110

Pro Ala Gly Gly Arg Cys Val Arg Trp Gly Pro Arg Glu Arg Arg Ala
        115                 120                 125

Leu Phe Leu Gln Ala Thr Pro His Arg Asp Ile Ser Arg Arg Val Ala
130                 135                 140

Ala Phe Arg Phe Glu Leu Arg Glu Asp Gly Arg Pro Glu Leu Pro Pro
145                 150                 155                 160

Gln Ala His Gly Leu Gly Val Asp Gly Ala Cys Arg Pro Cys Ser Asp
                165                 170                 175

Ala Glu Leu Leu Leu Ala Ala Cys Thr Ser Asp Phe Val Ile His Gly
            180                 185                 190

Ile Ile His Gly Val Ala His Asp Val Glu Leu Gln Glu Ser Val Ile
        195                 200                 205

Thr Val Val Ala Ala Arg Val Leu Arg Gln Thr Pro Pro Leu Phe Gln
    210                 215                 220

Ala Gly Arg Ser Gly Asp Gln Gly Leu Thr Ser Ile Arg Thr Pro Leu
225                 230                 235                 240

Arg Cys Gly Val Arg Pro Gly Pro Gly Thr Phe Leu Phe Met Gly Trp
                245                 250                 255

Ser Arg Phe Gly Glu Ala Trp Leu Gly Cys Ala Pro Arg Phe Gln Glu
            260                 265                 270

Phe Arg Arg Ala Tyr Glu Ala Ala Arg Ala Ala His Leu His Pro Cys
        275                 280                 285
```

Glu Val Ala Leu His
        290

<210> SEQ ID NO 23
<211> LENGTH: 876
<212> TYPE: DNA
<213> ORGANISM: Bos taurus

<400> SEQUENCE: 23

| | | | | | |
|---|---|---|---|---|---|
| atgccgacct | ctgcgctgct | ctgcacactt | tgcttctgcc | tcttggccgc | ggccgctcgc | 60 |
| gccggctact | cggaggaccg | ctgcagctgg | aggggcagcg | gcctgaccca | ggagcccggc | 120 |
| agcgtgggac | agctcgccct | ggcctgtgcg | gacggcaaga | tcgagtggct | gtacccggcc | 180 |
| ggggcgctgc | gcctcaccct | gggcggctct | gagcccagcg | cgcagcccgg | catcgtctgc | 240 |
| ctgcggccga | cgcggcccct | cgcaggcgcc | caagtcttcg | tggagcggac | gggcggcggg | 300 |
| ctagagttgc | tgctggccga | gggccagggc | ccggccgggg | cccggtgcgc | gcgctggggt | 360 |
| cctcgcgagc | gccgggccct | cttcctgcag | gccacccccgc | atcccgacct | cagccgccgc | 420 |
| ttggcctcct | tccgcttcca | gctgcgggag | gacgggcgtc | cggagctgcc | cccgcaggcc | 480 |
| cgcagccttg | gagcggatgc | tgcctgcaga | ccctgcagtg | atgccgagct | cctcctggcc | 540 |
| gtgtgcacca | gtgactttgt | gatctacgga | accatcctcg | gagttgccca | caacgcagag | 600 |
| ctacaggagt | ctgtcatcac | cgtggcagct | gcacgtgtcc | tccgccagac | gctgccggtt | 660 |
| ttctgggtgg | ggggccctgg | gggccagggg | caggcctcca | ttcgcacccc | actgcactgt | 720 |
| ggcgtgcgcc | ctggccctgg | caccttcctc | ttcatgggct | ggaaccgctt | tggtgaggcc | 780 |
| tggctgggct | gtgctccccg | cctccaggaa | ttcagccgtg | cctacgcggc | tgcccacgct | 840 |
| gaccacctgc | accctgcgca | ggtggtgctg | gactga | | | 876 |

<210> SEQ ID NO 24
<211> LENGTH: 291
<212> TYPE: PRT
<213> ORGANISM: Bos taurus

<400> SEQUENCE: 24

Met Pro Thr Ser Ala Leu Leu Cys Thr Leu Cys Phe Cys Leu Leu Ala
1               5                   10                  15

Ala Ala Arg Ala Gly Tyr Ser Glu Asp Arg Cys Ser Trp Arg Gly
            20                  25                  30

Ser Gly Leu Thr Gln Glu Pro Gly Ser Val Gly Gln Leu Ala Leu Ala
            35                  40                  45

Cys Ala Asp Gly Lys Ile Glu Trp Leu Tyr Pro Ala Gly Ala Leu Arg
        50                  55                  60

Leu Thr Leu Gly Gly Ser Glu Pro Ser Ala Gln Pro Gly Ile Val Cys
65                  70                  75                  80

Leu Arg Pro Thr Arg Pro Phe Ala Gly Ala Gln Val Phe Val Glu Arg
                85                  90                  95

Thr Gly Gly Gly Leu Glu Leu Leu Ala Glu Gly Gln Gly Pro Ala
            100                 105                 110

Gly Ala Arg Cys Ala Arg Trp Gly Pro Arg Glu Arg Arg Ala Leu Phe
        115                 120                 125

Leu Gln Ala Thr Pro His Pro Asp Leu Ser Arg Leu Ala Ser Phe
    130                 135                 140

Arg Phe Gln Leu Arg Glu Asp Gly Arg Pro Glu Leu Pro Pro Gln Ala
145                 150                 155                 160

Arg Ser Leu Gly Ala Asp Ala Ala Cys Arg Pro Cys Ser Asp Ala Glu
        165                 170                 175

Leu Leu Leu Ala Val Cys Thr Ser Asp Phe Val Ile Tyr Gly Thr Ile
        180                 185                 190

Leu Gly Val Ala His Asn Ala Glu Leu Gln Glu Ser Val Ile Thr Val
        195                 200                 205

Ala Ala Ala Arg Val Leu Arg Gln Thr Leu Pro Val Phe Trp Val Gly
    210                 215                 220

Gly Pro Gly Gly Gln Gly Gln Ala Ser Ile Arg Thr Pro Leu His Cys
225                 230                 235                 240

Gly Val Arg Pro Gly Pro Gly Thr Phe Leu Phe Met Gly Trp Asn Arg
                245                 250                 255

Phe Gly Glu Ala Trp Leu Gly Cys Ala Pro Arg Leu Gln Glu Phe Ser
            260                 265                 270

Arg Ala Tyr Ala Ala Ala His Ala Asp His Leu His Pro Cys Glu Val
        275                 280                 285

Val Leu Asp
    290

<210> SEQ ID NO 25
<211> LENGTH: 876
<212> TYPE: DNA
<213> ORGANISM: Rattus norvegicus

<400> SEQUENCE: 25

```
atgctggtag cggcgcttct ctgcgcgctg tgctgcggcc tcttggctgc gtccgctcga      60
gctggctact ccgaggaccg ctgcagctgg aggggcagcg gtttgaccca ggaacctggc     120
agcgtggggc agctgaccct ggattgtact gagggtgcta tcgagtggct gtatccagct     180
ggggcgctgc gcctgactct aggcggctct gatccgggca cgcggcccag catcgtctgt     240
ctgcgcccaa cacggccctt cgctggtgcc caggtcttcg ctgaacggat ggccggcaac     300
ctagagttgc tactggccga aggccaaggc ctggctgggg ccgctgcat cgctggggt      360
cctcgcgagc gccgagccct tttcctgcag gccacgccac accgggacat cagccgcaga     420
gttgctgcct tccaatttga actgcacgag gaccaacgtg cagaaatgtc tccccaggcc     480
caaggttttg tgtggatgg tgcctgcagg ccctgcagtg atgccgagct ccttctgact     540
gcatgcacca gtgactttgt gatccatggg accatccatg gggtcgtcca tgacatggag     600
ctgcaagaat cagtcatcac tgtggtggcc actcgtgtca tccgccagac actgccactg     660
ttccaggaag ggagctcgga gggccgggc caggcctccg ttcgtacctt gttgcgctgt      720
ggtgtgcgtc ctggcccagg ctccttcctc ttcatgggct ggagccgatt ggcgaagct      780
tggctgggct gcgctccccg cttccaagag ttcagccgtg tctattcagc tgctctcgcg     840
gcccacctca acccatgtga ggtggcactg gactga                              876
```

<210> SEQ ID NO 26
<211> LENGTH: 291
<212> TYPE: PRT
<213> ORGANISM: Rattus norvegicus

<400> SEQUENCE: 26

Met Leu Val Ala Ala Leu Leu Cys Ala Leu Cys Cys Gly Leu Leu Ala
1               5                   10                  15

Ala Ser Ala Arg Ala Gly Tyr Ser Glu Asp Arg Cys Ser Trp Arg Gly
            20                  25                  30

Ser Gly Leu Thr Gln Glu Pro Gly Ser Val Gly Gln Leu Thr Leu Asp
     35                  40                  45

Cys Thr Glu Gly Ala Ile Glu Trp Leu Tyr Pro Ala Gly Ala Leu Arg
 50                  55                  60

Leu Thr Leu Gly Gly Ser Asp Pro Gly Thr Arg Pro Ser Ile Val Cys
 65                  70                  75                  80

Leu Arg Pro Thr Arg Pro Phe Ala Gly Ala Gln Val Phe Ala Glu Arg
                 85                  90                  95

Met Ala Gly Asn Leu Glu Leu Leu Ala Glu Gly Gln Gly Leu Ala
             100                 105                 110

Gly Gly Arg Cys Met Arg Trp Gly Pro Arg Glu Arg Ala Leu Phe
         115                 120                 125

Leu Gln Ala Thr Pro His Arg Asp Ile Ser Arg Val Ala Ala Phe
     130                 135                 140

Gln Phe Glu Leu His Glu Asp Gln Arg Ala Glu Met Ser Pro Gln Ala
145                 150                 155                 160

Gln Gly Phe Gly Val Asp Gly Ala Cys Arg Pro Cys Ser Asp Ala Glu
                165                 170                 175

Leu Leu Leu Thr Ala Cys Thr Ser Asp Phe Val Ile His Gly Thr Ile
            180                 185                 190

His Gly Val Val His Asp Met Glu Leu Gln Glu Ser Val Ile Thr Val
        195                 200                 205

Val Ala Thr Arg Val Ile Arg Gln Thr Leu Pro Leu Phe Gln Glu Gly
    210                 215                 220

Ser Ser Glu Gly Arg Gly Gln Ala Ser Val Arg Thr Leu Leu Arg Cys
225                 230                 235                 240

Gly Val Arg Pro Gly Pro Gly Ser Phe Leu Phe Met Gly Trp Ser Arg
                245                 250                 255

Phe Gly Glu Ala Trp Leu Gly Cys Ala Pro Arg Phe Gln Glu Phe Ser
            260                 265                 270

Arg Val Tyr Ser Ala Ala Leu Ala Ala His Leu Asn Pro Cys Glu Val
        275                 280                 285

Ala Leu Asp
    290

<210> SEQ ID NO 27
<211> LENGTH: 876
<212> TYPE: DNA
<213> ORGANISM: Gallus gallus

<400> SEQUENCE: 27
atgcgggctc tgtgggcgct gtgcctcgcc gggctggccg ctgccctcgg cagcttctcg      60
gcggatcagt gcagctggag ggggagcggc ttgtcgcagg aggcgggcag cgtggagcag     120
ctcaccctgc gctgcgccga gggctccctg gagtggctgt accccacggg agccctccgc     180
ctccgcttgg ccccccgcct gccccccgcc accaccgccg atggccgcga ccccgacac      240 gtcaccgcct gccttcagcc cgccggcacc ttccgggggg ctcagctcta cctggagcgg     300
gatggggagc tggagctgct gctgcccgag gcggaggcgg cccgcgggcc cgtgtgagg      360 tgtttcagct ggccacccca tgagcaggtg gccctgttcc tgcaggccac cccgcagcgc     420
gacatcagcc gccgcatcgc tgccttccgc tatgagctgc gggggactg gctcgcccgc      480 cctgcactgc ctgccgaagg ggtgtgccgg ccgtgcaacg acaccgagct cctgatggcc     540
atttgcacta gtgactttgt ggtccgcggt accatccaca gcgtctccaa cgacgcagag     600

```
ctgcaggaat ccgtcatcgg ggtgagtgcc gtccgcatcc accgccagaa attcccctc        660 ttccaaaccg gggggcggcc ggggagggcg gtgggcagca tccgcacccc tctgcgctgc        720
ggtgtgcggc cgggccccgg caccttcctc ttcacggggt ggctgcactt tggcgaggca        780
tggctcagct gcgctccccg ctacaaggac ttccagcgca tctacagggg cgccggcgc         840 aggaggcaga acccctgcga gttccccgtg gactga                                  876
```

```
<210> SEQ ID NO 28
<211> LENGTH: 291
<212> TYPE: PRT
<213> ORGANISM: Gallus gallus

<400> SEQUENCE: 28
```

Met Arg Ala Leu Trp Ala Leu Cys Leu Ala Gly Leu Ala Ala Leu
1               5                   10                  15

Gly Ser Phe Ser Ala Asp Gln Cys Ser Trp Arg Gly Ser Gly Leu Ser
            20                  25                  30

Gln Glu Ala Gly Ser Val Glu Gln Leu Thr Leu Arg Cys Ala Glu Gly
        35                  40                  45

Ser Leu Glu Trp Leu Tyr Pro Thr Gly Ala Leu Arg Leu Arg Leu Ala
    50                  55                  60

Pro Arg Leu Pro Pro Ala Thr Thr Ala Asp Gly Arg Asp Pro Arg His
65                  70                  75                  80

Val Thr Ala Cys Leu Gln Pro Ala Gly Thr Phe Arg Gly Ala Gln Leu
                85                  90                  95

Tyr Leu Glu Arg Asp Gly Glu Leu Leu Leu Leu Pro Glu Ala Glu
            100                 105                 110

Ala Ala Pro Arg Pro Arg Val Arg Cys Phe Ser Trp Pro Pro His Glu
        115                 120                 125

Gln Val Ala Leu Phe Leu Gln Ala Thr Pro Gln Arg Asp Ile Ser Arg
130                 135                 140

Arg Ile Ala Ala Phe Arg Tyr Glu Leu Arg Gly Asp Trp Leu Ala Arg
145                 150                 155                 160

Pro Ala Leu Pro Ala Glu Gly Val Cys Arg Pro Cys Asn Asp Thr Glu
                165                 170                 175

Leu Leu Met Ala Ile Cys Thr Ser Asp Phe Val Val Arg Gly Thr Ile
            180                 185                 190

His Ser Val Ser Asn Asp Ala Glu Leu Gln Glu Ser Val Ile Gly Val
        195                 200                 205

Ser Ala Val Arg Ile His Arg Gln Lys Phe Pro Leu Phe Gln Thr Gly
    210                 215                 220

Gly Arg Pro Gly Arg Ala Val Gly Ser Ile Arg Thr Pro Leu Arg Cys
225                 230                 235                 240

Gly Val Arg Pro Gly Pro Gly Thr Phe Leu Phe Thr Gly Trp Leu His
                245                 250                 255

Phe Gly Glu Ala Trp Leu Ser Cys Ala Pro Arg Tyr Lys Asp Phe Gln
            260                 265                 270

Arg Ile Tyr Glu Gly Ala Arg Arg Arg Gln Asn Pro Cys Glu Phe
        275                 280                 285

Pro Val Asp
290

```
<210> SEQ ID NO 29
<211> LENGTH: 912
```

```
<212> TYPE: DNA
<213> ORGANISM: Danio rerio

<400> SEQUENCE: 29
atggagattt ggggatttag gagtgttgcg ctatggattt cattcctgac gggttggtcg     60
atggccagtt actcagaaga tcagtgcagc tggagaggaa gtggactttc tcaggcggtg    120
aagaatgtgg agcaggtttg gttgaggtgt gcggagggct cggtggagtg gttgtatcct    180
gctggagctt tgcgtctcac cctgtcgccc gtctgccat ggagtgccat ggggccgggc    240
gagtccagca ggagcccggt gtcagtctgc gtcaagcctg atccacactg gggtggggct    300
cagctgtatc tggagcgcga tggagtcctg gagcttctgg tgggagatga gacctccacc    360
acacccggcc cagcccatgt acgctgcttt agtgccctgc ccggagaacg acctgcactg    420
ttcctgcagg ccacaccgca ccgggatatc agcagacgca tcgctgcctt ccgctacgag    480
ctgagagggg attggacggc gcagccagca gtcaacacag atccagtcag cagcgaagga    540
gcctgcagac cctgcaataa cactgagatc ctgatggccg tctgcactag tgactttgtg    600
gttcgaggaa acatccgctc agtgggaaca gactcgaatc taaaagcagc cgtgatcaaa    660
gtgagtgcga cgcgggttta ccggcagaag tttgcgttgt ccctgaatc tgggcgtctg    720
acgcgtttag gcgagatccg taccctcta caatgtggcg ttcgtcctgg tgcaggcagt    780
ttcctcttca ccggacgcgt gcatttcggg gaggcctggc ttggctgcgc tccaagatat    840
aaagactttc tgaaggcgta cgaacaggcc aaacaatcct tgatgatccc ctgcactctt    900
gtcaatgact ga                                                        912

<210> SEQ ID NO 30
<211> LENGTH: 303
<212> TYPE: PRT
<213> ORGANISM: Danio rerio

<400> SEQUENCE: 30

Met Glu Ile Trp Gly Phe Arg Ser Val Ala Leu Trp Ile Ser Phe Leu
1               5                   10                  15

Thr Gly Trp Ser Met Ala Ser Tyr Ser Glu Asp Gln Cys Ser Trp Arg
            20                  25                  30

Gly Ser Gly Leu Ser Gln Ala Val Lys Asn Val Glu Gln Val Trp Leu
        35                  40                  45

Arg Cys Ala Glu Gly Ser Val Glu Trp Leu Tyr Pro Ala Gly Ala Leu
    50                  55                  60

Arg Leu Thr Leu Ser Pro Arg Leu Pro Trp Ser Ala Met Gly Pro Gly
65                  70                  75                  80

Glu Ser Ser Arg Ser Pro Val Ser Val Cys Val Lys Pro Asp Pro His
                85                  90                  95

Trp Gly Gly Ala Gln Leu Tyr Leu Glu Arg Asp Gly Val Leu Glu Leu
            100                 105                 110

Leu Val Gly Asp Glu Thr Ser Thr Thr Pro Gly Pro Ala His Val Arg
        115                 120                 125

Cys Phe Ser Ala Leu Pro Gly Glu Arg Pro Ala Leu Phe Leu Gln Ala
    130                 135                 140

Thr Pro His Arg Asp Ile Ser Arg Arg Ile Ala Ala Phe Arg Tyr Glu
145                 150                 155                 160

Leu Arg Gly Asp Trp Thr Ala Gln Pro Ala Val Asn Thr Asp Pro Val
                165                 170                 175

Ser Ser Glu Gly Ala Cys Arg Pro Cys Asn Asn Thr Glu Ile Leu Met
```

-continued

```
            180                 185                 190
Ala Val Cys Thr Ser Asp Phe Val Val Arg Gly Asn Ile Arg Ser Val
        195                 200                 205

Gly Thr Asp Ser Asn Leu Lys Ala Ala Val Ile Lys Val Ser Ala Thr
        210                 215                 220

Arg Val Tyr Arg Gln Lys Phe Ala Leu Phe Pro Glu Ser Gly Arg Leu
225                 230                 235                 240

Thr Arg Leu Gly Glu Ile Arg Thr Pro Leu Gln Cys Gly Val Arg Pro
                245                 250                 255

Gly Ala Gly Ser Phe Leu Phe Thr Gly Arg Val His Phe Gly Glu Ala
                260                 265                 270

Trp Leu Gly Cys Ala Pro Arg Tyr Lys Asp Phe Leu Lys Ala Tyr Glu
        275                 280                 285

Gln Ala Lys Gln Ser Leu Met Ile Pro Cys Thr Leu Val Asn Asp
        290                 295                 300
```

COMPOSITIONS AND METHODS FOR REGULATING THERMOGENESIS AND MUSCLE INFLAMMATION USING METRNL AND METRN

CROSS-REFERENCE TO RELATED APPLICATIONS

This application claims the benefit of U.S. Provisional Application No. 61/756,856, filed on Jan. 25, 2013; the entire content of said application is incorporated herein in its entirety by this reference.

STATEMENT OF RIGHTS

This invention was made with government support under Grant number DK061562 awarded by the National Institutes of Health. The government has certain rights in the invention.

BACKGROUND OF THE INVENTION

Muscle-secreted hormones (e.g., myokines) have been hypothesized to exist and exert autocrine, paracrine, or endocrine effects since skeletal muscle comprises the largest organ in the human body and exercise involving skeletal muscle contraction is known to have major metabolic and immunological effects (Pedersen (2010) *J. Exp. Biol.* 214: 337-346). Despite decades of research focused on identifying myokines that can mimic the benefits of skeletal muscle-induced metabolic changes in organs such as adipose tissue and the immune system, very few such myokines have been discovered (Boström et al. (2012) *Nature* 481:463-468; Pedersen and Febbraio (2008) *Physiol. Rev.* 88:1379-1406). Exacerbating the paucity of known myokines having such beneficial therapeutic effects, the clinical need for such agents has never been greater.

For example, metabolic disorders comprise a collection of health disorders that increase the risk of morbidity and loss of quality of life afflicting greater than 50 million people in the United States. Such metabolic disorders, including diabetes, obesity, including central obesity (disproportionate fat tissue in and around the abdomen), atherogenic dyslipidemia (including a family of blood fat disorders, e.g., high triglycerides, low HDL cholesterol, and high LDL cholesterol that can foster plaque buildups in the vascular system, including artery walls), high blood pressure (130/85 mmHg or higher), insulin resistance or glucose intolerance (the inability to properly use insulin or blood sugar), a chronic prothrombotic state (e.g., characterized by high fibrinogen or plasminogen activator inhibitor-1 levels in the blood), and a chronic proinflammatory state (e.g., characterized by higher than normal levels of high-sensitivity C-reactive protein in the blood), are increasing in prevalence among the U.S. population.

Similarly, many myopathies are associated with inflammation of muscle (e.g., skeletal muscle) and are relatively prevalent among the general U.S. population. For example, Duchenne muscular dystrophy (DMD) affects 1 in 3,500 male births. Muscular dystrophies in general are a group of clinically and genetically heterogeneous myopathies characterized by progressive degenerative changes in the skeletal muscles. This group of genetically distinct disorders shares clinical and pathological characteristics but varies in severity, inheritance pattern, and molecular defects. For example, DMD is caused by mutations or deletions in the dystrophin gene (chromosome Xp21) leading to its reduction at the mRNA level and absence at the protein level. This loss of dystrophin causes a fragility of the muscle membrane resulting in repeated rounds of muscle fiber necrosis and regeneration associated with chronic inflammation, as well as progressive replacement of the muscle fibers by fibrosis and fat in the later stages of the disease. Studies in animal models and in DMD subjects seem to suggest that the immune system could also contribute to the lesions observed in the skeletal muscles. An increased inflammation has been described in dystrophin-deficient muscles, and it has been shown that the in vivo depletion of $CD8^+$ T cells in the mdx mouse (the murine natural model of DMD) or the impairment of T cell cytotoxicity by the removal of perforin attenuates the disease. It has also been shown that irradiation of prenecrotic mdx mice improves or delays the pathological symptoms, presumably due to a decrease in the number of immune cells that can invade and kill the muscle. Finally, adoptive transfer of mdx immune cells in combination with muscle extracts resulted in muscle pathology in health murine recipients.

Thus, despite decades of scientific research, few effective myokine therapies have emerged to treat metabolic disorders and inflammatory disorders. Accordingly, there is a great need to identify molecular regulators of metabolic disorders and inflammatory-associated myopathy disorders, including the generation of diagnostic, prognostic, and therapeutic agents to effectively control such disorders in subjects.

SUMMARY OF THE INVENTION

The present invention is based in part on the discovery that Metrnl, Metrn, and biologically active fragments thereof are secreted polypeptides that have the ability to induce thermogenesis and brown fat gene programs in adipose tissue and inhibit inflammation in muscle (e.g., skeletal muscle). For example, although Metrnl was previously known to be expressed within the central nervous system in order to mediate neuroprotective and neurogenesis effects therein (U.S. Pat. No. 8,334,264) and was previously cloned by several groups (WO 93/22437; WO 01/039786), it was not taught, suggested or expected that Metrnl or Metrn would have any effect on adipose tissue and/or muscle tissue or that Metrnl and Metrn would be a myokine that systemically circulates in the body.

In one aspect, the present invention provides a method for modulating a metabolic response or muscle inflammation in a cell comprising, contacting a cell with an agent, wherein the agent comprises: (i) a Metrnl polypeptide that is at least 80% identical over its full length to a polypeptide selected from the group consisting of SEQ ID NO: 2, 4, 6, 8, 10, 12, 14, or 16 or a biologically active fragment thereof; (ii) a nucleic acid sequence that is expressed by the cell and encodes said Metrnl polypeptide or a biologically active fragment thereof of (i), wherein the nucleic acid sequence is at least 80% identical over its full length to a nucleic acid sequence selected from the group consisting of SEQ ID NO: 1, 3, 5, 7, 9, 11, 13, or 15 or a portion thereof that encodes the biologically active fragment; (iii) a nucleic acid sequence that is expressed by the cell and encodes the same polypeptide or fragment thereof encoded by the nucleic acid sequence of (ii), but differs in nucleic acid sequence therefrom due to degeneracy of the genetic code; (iv) a Metrn polypeptide that is at least 80% identical over its full length to a polypeptide selected from the group consisting of SEQ ID NO: 18, 20, 22, 24, 26, 28, or 30, or a biologically active fragment thereof; (v) a nucleic acid sequence that is expressed by the cell and encodes said Metrn polypeptide or a biologically active fragment thereof of (iv), wherein the nucleic acid sequence is at least 80% identical over its full length to a nucleic acid sequence selected from the group consisting of SEQ ID NO: 17, 19, 21, 23, 25, 27, or 29, or a portion thereof that encodes the biologically active fragment; or (vi) a nucleic acid sequence that is expressed by the cell and encodes the same polypeptide or fragment thereof encoded by the nucleic acid sequence of (v), but differs in nucleic acid sequence therefrom due to degeneracy of the genetic code, to thereby modulate the metabolic response or the muscle inflammation. In one embodiment, the agent comprises a Metrnl polypeptide sequence of SEQ ID NO: 2, 4, 6, 8, 10, 12, 14, or 16, or a biologically active fragment thereof, or comprises a Metrn polypeptide sequence of SEQ ID NO: 18, 20, 22, 24, 26, 28, or 30, or a biologically active fragment thereof. In another embodiment, the Metrnl and/or Metrn polypeptide or biologically active fragment thereof lacks a signal peptide. In still another embodiment, the agent comprises a i) Metrnl polypeptide-encoding nucleic acid sequence of SEQ ID NO: 1, 3, 5, 7, 9, 11, 13, or 15 or a fragment thereof that encodes a biologically active fragment of a Metrnl polypeptide, ii) nucleic acid sequence of i) that encodes the same polypeptide or active fragment, but differs in nucleotide sequence therefrom due to degeneracy of the genetic code, iii) Metrn polypeptide-encoding nucleic acid sequence of SEQ ID NO: 17, 19, 21, 24, 25, 27, or 29, or a fragment thereof that encodes a biologically active fragment of a Metrn polypeptide, or iv) nucleic acid sequence of iii) that encodes the same polypeptide or active fragment but differs in nucleotide sequence therefrom due to degeneracy of the genetic code. The Metrnl and/or Metrn polypeptide or biologically active fragment thereof can have the ability to promote one or more biological activities selected from the group consisting of: a) expression of a marker selected from the group consisting of: TNF-α, IL-6, IL-β, IL-10, TGF-β, ucp-1, cidea, dio2, pgc1β, err-α, pgc1α its isoforms, bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acylCoA-thioesterase 3; b) thermogenesis in adipose cells; c) differentiation of adipose cells; d) insulin sensitivity of adipose cells; e) basal respiration or uncoupled respiration; f) hepatosteatosis reduction; g) appetite reduction; h) insulin secretion of pancreatic beta cells; i) cardiac function reduction; j) cardiac hypertrophy; k) muscle hypoplasia reduction; and l) muscle inflammation inhibition.

In still another embodiment, the agent is a nucleic acid sequence and the encoded Metrnl and/or Metrn polypeptide or fragment thereof is secreted by a mammalian cell. In yet another embodiment, the Metrnl and/or Metrn polypeptide or biologically active fragment thereof further comprises a heterologous polypeptide fused thereto (e.g., an Fc domain a signal peptide, a peptide tag, a dimerization domain, an oligomerization domain, an antibody, or an antibody fragment). In another embodiment, the fused polypeptide has greater plasma solubility than the corresponding unfused Metrnl and/or Metrn polypeptide or biologically active fragment thereof. In still another embodiment, the agent is at least 75% pure. In yet another embodiment, the agent further comprises a pharmaceutically acceptable agent selected from the group consisting of excipients, diluents, and carriers. In another embodiment, the agent is a nucleic acid that is comprised within an expression vector (e.g., an adenoviral expression vector) or a cell. In still another embodiment, the method further comprises contacting the cell with an additional agent that increases the metabolic response and/or decreases muscle inflammation. In yet another embodiment, the step of contacting occurs in vivo, ex vivo, or in vitro. In another embodiment, the cell is selected from the group consisting of fibroblasts, myoblasts, myocytes, adipoblasts, adipocytes, white fat cells, brown fat cells, muscle cells, hepatocytes, and neural cells. In still another embodiment, the metabolic response or muscle inflammation is selected from the group consisting of: a) modified expression of a marker selected from the group consisting of: TNF-α, IL-6, IL-β, IL-10, TGF-β, ucp-1, cidea, dio2, pgc1β, err-α, pgc1α and its isoforms, bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acylCoA-thioesterase 3; b) modified thermogenesis in adipose cells; c) modified differentiation of adipose cells; d) modified insulin sensitivity of adipose cells; e) modified basal respiration or uncoupled respiration; f) modified hepatosteatosis; g) modified obesity or appetite; h) modified insulin secretion of pancreatic beta cells; i) modified cardiac function; j) modified cardiac hypertrophy; k) modified muscle hypoplasia; and l) modified muscle inflammation. In yet another embodiment, the method further comprises evaluating a metabolic response selected from a) through l).

In another aspect, the present invention provides a method for modulating a metabolic response or muscle inflammation comprising, contacting a cell with an agent that down regulates the activity of Metrnl and/or Metrn to thereby modulate the metabolic response or muscle inflammation. In one embodiment, the agent is selected from the group consisting of an anti-Metrnl and/or anti-Metrn antisense nucleic acid molecule, an anti-Metrnl and/or anti-Metrn RNA interference molecule, a blocking anti-Metrnl antibody, a non-activating form of Metrnl polypeptide or fragment thereof, a small molecule that binds to Metrnl, a blocking anti-Metrn antibody, a non-activating form of Metrn polypeptide or fragment thereof, and a small molecule that binds to Metrn. In another embodiment, the method further comprises contacting the cell with an additional agent that decreases the metabolic response and/or increases muscle inflammation. In still another embodiment, the step of contacting occurs in vivo, ex vivo, or in vitro. In yet another embodiment, the cell is selected from the group consisting of fibroblasts, myoblasts, myocytes, adipoblasts, adipocytes, white fat cells, brown fat cells, muscle cells, hepatocytes, and neural cells. In another embodiment, the metabolic response or muscle inflammation is selected from the group consisting of: a) modified expression of a marker selected from the group consisting of: TNF-α, IL-6, IL-β, IL-10, TGF-β, ucp-1, cidea, dio2, pgc1β, err-α, pgc1α and its isoforms, bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acylCoA-thioesterase 3; b) modified thermogenesis in adipose cells; c) modified differentiation of adipose cells; d) modified insulin sensitivity of adipose cells; e) modified basal respiration or uncoupled respiration; f) modified hepatosteatosis; g) modified obesity or appetite; h) modified insulin secretion of pancreatic beta cells; i) modified cardiac function; j) modified cardiac hypertrophy; k) modified muscle hypoplasia; and l) modified muscle inflammation. In still another embodiment, the method further comprises evaluating a metabolic response selected from a) through l).

In still another aspect, the present invention provides a method for preventing or treating a metabolic disorder or muscle inflammation in a subject comprising, administering to the subject, an agent, wherein the agent comprises: (i) a Metrnl polypeptide that is at least 80% identical over its full length to a polypeptide selected from the group consisting of SEQ ID NO: 2, 4, 6, 8, 10, 12, 14, or 16 or a biologically active fragment thereof; (ii) a nucleic acid sequence that that is expressed in the subject and encodes said Metrnl polypeptide or biologically active fragment thereof of (i), wherein the nucleic acid sequence is at least 80% identical over its full length to a nucleic acid sequence selected from the group consisting of SEQ ID NO: 1, 3, 5, 7, 9, 11, 13, or 15 or a portion thereof that encodes the biologically active fragment; (iii) a nucleic acid sequence that is expressed by the cell and that encodes the same polypeptide or biologically active fragment thereof encoded by the nucleic acid sequence of (ii), but differs in nucleic acid sequence therefrom due to degeneracy of the genetic code; (iv) a Metrn polypeptide that is at least 80% identical over its full length to a polypeptide selected from the group consisting of SEQ ID NO: 18, 20, 22, 24, 26, 28, or 30, or a biologically active fragment thereof; (v) a nucleic acid sequence that is expressed by the cell and encodes said Metrn polypeptide or a biologically active fragment thereof of (iv), wherein the nucleic acid sequence is at least 80% identical over its full length to a nucleic acid sequence selected from the group consisting of SEQ ID NO: 17, 19, 21, 23, 25, 27, or 29, or a portion thereof that encodes the biologically active fragment; or (vi) a nucleic acid sequence that is expressed by the cell and encodes the same polypeptide or fragment thereof encoded by the nucleic acid sequence of (v), but differs in nucleic acid sequence therefrom due to degeneracy of the genetic code, thereby preventing or treating the metabolic disorder or muscle inflammation in the subject. In one embodiment, the agent comprises a Metrnl polypeptide sequence of SEQ ID NO: 2, 4, 6, 8, 12, 14, or 16 or a biologically active fragment thereof. In another embodiment, the Metrnl polypeptide or biologically active fragment thereof lacks a signal peptide. In still another embodiment, the agent comprises a i) Metrnl polypeptide-encoding nucleic acid sequence of SEQ ID NO: 1, 3, 5, 7, 9, 11, 13, or 15, or a fragment thereof that encodes a biologically active fragment of a Metrnl polypeptide, ii) nucleic acid sequence of i) that encodes the same polypeptide or a biologically active fragment of any of the foregoing, but differs in nucleotide sequence therefrom due to degeneracy of the genetic code, iii) Metrn polypeptide-encoding nucleic acid sequence of SEQ ID NO: 17, 19, 21, 24, 25, 27, or 29, or a fragment thereof that encodes a biologically active fragment of a Metrn polypeptide, or iv) nucleic acid sequence of iii) that encodes the same polypeptide or active fragment but differs in nucleotide sequence therefrom due to degeneracy of the genetic code.

The Metrnl and/or Metrn polypeptide or biologically active fragment thereof has the ability to promote one or more biological activities selected from the group consisting of: a) expression of a marker selected from the group consisting of: TNF-α, IL-6, IL-β, IL-10, TGF-β, ucp-1, cidea, dio2, pgc1β, err-α, pgc1α and its isoforms, bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acyl-CoA-thioesterase 3; b) thermogenesis in adipose cells; c) differentiation of adipose cells; d) insulin sensitivity of adipose cells; e) basal respiration or uncoupled respiration; f) hepatosteatosis reduction; g) appetite reduction; h) insulin secretion of pancreatic beta cells; i) cardiac function reduction; j) cardiac hypertrophy; k) muscle hypoplasia reduction; and l) muscle inflammation inhibition. In another embodiment, the agent is a nucleic acid sequence and the encoded Metrnl and/or Metrn polypeptide or fragment thereof is secreted by a mammalian cell. In still another embodiment, the Metrnl and/or Metrn polypeptide or biologically active fragment thereof further comprises a heterologous polypeptide (e.g., Fc domain a signal peptide, a peptide tag, a dimerization domain, an oligomerization domain, an antibody, or an antibody fragment) fused thereto. In yet another embodiment, the fused polypeptide has greater plasma solubility than the corresponding unfused Metrnl and/or Metrn polypeptide or biologically active fragment thereof. In another embodiment, the agent is at least 75% pure. In still another embodiment, the agent further comprises a pharmaceutically acceptable agent selected from the group consisting of excipients, diluents, and carriers. In yet another embodiment, the agent is a nucleic acid comprised within an expression vector (e.g., an adenoviral expression vector) or a cell. In another embodiment, the method further comprises administering to the subject an additional agent that increases the metabolic response and/or decreases muscle inflammation. In still another embodiment, the agent is administered by intravenous or subcutaneous injection. In yet another embodiment, the metabolic disorder or muscle inflammation disorder is selected from the group consisting of obesity, insulin resistance, hyperinsulinemia, hypoinsulinemia, type II diabetes, hypertension, hyperhepatosteatosis, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome. In another embodiment, the muscle inflammation disorder is selected from the group consisting of Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (also known as Landouzy-Dejerine), Myotonic Dystrophy (MMD) (also known as Steinert's Disease), Oculopharyngeal Muscular Dystrophy (OPMD), Distal Muscular Dystrophy (DD), and Congenital Muscular Dystrophy (CMD), muscle hypoplasia, neurodegenerative diseases, and Alzheimer's disease. In still another embodiment, the subject is a human.

In yet another aspect, the present invention provides a method for preventing or treating a metabolic disorder in a subject comprising administering to the subject an agent that inhibits Metrnl and/or Metrn expression and/or activity in the subject, thereby preventing or treating the metabolic disorder in the subject. In one embodiment, the agent is selected from the group consisting of an anti-Metrnl and/or anti-Metrn antisense nucleic acid molecule, an anti-Metrnl and/or anti-Metrn RNA interference molecule, a blocking anti-Metrnl antibody, and a non-activating form of Metrnl polypeptide or fragment thereof, a small molecule that binds to Metrnl, a blocking anti-Metrn antibody, a non-activating form of Metrn polypeptide or fragment thereof, and a small molecule that binds to Metrn. In another embodiment, the agent is administered by intravenous or subcutaneous injection. In still another embodiment, the agent is administered in a pharmaceutically acceptable formulation. In yet another embodiment, the metabolic disorder is selected from the group consisting of obesity-associated cancer, anorexia, and cachexia. In another embodiment, the subject is a human.

In another aspect, the present invention provides a cell-based assay for screening for agents which modulate expression and/or activity of i) a Metrnl polypeptide that is at least 80% identical over its full length to a polypeptide selected from the group consisting of SEQ ID NO: 2, 4, 6, 8, 10, 12, 14, or 16, or a biologically active fragment thereof, or encoded by a nucleic acid that is at least 80% identical over its full length to a nucleic acid sequence selected from the group consisting of SEQ ID NO: 1, 3, 5, 7, 9, 11, 13, or 15, or a biologically active fragment thereof, or ii) a Metrn polypeptide that is at least 80% identical over its full length to a polypeptide selected from the group consisting of SEQ ID NO: 18, 20, 22, 24, 26, 28, or 30, or a biologically active fragment thereof, or encoded by a nucleic acid that is at least 80% identical over its full length to a nucleic acid sequence selected from the group consisting of SEQ ID NO: 17, 19, 21, 23, 25, 27, or 29, or a biologically active fragment thereof, comprising contacting a cell expressing the Metrnl and/or Metrn polypeptide with a test compound and determining the ability of the test agent to modulate one or more biological activities selected from the group consisting of: a) expression of a marker selected from the group consisting of: TNF-α, IL-6, IL-β, IL-10, TGF-β, ucp-1, cidea, dio2, pgc1β, err-α, pgc1α and its isoforms, bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acylCoA-thioesterase 3; b) thermogenesis in adipose cells; c) differentiation of adipose cells; d) insulin sensitivity of adipose cells; e) basal respiration or uncoupled respiration; f) hepatosteatosis reduction; g) appetite reduction; h) insulin secretion of pancreatic beta cells; i) cardiac function reduction; j) cardiac hypertrophy; k) muscle hypoplasia reduction; and l) muscle inflammation inhibition.

In still another aspect, the present invention provides a method for assessing the efficacy of an agent that modulates a metabolic response or muscle inflammation in a subject, comprising: i) measuring in a subject sample or subject at a first point in time, one or more biological activities selected from the group consisting of: a) expression of a marker selected from the group consisting of: TNF-α, IL-6, IL-β, IL-10, TGF-β, ucp-1, cidea, dio2, pgc1β, err-α, pgc1α and its isoforms, bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acylCoA-thioesterase 3; b) thermogenesis in adipose cells; c) differentiation of adipose cells; d) insulin sensitivity of adipose cells; e) basal respiration or uncoupled respiration; f) hepatosteatosis reduction; g) appetite reduction; h) insulin secretion of pancreatic beta cells; i) cardiac function reduction; j) cardiac hypertrophy; k) muscle hypoplasia reduction; and l) muscle inflammation inhibition; ii) repeating step a) during at least one subsequent point in time after administration of an agent that modulates the expression and/or activity of i) a Metrnl polypeptide that is at least 80% identical over its full length to a polypeptide selected from the group consisting of SEQ ID NO: 2, 4, 6, 8, 10, 12, 14, or 16, or a biologically active fragment thereof, or encoded by a nucleic acid that is at least 80% identical over its full length to a nucleic acid sequence selected from the group consisting of SEQ ID NO: SEQ ID NO: 1, 3, 5, 7, 9, 11, 13, or 15, or a biologically active fragment thereof, or ii) a Metrn polypeptide that is at least 80% identical over its full length to a polypeptide selected from the group consisting of SEQ ID NO: 18, 20, 22, 24, 26, 28, or 30, or a biologically active fragment thereof, or encoded by a nucleic acid that is at least 80% identical over its full length to a nucleic acid sequence selected from the group consisting of SEQ ID NO: 17, 19, 21, 23, 25, 27, or 29, or a biologically active fragment thereof; and iii) comparing the expression and/or activity detected in steps a) and b), wherein a significant difference in the first biological activity measurement relative to the at least one subsequent biological activity measurement, indicates that the test agent modulates a metabolic response or muscle inflammation in the subject.

BRIEF DESCRIPTION OF FIGURES

FIG. 2A shows Metrnl protein expression levels in plasma, as determined by Western blot analysis, from mice injected with the LacZ- or Metrnl-expressing adenoviral particles. FIG. 2B shows quantitative polymerase chain reaction (qPCR) results of thermogenic gene expression in subcutaneous inguinal fat from mice injected with the LacZ- or Metrnl-expressing adenoviral particles. Data shown are representative of two independent experiments and bar graphs are mean+/−standard error of the mean (S.E.M.).

DETAILED DESCRIPTION OF THE INVENTION

Figure 1:
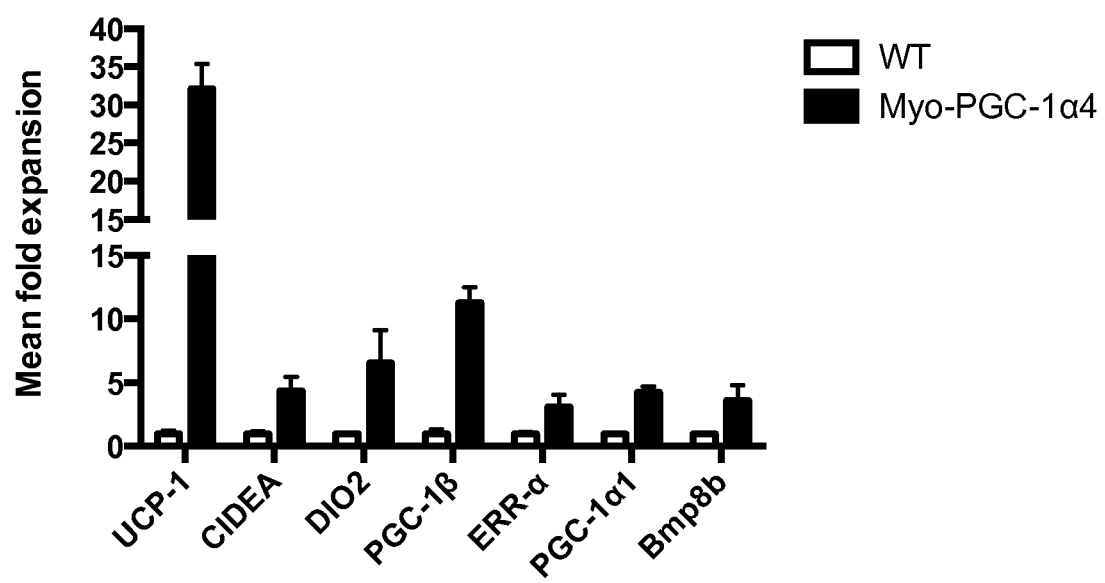
FIG. 1 shows quantitative polymerase chain reaction (qPCR) results of thermogenic gene expression in subcutaneous inguinal fat depots from myogenin promoter-driven PGC-1α4 transgenic mice and littermate controls (n=4).

The present invention is based in part on the discovery that Metrnl, Metrn, and biologically active fragments thereof are secreted polypeptides that have the ability to induce significant induction of thermogenesis and brown fat gene programs in adipose tissue and inhibit inflammation in skeletal muscle. Brown fat gene programs can be induced in white adipose tissue in order to promote thermogenesis upon myokine signaling received by white adipose cells from the expression and/or activity of Metrnl, Metrn, or biologically active fragments thereof. The compositions and methods described herein are capable of activating a distinct set of target genes (including, for example but not limited to, TNF-α, IL-6, IL-β, IL-10, TGF-β, ucp-1, cidea, dio2, pgc1β, err-α, pgc1α and its isoforms (e.g., pgc1α1), bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acyl-CoA-thioesterase 3) characteristic of brown fat cells or downstream effects of brown fat cells. Increased brown fat cell program induction in mammals using Metrnl, Metrn, and biologically active fragments thereof can result in many therapeutically beneficial endpoints for regulating metabolic disorders, such as the ability to induce the expression of mitochondrial genes (including, for example but not limited to, cytochrome c, cox 4i1, cox III, cox 5b, cox8b, atpase b2, cox II, atp5o and ndufb5); increase cellular respiration (i.e., total and uncoupled respiration); increase insulin sensitivity and thermogenesis of adipose cells; increase insulin sensitivity of muscle and hepatic cells; decrease hepatosteatosis, obesity, type II diabetes, and appetite; increase insulin secretion of pancreatic beta cells; increases cardiac function to combat cardiac hypertrophy; improve muscle hypoplasia; and reduce the growth and effects of obesity-associated cancer, cachexia, and anorexia. Muscle-related inflammation can also be inhibited via myokine signaling received by muscle cells (e.g., skeletal muscle cells) resulting from the expression and/or activity of Metrnl, Metrn, or biologically active fragments thereof. The compositions and methods described herein are capable of significantly altering the expression of pro-inflammatory genes, such as TNF-α, IL-6, and IL-β, as well as anti-inflammatory genes, such as IL-10 and TGF-β, in such treated muscle cells.

In order that the present invention may be more readily understood, certain terms are first defined. Additional definitions are set forth throughout the detailed description. The term "altered amount" of a marker or "altered level" of a marker refers to increased or decreased copy number of the marker and/or increased or decreased expression level of a particular marker gene or genes in a cancer sample, as compared to the expression level or copy number of the marker in a control sample. The term "altered amount" of a marker also includes an increased or decreased protein level of a marker in a sample, e.g., a cancer sample, as compared to the protein level of the marker in a normal, control sample.

The "amount" of a marker, e.g., expression or copy number of a marker or MCR, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a cancer sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "altered subcellular localization" of a marker refers to the mislocalization of the marker within a cell relative to the normal localization within the cell e.g., within a healthy and/or wild-type cell. An indication of normal localization of the marker can be determined through an analysis of subcellular localization motifs known in the field that are harbored by marker polypeptides.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

The term "antisense" nucleic acid refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarity, or, for example, in the case of binding to DNA duplexes, through specific interactions in the major groove of the double helix.

The term "binding" or "interacting" refers to an association, which may be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" when used in reference to a diagnostic assay is intended to include tissues, cells and biological fluids isolated from a subject, as well as tissues, cells and fluids present within a subject.

As used herein, the term "inhibit" includes the decrease, limitation, or blockage, of, for example a particular action, function, or interaction. For example, muscle inflammation is "inhibited" if at least one symptom of muscle inflammation, such as overexpression of pro-inflammatory genes or underexpression of anti-inflammatory genes, is alleviated, terminated, slowed, or prevented. As used herein, cancer is also "inhibited" if recurrence or metastasis of the cancer is reduced, slowed, delayed, or prevented.

The term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

As used herein, the term "inflammatory-associated myopathy disorders" refers to any condition in which inflammation of muscle itself or in a location involving muscle cells is undesired. Included within the scope of such disorders are "muscular dystrophies," which collectively refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Moreover, declining muscle mass and diminishing physical activity contribute to an imbalance between caloric intake and energy expenditure, leading to unhealthy storage of excess energy as white adipose tissue. Exemplary muscular dystrophies that can be treated with the compositions and methods described herein include, without limitation, Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (also known as Landouzy-Dejerine), Myotonic Dystrophy (MMD) (also known as Steinert's Disease), Oculopharyngeal Muscular Dystrophy (OPMD), Distal Muscular Dystrophy (DD), and Congenital Muscular Dystrophy (CMD).

The terms "metabolic disorder" and "obesity related disorders" are used interchangeably herein and include a disorder, disease or condition which is caused or characterized by an abnormal or unwanted metabolism (i.e., the chemical changes in living cells by which energy is provided for vital processes and activities) in a subject. Metabolic disorders include diseases, disorders, or conditions associated with aberrant or unwanted (higher or lower) thermogenesis or aberrant or unwanted levels (high or low) adipose cell (e.g., brown or white adipose cell) content or function. Metabolic disorders can be characterized by a misregulation (e.g., downregulation or upregulation) of PGC-1 activity. Metabolic disorders can detrimentally affect cellular functions such as cellular proliferation, growth, differentiation, or migration, cellular regulation of homeostasis, inter- or intra-cellular communication; tissue function, such as liver function, muscle function, or adipocyte function; systemic responses in an organism, such as hormonal responses (e.g., insulin response). Examples of metabolic disorders include obesity, insulin resistance, type II diabetes, hypertension, hyperuricemia, fatty liver, non-alcoholic fatty liver disease, polycystic ovarian syndrome, acanthosis *nigricans*, hyperphagia, endocrine abnormalities, triglyceride storage disease, Bardet-Biedl syndrome, Lawrence-Moon syndrome, Prader-Labhart-Willi syndrome, anorexia, and cachexia.

As used herein, the term "Metrnl" refers to meteorin-like polypeptides and nucleic acid molecules encoding such polypeptides and is further intended to include fragments, variants (e.g., allelic variants) and derivatives thereof. The nucleotide and amino acid sequences of mouse Metrnl, which correspond to Genbank Accession number NM_144797.3 and NP_659046.1, respectively, are set forth in SEQ ID NOs: 1 and 2. Residues 1-45 of SEQ ID NO: 2 define a signal peptide, such that the mature murine Metrnl polypeptide contains residues 46-311 of SEQ ID NO: 2. Similarly, the nucleotide and amino acid sequences of human Metrnl, which correspond to Genbank Accession number NM_001004431.1 and NP_001004431.1, respectively, are set forth in SEQ ID NOs: 3 and 4. Residues 1-45 of SEQ ID NO: 4 define a signal peptide, such that the mature human Metrnl polypeptide contains residues 46-311 of SEQ ID NO: 4. Nucleic acid and polypeptide sequences of Metrnl orthologs in organisms other than mice and humans are well known and include, for example, chicken Metrnl (XM_415598.3; XP_415598.1), zebrafish Metrnl (BC046006.1; AAH46006.1), rat Metrnl (NM_001014104.1; NP_001014126.1), cow Metrnl (NM_001206050.1; NP_001192979.1), and frog Metrnl (NM_001097653.1; NP_001091122.1). Other useful Metrnl sequences that can be used according to the compositions and methods described herein are described in U.S. Pat. No. 8,334,264, which is hereby incorporated herein in its entirety.

In some embodiments, fragments of Metrnl having one or more biological activities of the full-length Metrnl protein are described and employed. Such fragments can comprise or consist of at least one domain of an Metrnl protein other than the signal peptide without containing the full-length Metrnl protein sequence. In some embodiments, Metrnl fragments can comprise or consist of a substantially full-length Metrnl protein (e.g., the full-length Metrnl protein minus 1, 2, 3, 4, 5, 10, 15, 20, 25, or 30 or any range in between) or larger fragments with or without the signal peptide. As demonstrated by the sequences presented in Table 1, Metrnl orthologs are highly homologous and retain common structural domains well known in the art.

As used herein, the term "Metrn" refers to meteorin polypeptides and nucleic acid molecules encoding such polypeptides and is further intended to include fragments, variants (e.g., allelic variants) and derivatives thereof. The nucleotide and amino acid sequences of mouse Metrn, which correspond to Genbank Accession number NM_133719.2 and NP_598480.1, respectively, are set forth in SEQ ID NOs: 17 and 18. Residues 1-21 of SEQ ID NO: 18 define a signal peptide, such that the mature murine Metrn polypeptide contains residues 22-291 of SEQ ID NO: 18. Similarly, the nucleotide and amino acid sequences of human Metrn, which correspond to Genbank Accession number NM_024042.2 and NP_076947.1, respectively, are set forth in SEQ ID NOs: 19 and 20. Residues 1-23 of SEQ ID NO: 20 define a signal peptide, such that the mature human Metrn polypeptide contains residues 24-293 of SEQ ID NO: 20. Nucleic acid and polypeptide sequences of Metrnl orthologs in organisms other than mice and humans are well known and include, for example, chimpanzee Metrn (XM_001156928.3; XP_001156928.1), cow Metrn (NM_001102026.2; NP_001095496.1), rat Metrn (NM_001009962.1; NP_00100962.1), chicken Metrn (XM_425223.4; XP_425223.3), and zebrafish Metrn (NM_001009983.2; NP_001009983.2).

In some embodiments, fragments of Metrn having one or more biological activities of the full-length Metrn protein are described and employed. Such fragments can comprise or consist of at least one domain of an Metrn protein other than the signal peptide without containing the full-length Metrn protein sequence. In some embodiments, Metrn fragments can comprise or consist of a substantially full-length Metrn protein (e.g., the full-length Metrn protein minus 1, 2, 3, 4, 5, 10, 15, 20, 25, or 30 or any range in between) or larger fragments with or without the signal peptide. As demonstrated by the sequences presented in Table 1, Metrn orthologs are highly homologous and retain common structural domains well known in the art.

TABLE 1

```
SEQ ID NO: 1 Mouse Metrnl cDNA Sequence
    1 atgcggggtg cggtgtgggc ggcccggagg cgcgcggggc agcagtggcc tcggtccccg
   61 ggccctgggc cgggtccgcc cccgccgcca ccgctgctgt tgctgctact actgctgctg
  121 ggcggcgcga gcgctcagta ctccagcgac ctgtgcagct ggaaggggag tgggctcacc
  181 cgagaggcac gcagcaagga ggtggagcag gtgtacctgc gctgctccgc aggctctgtg
  241 gagtggatgt acccaactgg ggcgctcatt gttaacctac ggcccaacac cttctcacct
  301 gcccagaact tgactgtgtg catcaagcct ttcagggact cctctggagc caatatttat
  361 ttggaaaaaa ctggagaact aagactgttg gtgcgggaca tcagaggtga gcctggccaa
  421 gtgcagtgct tcagcctgga gcagggaggc ttatttgtgg aggcgacacc ccaacaggac
  481 atcagcagaa ggaccacagg cttccagtat gagctgatga gtgggcagag gggactggac
  541 ctgcacgtgc tgtctgcccc ctgtcggcct tgcagtgaca ctgaggtcct ccttgccatc
  601 tgtaccagtg actttgttgt ccgaggcttc attgaggacg tcacacatgt accagaacag
  661 caagtgtcag tcatctacct gcgggtgaac aggcttcaca ggcagaagag cagggtcttc
  721 cagccagctc ctgaggacag tggccactgg ctgggccatg tcacaacact gctgcagtgt
  781 ggagtacgac cagggcatgg ggaattcctc ttcactggac atgtgcactt tggggaggca
  841 caacttggat gtgccccacg ctttagtgac tttcaaagga tgtacaggaa agcagaagaa
  901 atgggcataa acccctgtga aatcaatatg gagtga SEQ ID NO: 2 Mouse Metrnl Amino Acid Sequence (Signal Peptide: Residues 1-45)
    1 mrgavwaarr ragqqwprsp gpgpgppppp pllllllllll ggasaqyssd lcswkgsglt
   61 rearskeveq vylrcsagsv ewmyptgali vnlrpntfsp aqnltvcikp frdssganiy
  121 lektgelrll vrdirgepgq vqcfsleqgg lfveatpqqd isrrttgfqy elmsgqrgld
  181 lhvlsapcrp csdtevllai ctsdfvvrgf iedvthvpeq qvsviylrvn rlhrqksrvf
  241 qpapedsghw lghvttllqc gvrpghgefl ftghvhfgea qlgcaprfsd fqrmyrkaee
  301 mginpceinm e SEQ ID NO: 3 Human Metrnl cDNA Sequence
    1 atgcggggcg cggcgcgggc ggcctggggg cgcgcggggc agccgtggcc gcgacccccc
   61 gccccgggcc cgccccgcc gccgctcccg ctgctgctcc tgctcctggc cgggctgctg
  121 ggcggcgcgg cgcgcagta ctccagcgac cggtgcagct ggaaggggag cgggctgacg
  181 cacgaggcac acaggaagga ggtggagcag gtgtatctgc gctgtgcggc gggtgccgtg
  241 gagtggatgt acccaacagg tgctctcatc gttaacctgc ggcccaacac cttctcgcct
  301 gcccggcacc tgaccgtgtg catcaggtcc ttcacggact cctcggggc caatatttat
  361 ttggaaaaaa ctggagaact gagactgctg gtaccggacg gggacggcag gcccggccgg
  421 gtgcagtgtt ttggcctgga gcagggcggc ctgttcgtgg aggccacgcc gcagcaggat
  481 atcggccgga ggaccacagg cttccagtac gagctggtta ggaggcacag ggcgtcggac
  541 ctgcacgagc tgtctgcgcc gtgccgtccc tgcagtgaca ccgaggtgct cctagccgtc
  601 tgcaccagcg acttcgccgt tcgaggctcc atccagcaag ttacccacga gcctgagcgg
  661 caggactcag ccatccacct gcgcgtgagc agactctatc ggcagaaaag caggtgtcttc
  721 gagccggtgc ccgagggtga cggccactgg caggggcgcg tcaggacgct gctggagtgt
  781 ggcgtgcggc cggggcatgg cgacttcctc ttcactggcc acatgcactt cggggaggcg
  841 cggctcggct gtgcccacg cttcaaggac ttccagagga tgtacaggga tgcccaggag
  901 aggggcctga acccttgtga ggttggcacg gactga SEQ ID NO: 4 Human Metrnl Amino Acid Sequence (Signal Peptide: Residues 1-45)
    1 mrgaaraawg ragqpwprpp apgppppplp lllllllagll ggagaqyssd rcswkgsglt
   61 heahrkeveq vylrcaagav ewmyptgali vnlrpntfsp arhltvcirs ftdssganiy
  121 lektgelrll vpdgdgrpgr vqcfgleqgg lfveatpqqd igrrttgfqy elvrrhrasd
  181 lhelsapcrp csdtevllav ctsdfavrgs iqqvtheper qdsaihlrvs rlyrqksrvf
  241 epvpegdghw qgrvrtllec gvrpghgdfl ftghmhfgea rlgcaprfkd fqrmyrdaqe
  301 rglnpcevgt d SEQ ID NO: 5 Chicken Metrnl cDNA Sequence
    1 atgccgctat ttacttcttt tctgaactcc tttggactgc tgacaattga tgcgtcctta
   61 atccccgcga atccacttca aggcgagtcc gttcgtggct taactcacga gtctcacaag
  121 aaggatgttg aacaggtcta cctccgctgt tccgaaggct ccatagagtg gatgtatccc
  181 acgggagcgc tcatagtcaa cctgcgaccc aacacttcac ctgcctccta caaacatttg
  241 actgtttgca taaagccctt caaggactct gcaggagcaa atatttattt ggaaaaaact
  301 ggagaactca aactcttggt ccgaagtgga gagcgcagcc ccagcaaggt gtactgcttt
  361 ggctacgacc aggggggct gtttgtcgag gccacccccc agcaggacat tagcaggaag
  421 atcacaggct tccagtacga actgatgagc aggggggattg catctgattt gcacacagtt
  481 tctgctccat gccgaccatg cagtgacaca gaggtcctct ggccgtctg cactagtgat
  541 ttcgtgatca gaggctccat tcaagatgta acaaatgagg cagaagagca agaatccata
  601 attcacgttg gcgtcaacaa actgtacagg cagaagagca aagtcttttca gctcacgggg
  661 gagagtggga actggcgagg acaaataaag acctgctgg agtgtggggt gagaccagga
  721 gatggagact tcctcttcac gggacgcatg cactttgggg aagccaggtt aggctgtgcc
```

TABLE 1-continued

```
781 cctcgattta aagacttcca aaggatgtac aaagaagcaa aagacaaagg gctaaatcca
841 tgtgaaattg gcccagattg a
```

SEQ ID NO: 6 Chicken Metrnl Amino Acid Sequence (Signal Peptide: Residues 1-26)
```
  1 mplftsflns fglltidasl ipanplqges vrgltheshk kdveqvylrc segsiewmyp
 61 tgalivnlrp ntspasykhl tvcikpfkds aganiylekt gelkllvrdg erspskvycf
121 gydqgglfve atpqqdisrk itgfqyelms rgiasdlhtv sapcrpcsdt evllavctsd
181 fvirgsiqdv tneaeeqesi ihvgvnklyr qkskvfqltg esgnwrggik tllecgvrpg
241 dgdflftgrm hfgearlgca prfkdfqrmy keakdkglnp ceigpd
```

SEQ ID NO: 7 Zebrafish Metrnl cDNA Sequence
```
  1 atgctctcgc cgttcttggc gtatttgctg tcggttgtgc ttctgtgtcg gattgcgcgc
 61 tcccagtact caagtgatca gtgcagctgg aggggcagtg gactgaccca tgagggacac
121 actcggggtg tggagcaggt gtatctccgc tgcgcccagg ggttcctgga gtggctgtac
181 cccactggcg caatcatcgt caacctgcgg ccaaacacgc tgtcacccgc agcgtctctt
241 ctctccgtct gcatcaaacc ctccaaggag tccagcggga cccacatcta ccttgacaga
301 ctgggaaaat tgcgactgct cctcagcgaa ggggatcagg ccgagggtaa agtgcactgc
361 ttcaacatcc aggatggggc gctcttcatc gaagctgtgc ctcaaaggga catcagccga
421 aaaatcacag ccttccagta tgagctggtc aaccacagac caggagcaga tccacagtca
481 ttatctgctc cctgccaacc gtgtacagat gcagaggtcc tgctggccgt ctgcaccagt
541 gactttgtgg cgcggggggag aattcttggt gtatccgagg aggatgaaca gacctcagtc
601 acagtgtcct taagtcacct atatagacag aagactcaag tgtttgtgtc aggggggcgc
661 cgggctaaac gctggacagg ctttgtgaag atgtccaggc agtgcggggt taaaccaggg
721 gacgcgagt ttcttttcac cgggactgtg cgattcggag aggcctggct cagctgcgct
781 ccacgctaca aggacttcct tagggtgtac caggacgcgc ggcagcaagg gaccaaccc
841 tgtcatttgg aaacagactg a
```

SEQ ID NO: 8 Zebrafish Metrnl Amino Acid Sequence (Signal Peptide: Residues 1-21)
```
  1 mlspflayll svvllcriar sqyssdqcsw rgsglthegh trgveqvylr caqgflewly
 61 ptgaiivnlr pntlspaasl lsvcikpske ssgthiyldr lgklrlllse gdqaegkvhc
121 fniqdgalfi eavpqrdisr kitafqyelv nhrpgadpqs lsapcqpctd aevllavcts
181 dfvargrilg vseedeqtsv tvslshlyrq ktqvfvsggg rakrwtgfvk msrqcgvkpg
241 dgeflftgtv rfgeawlsca prykdflrvy qdarqqgtnp chletd
```

SEQ ID NO: 9 Rat Metrnl cDNA Sequence
```
  1 atgcgggtg tggtgtgggc ggcccggagg cgcgcggggc agcagtggcc tcggtccccg
 61 ggccctgggc cgggtccgcc cccgccgcca ccgctgctgt tgctgctact gctgctgctg
121 ggcggcgcga gcgcgcagta ctccagcgac ctgtgcagct ggaaggggag tgggctcacc
181 cggaggcac acagcaagga ggtggagcag gtgtacctgc gctgctcagc aggctctgtg
241 gaatggatgt acccaaccgg ggcgctcatt gttaacctac ggcccaacac cttctcacct
301 gcccagaact tgactgtgtg catcaagcct ttcagggact cctctggggc caatatttat
361 ttggaaaaaa ctggagaact aagactgttg gtgcgggatg tcagaggcga acctggccaa
421 gtgcagtgct tcagcctaga gcagggaggc ttatttgtg aggccacacc ccagcaggac
481 atcagcagaa ggaccacagg cttccagtat gagctgatga gtgggcagag gggactggac
541 ctgcacgtgc tctctgcccc ctgtcgacct tgcagcgaca ctgaggtcct ccttgccatc
601 tgcaccagtg actttgttgt ccgaggcttc atcgaggatg tcacccatgt accagaacag
661 caagtgtcag tcattcacct acgggtgagc aggctccaca ggcagaagag cagggtcttc
721 cagccagctc ctgaggacag tggccactgg ctgggccatg tcacaacact gttgcagtgt
781 ggagtacgac cagggcatgg agaattcctc ttcactggac atgtgcactt ggggaggca
841 caacttggat gtgccccacg cttttagtgac tttcaaaaga tgtacaggaa agcagaagaa
901 aggggcataa ccccttgtga aataaatatg gagtga
```

SEQ ID NO: 10 Rat Metrnl Amino Acid Sequence (Signal Peptide: Residues 1-45)
```
  1 mrgvvwaarr ragqqwprsp gpgpgppppp plllllllll ggasaqyssd lcswkgsglt
 61 reahskeveq vylrcsagsv ewmyptgali vnlrpntfsp aqnltvcikp frdssganiy
121 lektgelrll vrdvrgepgq vqcfsleqgg lfveatpqqd isrrttgfqy elmsgqrgld
181 lhvlsapcrp csdtevllai ctsdfvvrgf iedvthvpeq qvsvihlrvs rlhrqksrvf
241 qpapedsghw lghvttllqc gvrpghgefl ftghvhfgea qlgcaprfsd fqkmyrkaee
301 rginpceinm e
```

SEQ ID NO: 11 Cow Metrnl cDNA Sequence
```
  1 atgcggggcg cgacgcgggc ggctgggggg cgcgcggggc agctgtggcc gaggcccccc
 61 gcccccgggcc ctggaccgcc gccgctgctg ctgctgctgg ccgtgctact gggcggccgcg
121 ggcgcgcagt actcgagcga cctgtgcagc tggaagggga gcgggctgac acacgaggcc
181 cacaggaagg aggtggagca gtttacctg cgctgctcgg cgggcaccgt cgagtggatg
241 tacccgaccg ggcgctcat cgtgaaccta cggcccaaca ccttctcgcc ctcccggaac
301 ctgactctgt gcatcaagcc ccttagggc cctcggggg ccaatattta tttggaaaag
361 actggagaac tgaaactgct ggtgagggat ggggaccctcg gcccggcca ggcgccgtgc
421 tttggcttcg agcagggggg cctgtttgtg gagcgacgc cacagcaaga catcagcagg
481 aggaccacgg gcttccagta cgagctgacc agcaggcgca cggggccgga cctgcacgcc
541 ctgttggccc cgtgccgcc ttgcagccac acagaggttc tcttggccgt ctgcaccagc
601 gactttgtcg tccgaggctc catccagaaa gtcacccacg agccggagcg gcaggagtcg
661 gccatccacc tgaacgtgag ccggctctac cggcagaaga gcagggtgtt ccggccggcc
721 cctgagggcc agggcggcgg ctggcggggg gcgtctccca cgctactgga gtgcggcgtc
781 cggcctggcc acggcgagtt tcttcttcacc ggccacatgc actttgggga ggcctggctt
841 ggctgcgcac cacgcttcaa ggatttccaa aggatgtaca gggacgctga ggagagggg
901 ctgaaccct gcgagatggg cacggagtga
```

SEQ ID NO: 12 Cow Metrnl Amino Acid Sequence (Signal Peptide: Residues 1-42)
```
  1 mrgatraagg ragqlwprpp apgpgppppll lllavllgga gaqyssdlcs wkgsglthea
```

TABLE 1-continued

```
  61 hrkeveqvyl rcsagtvewm yptgalivnl rpntfspsrn ltlcikplrg ssganiylek
 121 tgelkllvrd gdlgpgqapc fgfeqgglfv eatpqqdisr rttgfqyelt srrtgpdlha
 181 llapcrpcsh tevllavcts dfvvrgsiqk vtheperqes aihlnvsrly rqksrvfrpa
 241 pegegggwrg rvstllecgv rpghgeflft ghmhfgeawl gcaprfkdfq rmyrdaeerg
 301 lnpcemgte
```

SEQ ID NO: 13 Frog Metrnl cDNA Sequence
```
   1 atgttaagga ggggtctgct gagcttcttt atggtgattc ttatagacag agggacctca
  61 cagctgtact ccagcgacat gtgcaattgg aaaggaagcg gcttgaccca tgagggccac
 121 acgaaagatg ttgagcaagt ttacctccgc tgctccagaa gttctgttga gtggctctac
 181 ccaactggcg ccatggttat taacctgagg cctaacacct aacgtccgc ctacaaacac
 241 ctaacagttt gcatcaaacc tttttaaagac tccaagggag ctaatattta ttccgaaaaa
 301 actggagaac tcaaacttgt ggtgccagat ggagagaaca atccacacaa agtctattgc
 361 tttggcctgg atcgagggg tctgtatatt gaggccaccc cccagcaaga cattagtcgc
 421 aaaatcactg gtttccagta tgaactgatc agccagagga ctctctcgga tttgcacaca
 481 gtttctgatc cctgccgccc ctgcagtgat acagaagtcc tgctagctgt ctgtattagt
 541 gatttcgttg tgaaagggac aatcagcgct gtgaccaata atgaggagtt gcaggaatct
 601 ctgatcaacg tcacggtgga taaactgtac aggcagaaga gtaaaatctt ccttcccaaa
 661 gacaatgggg gatgggaggg aatgataacg actcctctgg aatgtggggt taagacggga
 721 atgggcagct tcttgttcac gggacgcatg cactttgggg agcccagatt gggctgcacg
 781 ccccggtata aggactttaa aaggatatac ctagaagcga aaaagcaagg gttaaaccca
 841 tgtgaaatca gcacggactg a
```

SEQ ID NO: 14 Frog Metrnl Amino Acid Sequence (Signal Peptide: Residues 1-21)
```
   1 mlrrgllsff mvilidrgts qlyssdmcnw kgsglthegh tkdveqvylr csegsvewly
  61 ptgamvinlr pntltsaykh ltvcikpfkd skganiysek tgelklvvpd gennphkvyc
 121 fgldrgglyi eatpqqdisr kitgfqyell sqrtlsdlht vsdpcrpcsd tevllavcis
 181 dfvvkgtisa vtndeelqes linvtvdkly rqkskiflpk dnggwegmir tplecgvktg
 241 mgsflftgrm hfgeprlgct prykdfkriy leakkqglnp ceistd
```

SEQ ID NO: 15 Mouse Metrnl cDNA Sequence With C-Terminal V5 Epitope Tag
```
ATGCGGGGTGCGGTGTGGGCGGCCCGGAGGCGCGCGGGGCAGCAGTGGCCTCGGTCCCCGGGCCCTGGGC
CGGGTCCGCCCCCGCCGCCACCGCTGCTGTTGCTGCTACTACTGCTGTGGGCGGCGCGAGCGCTCAGTA
CTCCAGCGACCTGTGCAGCTGGAAGGGGAGTGGGCTCACCCGAGAGGCACGCAGCAAGGAGGTGGAGCAG
GTGTACCTGCGCTGCTCCGCAGGCTCTGTGGAGTGGATGTACCCAACTGGGGCGCTCATTGTTAACCTAC
GGCCCAACACCTTCTCACCTGCCCAGAACTTGACTGTGTGCATCAAGCCTTTCAGGGACTCCTCTGGAGC
CAATATTTATTTGGAAAAAACTGGAGAACTAAGACTGTTGGTGCGGGACATCAGAGGTGAGCCTGGCCAA
GTGCAGTGCTTCAGCCTGGAGCAGGGAGGCTTATTTGTGGAGGCAGCACCCCAACAGGACATCAGCAGAA
GGACCACAGGCTTCCAGTATGAGCTGATGAGTGGGCAGAGGGGACTGGACCTGCACGTGCTGTCTGCCCC
CTGTCGGCCTTGCAGTGACACTGAGGTCCTCCTTGCCATCTGTACCAGTGACTTTGTTGTCCGAGGCTTC
ATTGAGGACGTCACACATGTACCAGAACAGCAAGTGTCAGTCATCTACCTGCGGGTGAACAGGCTTCACA
GGCAGAAGAGCAGGGTCTTCCAGCCAGCTCCTGAGGACAGTGGCCACTGGCTGGGCCATGTCACAACACT
GCTGCAGTGTGGAGTACGACCAGGGCATGGGGAATTCCTCTTCACTGGACATGTGCACTTTGGGGAGGCA
CAACTTGGATGTGCCCCACGCTTTAGTGACTTTCAAAGGATGTACAGGAAAGCAGAAGAAATGGGCATAA
ACCCCTGTGAAATCAATATGGAGGACCCAGCTTTCTTGTACAAGTGGTTGATCTAGAGGGCCCGCGGTT
CGAAGGTAAGCCTATCCCTAACCCTCTCCTCGGTCTCGATTCTACGCGTACCGGTTAGTAATGA
```

SEQ ID NO: 16 Mouse Metrnl Amino Acid Sequence With C-Terminal V5 Epitope Tag
```
MRGAVWAARRRAGQQWPRSPGPGPGPPPPPPLLLLLLLLLGGASAQYSSDLCSWKGSGLT
REARSKEVEQVYLRCSAGSVEWMYPTGALIVNLRPNTFSPAQNLTVCIKPFFRDSSGANIY
LEKTGELRLLVRDIRGEPGQVQCFSLEQGGLFVEATPQQDISRRTTGFQYELMSGQRGLD
LHVLSAPCRPCSDTEVLLAICTSDFVVRGFIEDVTHVPEQQVSVIYLRVNRLHRQKSRVF
QPAPEDSGHWLGHVTTLLQCGVRPGHGEFLFTGHVHFGEAQLGCAPRFSDFQRMYRKAEE
MGININPCEINMEDPAFLYKVVDLEGPRFEGKPIPNPLLGLDSTRTG
```

SEQ ID NO: 17 Mouse Metrn cDNA Sequence
```
   1 atgctggtag ccacgcttct ttgcgcgctc tgttgcggcc tcctggccgc gtccgctcac
  61 gctggcactact cggaagaccg ctgcagctgg aggggcagcg gtttgaccca ggagcctggc
 121 agcgtggggc agctgacccct ggactgtact gagggcgcta tcgagtggct gtacccagct
 181 ggggcgctgc gcctgaccct gggcggcccc gatccgggca cacggcccag catcgtctgt
 241 ctgcgcccag agcggcccctt cgctggtgcc caggtcttcg ctgaacgtat gaccggcaat
 301 ctagagttgc tactggccga gggcccggac ctggctgggg gccgctgcat gcgctggggt
 361 ccccgcgagc gccgagccct tttcctgcag gccacaccac accgcgacat cagccgcaga
 421 gttgctgcct tccgttttga actgcacgag gaccaacgtg cagaaatgtc tccccaggct
 481 caaggtcttg gtgtggatgg tgcctgcagg ccctgcagtg atgccgagct cctcctggct
 541 gcatgcacca gtgattttgt gatccacggg accatccatg gggtcgccca tgacacagag
 601 ctgcaagaat cagtcatcac tgtggtggtt gctcgtgtca tccgccagac actgccactg
 661 ttcaaggaag ggagctcgga gggccaaggc cgggcctcca ttcgtacctt gctgcgctgt
 721 ggtgtgcgtc ctgggccagg ctccttcctc ttcatggcgt ggagccgatt tggcgaagct
 781 tggctgggct gtgctcccg cttccaagag ttcagccgtg tctattcagc tgctctcacg
 841 acccatctca acccatgtga gatggcactg gactga
```

SEQ ID NO: 18 Mouse Metrn Amino Acid Sequence (Signal Peptide: Residues 1-21)
```
   1 mlvatllcal ccgllaasah agysedrcsw rgsgltqepg svgqltldct egaiewlypa
  61 galrltlggp dpgtrpsivc lrperpfaga qvfaermtgn lelllaegpd laggrcmrwg
 121 prerralflq atphrdisrr vaafrfelhe dqraemspqa qglgvdgacr pcsdaellla
 181 actsdfvihg tihgvandte lqesvitvvv arvirqtlpl fkegssegqg rasirtllrc
 241 gvrpgpgsfl fmgwsrfgea wlgcaprfqe fsrvysaalt thlnpcemal d
```

TABLE 1-continued

SEQ ID NO: 19 Human Metrn cDNA Sequence
    1 atggggttcc cggccgcggc gctgctctgc gcgctgtgct gcggcctcct ggccccggct
   61 gcccgcgccg gctactccga ggagcgctgc agctggaggg gcagcggcct cacccaggag
  121 cccggcagcg tggggcagct ggccctggcc tgtgcggagg gcgcggttga gtggctgtac
  181 ccggctgggg cgctgcgcct gacccctggg ggccccgatc ccagagcgcg gcccggcatc
  241 gcctgtctgc ggccggtgcg gcccttcgcg ggcgcccagg tcttcgcgga gcgcgcaggg
  301 ggcgccctgg agctgctgct ggccgagggc ccggggcccgg caggggggccg ctgcgtgcgc
  361 tggggtcccc gcgagcgccg ggccctcttc ctgcaggcca cgccgcacca ggacatcagc
  421 cgccgcgtgg ccgccttccg ctttgagctg cgcgaggacg ggcgccccga gctgcccccg
  481 caggcccacg gtctcggcgt agacggtgcc tgcaggccct gcagcgacgc tgagctgctc
  541 ctggccgcat gcaccagcga cttcgtaatt cacgggatca tccatggggt cacccatgac
  601 gtggagctgc aggagtctgt catcactgtg gtggccgccc gtgtcctccg ccagacaccg
  661 ccgctgttcc aggcggggcg atccggggac caggggctcc cctccattcg taccccactg
  721 cgctgtggcg tccacccggg cccaggcacc ttcctcttca tgggctggag ccgctttggg
  781 gaggcccggc tgggctgtgc cccacgattc caggagttcc gccgtgccta cgaggctgcc
  841 cgtgctgccc acctccaccc ctgcgaggtg gcgctgcact ga SEQ ID NO: 20 Human Metrn Amino Acid Sequence (Signal Peptide: Residues 1-23)
    1 mgfpaaallc alccgllapa aragyseerc swrgsgltqe pgsvgqlala caegavewly
   61 pagalrltlg gpdprarpgi aclrpvrpfa gaqvfaerag galelllaeg pgpaggrcvr
  121 wgprerralf lqatphqdis rrvaafrfel redgrpelpp qahglgvdga crpcsdaell
  181 laactsdfvi hgiihgvthd velqesvitv vaarvlrqtp plfqagrsgd qgltsirtpl
  241 rcgvhpgpgt flfmgwsrfg earlgcaprf qefrrayeaa raahlhpcev alh SEQ ID NO: 21 Chimpanzee Metrn cDNA Sequence
    1 atggggttcc cggccgcggc gctgctctgc gcgctgtgct gcggcctcct ggccccggcc
   61 gcccgcgccg gctactccga ggagcgctgc agctggaggg gcagcggcct cacccaggag
  121 cctggcagcg tggggcagct ggccctggcc tgtgcggagg gcgcggttga gtggctgtac
  181 cccgctgggg cgctgcgcct gacccctggg ggccccgatc ccagagcgcg gcccggcatc
  241 gcctgtctgc ggccggtgcg gcccttcgcg ggcgcccagg tcttcgcgga gcgcgcaggg
  301 ggcgccctgg agctgctgct ggccgagggc ccggggcccgg caggggggccg ctgcgtgcgc
  361 tggggtcccc gcgagcgccg ggccctcttc ctgcaggcca cgccgcaccg ggacatcagc
  421 cgccgcgtgg ccgccttccg ctttgagctg cgcgaggacg ggcgccccga gctgcccccg
  481 caggcccacg gtctcggcgt agacggtgcc tgcaggccct gcagcgatgc tgagctgctc
  541 ctggccgcat gcaccagcga cttcgtaatt cacgggatca tccatggggt cgcccatgac
  601 gtggagctgc aggaatctgt catcaccgtg gtggccgccc gtgtcctccg ccagacaccg
  661 ccgctgttcc aggcggggcg atccggggac caggggctga cctccattcg tactccactg
  721 cgctgtggcg tccgcccggg cccaggcacc ttcctcttca tgggctggag ccgcttcggg
  781 gaggcctggc tgggctgtgc cccacgattc caggagttcc gccgtgccta cgaggctgcc
  841 cgtgctgccc acctccaccc ctgcgaggtg gcgctgcact ga SEQ ID NO: 22 Chimpanzee Metrn Amino Acid Sequence (Signal Peptide: Residues 1-23)
    1 mgfpaaallc alccgllapa aragyseerc swrgsgltqe pgsvgqlala caegavewly
   61 pagalrltlg gpdprarpgi aclrpvrpfa gaqvfaerag galelllaeg pgpaggrcvr
  121 wgprerralf lqatphrdis rrvaafrfel redgrpelpp qahglgvdga crpcsdaell
  181 laactsdfvi hglihgvahd velqesvitv vaarvlrqtp plfqagrsgd qgltsirtpl
  241 rcgvrpgpgt flfmgwsrfg eawlgcaprf qefrrayeaa raahlhpcev alh SEQ ID NO: 23 Cow Metrn cDNA Sequence
    1 atgccgacct ctgcgctgct ctgcacactt tgcttctgcc tcttggccgc ggccgctcgc
   61 gccggctact cggaggaccg ctgcagctgg aggggcagcg gcctgaccca ggagcccggc
  121 agcgtgggac agctcgccct ggcctgtgcg gacggcaaga tcgagtggct gtacccggcc
  181 ggggcgctgc gcctcaccct gggcggctct gagcccagcg cgcagcccgg catcgtctgc
  241 ctgcggccga cgcggccctt cgcaggcgcc caagtcttcg tggagcggac gggcggcggg
  301 ctagagttgc tgctggccga gggccagggc ccggtggcgc gcgctggggg
  361 cctcgcgagc gccgggccct cttcctgcag gccaccccgc atcccgacct cagccgccgc
  421 ttggcctcct tccgcttcca gctgcgggag acgggcgtc cggagctgcc cccgcaggcc
  481 cgcagccttg gagcggatgc tgcctgcaga ccctgcagtg atgccgagct cctcctggcc
  541 gtgtgcacca gtgactttgt gatctacgga accatcctg gagttgccca caacgcagag
  601 ctacaggagt ctgtcatcac cgtggcagct gcacgtgtcc tccgccagac gctgccggtt
  661 ttctgggtgg gggccctgg ggccagggg caggcctcca ttcgcacccc actgcactgt
  721 ggcgtgcgcc ctggccctgg caccttcctc ttcatgggct ggaaccgctt tggtgaggcc
  781 tggctgggct gtgctcccg cctccaggaa ttcagccgtg cctacgcggc tgcccacgct
  841 gaccacctgc acccctgcga ggtggtgctg gactga SEQ ID NO: 24 Cow Metrn Amino Acid Sequence (Signal Peptide: Residues 1-21)
    1 mptsallctl cfcllaaaar agysedrcsw rgsgltqepg svgqlalaca dgkiewlypa
   61 galrltlggs epsaqpgivc lrptrpfaga qvfvertggg lelllaegqg pagarcarwg
  121 prerralflq atphpdlsrr lasfrfqlre dgrpelppqa rslgadaacr pcsdaellla
  181 vctsdfviyg tilgvahnae lqesvitvaa arvlrqtlpv fwvggpggqg qasirtplhc
  241 gvrpgpgtfl fmgwnrfgea wlgcaprlqe fsrayaaaha dhlhpcevvl d SEQ ID NO: 25 Rat Metrn cDNA Sequence
    1 atgctggtag cggcgcttct ctgcgcgctg tgctgcggcc tcttggctgc gtccgctcga
   61 gctggctact ccgaggaccg ctgcagctgg aggggcagcg gcgttgaccca ggaacctggc
  121 agcgtggggc agctgaccct ggattgtact gagggtgcta tcgagtggct gtatccagct
  181 ggggcgctgc gcctgactct aggcggctct gatccgggca cgcggcccag catcgtctgt
  241 ctgcgcccaa cacggccctt cgctggtgcc caggtcttcg ctgaaccggat ggccggcaac
  301 ctagagttgc tactggccga aggccaaggc ctggctgggg ccgctgcat gcgctggggt
  361 cctcgcgagc gccgagccct tttcctgcag gccacgccac accgggacat cagccgcaga TABLE 1-continued

```
421 gttgctgcct tccaatttga actgcacgag gaccaacgtg cagaaatgtc tccccaggcc
481 caaggttttg gtgtggatgg tgcctgcagg ccctgcagtg atgccgagct ccttctgact
541 gcatgcacca gtgactttgt gatccatggg accatccatg gggtcgtcca tgacatggag
601 ctgcaagaat cagtcatcac tgtggtggcc actcgtgtca tccgccagac atgccactg
661 ttccaggaag ggagctcgga gggccggggc caggcctccg ttcgtaccttgttgcgctgt
721 ggtgtgcgtc ctgcccagg ctccttcctc ttcatgggctggagccgatt tggcgaagct
781 tggctgggct gcgctccccg cttccaagag ttcagccgtg tctattcagc tgctctcgcg
841 gcccacctca acccatgtga ggtggcactg gactga SEQ ID NO: 26 Rat Metrn Amino Acid Sequence (Signal Peptide: Residues 1-21)
  1 mlvaallcal ccgllaasar agysedrcsw rgsgltqepg svgqltldct egaiewlypa
 61 galrltlggs dpgtrpsivc lrptrpfaga qvfaermagn lelllaegqg laggrcmrwg
121 prerralflq atphrdisrr vaafqfelhe dqraemspqa qgfgvdgacr pcsdaellt
181 actsdfvihg tihgvvhdme lqesvitvva trvirqtlpl fqegssegrg qasvrtllrc
241 gvrpgpgsfl fmgwsrfgea wlgcaprfqe fsrvysaala ahlnpceval d SEQ ID NO: 27 Chicken Metrn cDNA Sequence
  1 atgcgggctc tgtgggcgct gtgcctcgcc gggctggccg ctgccctcgg cagcttctcg
 61 gcggatcagt gcagctggag ggggagcggc ttgtcgcagg aggcgggcag cgtggagcag
121 ctcaccctgc gctgcgccga gggctccctg gagtggctgt accccacggg agccctccgc
181 ctccgcttgg ccccccgcc gccccccgcc accaccgccg atggccgcga ccccgacac
241 gtcaccgcct gccttcagcc cgccggcacc ttccgggggg ctcagctcta cctggagcgg
301 gatggggagc tggagctgct gctgcccgag gcggaggcgg ccccgcggcc ccgtgtgagg
361 tgtttcagct ggccacccca tgagcaggtg gcctgttcc tgcaggccac cccgcagcgc
421 gacatcagcc gccgcatcgc tgccttccgc tatgagctgc gggggactg gctcgcccgc
481 cctgcactgc ctgccgaagg ggtgtgccgg ccgtgcaacg acaccgagct cctgatggcc
541 atttgcacta gtgactttgt ggtccgcggt accatccaca gcgtctccaa cgacgcagag
601 ctgcaggaat ccgtcatcgg ggtgagtgcc gtccgcatcc accgccagaa attcccctc
661 ttccaaaccg ggggcggcc ggggagggcg gtgggcagca tccgcacccc tctgcgctgc
721 ggtgtgcggc cgggcccgg caccttcctc ttcacggggt ggctgcactt tggcgaggca
781 tggctcagct gcgctccccg ctacaaggac ttccagcgca tctacgaggg cgcccggcgc
841 aggaggcaga acccctgcga gttccccgtg gactga SEQ ID NO: 28 Chicken Metrn Amino Acid Sequence (Signal Peptide: Residues 1-21)
  1 mralwalcla glaaalgsfs adqcswrgsg lsqeagsveq ltlrcaegsl ewlyptgalr
 61 lrlaprlppa ttadgrdprh vtaclqpagt frgaqlyler dgelelllpe aeaaprprvr
121 cfswppheqv alflqatpqr disrriaafr yelrgdwlar palpaegvcr pcndtellma
181 ictsdfvvrg tihsvsndae lqesvigvsa vrihrqkfpl fqtggrpgra vgsirtplrc
241 gvrpgpgtfl ftgwlhfgea wlscaprykd fqriyegarr rrqnpcefpv d SEQ ID NO: 29 Zebrafish Metrn cDNA Sequence
  1 atggagattt ggggatttag gagtgttgcg ctatggattt cattcctgac ggggttggtcg
 61 atggccagtt actcagaaga tcagtgcagc tggagaggaa gtggactttc tcaggcggtg
121 aagaatgtgg agcaggtttg gttgaggtgt gcggagggct cggtggagtg gttgtatcct
181 gctggagctt tgcgtctcac cctgtcgccc cgtctgccat ggagtgccat ggggccgggc
241 gagtccagca ggagcccggt gtcagtctgc gtcaagcctg atccacactg gggtggggct
301 cagctgtatc tggagcgcga tggagtcctg gagcttctgg tgggagatga gacctccacc
361 acacccggcc cagcccatgt acgctgcttt agtgccctgc ccggagaacg acctgcactg
421 ttcctgcagg ccacaccgca ccgggatatc agcagacgca tcgctgcctt ccgctacgag
481 ctgagagggg attggacggc gcagccagca gtcaacacag atccagtcag cagcgaagga
541 gcctgcagac cctgcaataa cactgagatc ctgatggccg tctgcactag tgactttgtg
601 gttcgaggaa acatccgctc agtgggaaca gactcgaatc taaaagcagc cgtgatcaaa
661 gtgagtgcga cgcgggttta ccggcagaag tttgcgttgt tccctgaatc tgggcgtctg
721 acgcgtttag gcgagatccg taccccctcta caatgtggcg ttcgtcctgg tgcaggcagt
781 ttcctcttca ccggacgcgt gcatttcggg gaggcctggc ttggctgcgc tccaagatat
841 aaagactttc tgaaggcgta cgaacaggcc aaacaatcct tgatgatccc ctgcactctt
901 gtcaatgact ga SEQ ID NO: 30 Zebrafish Metrn Amino Acid Sequence (Signal Peptide: Residues 1-22)
  1 meiwgfrsva lwisfltgws masysedqcs wrgsglsqav knveqvwlrc aegsvewlyp
 61 agalrltlsp rlpwsamgpg essrspvsvc vkpdphwgga qlylerdgvl ellvgdetst
121 tpgpahvrcf salpgerpal flqatphrdi srriaafrye lrgdwtaqpa vntdpvsseg
181 acrpcnntei lmavctsdfv vrgnirsvgt dsnlkaavik vsatrvyrqk falfpesgrl
241 trlgeirtpl qcgvrpgags flftgrvhfg eawlgcapry kdflkayeqa kqslmipctl
301 vnd
```

As used herein, "obesity" refers to a body mass index (BMI) of 30 kg/m² or more (National Institute of Health, Clinical Guidelines on the Identification, Evaluation, and Treatment of Overweight and Obesity in Adults (1998)). However, the present invention is also intended to include a disease, disorder, or condition that is characterized by a body mass index (BMI) of 25 kg/m² or more, 26 kg/m² or more, 27 kg/m² or more, 28 kg/m² or more, 29 kg/m² or more, 29.5 kg/m² g, m² Of more, or 29.9 kg/m² or more, all of which are typically referred to as overweight (National Institute of Health, Clinical Guidelines on the Identification, Evaluation, and Treatment of Overweight and Obesity in Adults (1998)). The obesity described herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

An "overexpression" or "significantly higher" level of expression, activity, copy number, and the like, of a marker (e.g., Metrnl, Metrn, or downstream signaling marker thereof) refers to an expression level or copy number in a test sample that is greater than the standard error of the assay employed to assess expression or copy number, but is preferably at least 1.2, 1.3, 1.4, 1.5, 1.6, 1.7, 1.8, 1.9, 2.0, 2.1, 2.2, 2.3, 2.4, 2.5 and more preferably three, four, five or ten or more times greater than the expression, activity, copy number, and the like, of the marker in a control sample (e.g., sample from a healthy subject not afflicted with a metabolic disorder and/or muscle inflammation) and preferably, the average expression level or copy number of the marker in several control samples.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as muscle or adipose tissue sample. In certain instances, the method of the present invention further comprises obtaining the sample from the individual prior to detecting or determining the presence or level of at least one marker in the sample.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. 1998. Science 282:63), and natural product extract libraries. In another embodiment, the compounds are small, organic non-peptidic compounds. In a further embodiment, a small molecule is not biosynthetic.

The term "subject" refers to any healthy animal, mammal or human, or any animal, mammal or human afflicted with a condition of interest (e.g., metabolic disorder and/or muscle inflammation). The term "subject" is interchangeable with "patient."

An "underexpression" or "significantly lower level" of expression, activity, copy number, and the like, of a marker (e.g., Metrnl, Metrn, or downstream signaling marker thereof) refers to an expression level or copy number in a test sample that is greater than the standard error of the assay employed to assess expression or copy number, but is preferably at least 1.2, 1.3, 1.4, 1.5, 1.6, 1.7, 1.8, 1.9, 2.0, 2.1, 2.2, 2.3, 2.4, 2.5 and more preferably three, four, five or ten or more times less than the expression, activity, copy number, and the like, of the marker in a control sample (e.g., sample from a healthy subject not afflicted with a metabolic disorder and/or muscle inflammation) and preferably, the average expression level or copy number of the marker in several control samples.

It will be appreciated that specific sequence identifiers (SEQ ID NOs) have been referenced throughout the specification for purposes of illustration and should therefore not be construed to be limiting. Any marker of the invention, including, but not limited to, the markers described in the specification and markers described herein (e.g., TNF-α, IL-6, IL-β, IL-10, TGF-β, ucp-1, cidea, dio2, pgc1β, err-α, pgc1α and its isoforms (e.g., pgc1α1), bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acylCoA-thioesterase 3), are well known in the art and can be used in the embodiments of the invention as listed, for example, in Table 2.

TABLE 2

| Gene Symbol | Gene Name | GenBank Gene Accession Number | GenBank Protein Accession Number | Gene ID |
| --- | --- | --- | --- | --- |
| TNF-α | Tumor necrosis factor | e.g., NM_013693.2 and NM_000594.3 | e.g., NP_038721.1 and NP_000585.2 | e.g., 21926 and 7124 |
| IL-6 | Interleukin 6 | e.g., NM_031168.1 and NM_000600.3 | e.g., NP_112445.1 and NP_000591.1 | e.g., 16193 and 3569 |
| IL-β | Interleukin 1 beta | e.g., NM_008361.3 and NM_000576.2 | e.g., NP_032387.1 and NP_000567.1 | e.g., 16176 and 3553 |
| IL-10 | Interleukin 10 | e.g., NM_010548.2 and NM_000572.2 | e.g., NP_034678.1 and NP_000563.1 | e.g., 16153 and 3586 |
| TGF-β | Transforming growth factor, beta 1 | e.g., NM_011577.1 and NM_000660.4 | e.g., NP_035707.1 and NP_000651.3 | e.g., 21803 and 7040 |
| pgc1β | peroxisome proliferative activated receptor, gamma, coactivator 1 beta | e.g., NM_133249.2 and NM_001172698.1 and NM_001172699.1 and NM_133263.3 and | e.g., NP_573512.1 and NP_001166169.1 and NP_001166170.1 and NP_573570.3 and | e.g., 170826 and 133522 |
| err-α | estrogen related receptor, alpha | e.g., NM_007953.2 and NM_004451.3 | e.g., NP_031979.2 and NP_004442.3 | e.g., 26379 and 2101 |
| bmp8b | bone morphogenetic protein 8b | e.g., NM_007559.4 and NM_001720.3 | e.g., NP_031585.2 and NP_001711.2 | e.g., 12164 and 656 |
| adipsin | complement factor D | e.g., NM_013459.2 and NM_001928.2 | e.g., NP_038487.1 and NP_001919.2 | e.g., 11537 and 1675 |

TABLE 2-continued

| Gene Symbol | Gene Name | GenBank Gene Accession Number | GenBank Protein Accession Number | Gene ID |
|---|---|---|---|---|
| fatty acid transporter cd36 | fatty acid transporter/cd36 | e.g., NM_007643.3 and NM_000072.3 and NM_001001547.2 and NM_001001548.2 and NM_001127443.1 and NM_001127444.1 | e.g., NP_031669.2 and NP_000063.2 and NP_001001547.1 and NP_001001548.1 and NP_001120915.1 and NP_001120916.1 | e.g., 12491 and 948 |
| adiponectin | adiponectin | e.g., NM_009605.4 and NM_004797.2 | e.g., NP_0033735.3 and NP_004788.1 | e.g., 11450 and 9370 |
| UCP-1 | uncoupling protein 1 | e.g., NM_009463.3 and NM_021833.4 | e.g., NP_033489.1 and NP_068605.1 | e.g., 22227 and 7350 |
| cidea | cell death-inducing DFFA-like effector a | e.g., NM_007702.2 and NM_001279.3 and NM_198289.2 | e.g., NP_031728.1 and NP_001270.1 and NP_938031.1 | e.g., 12683 and 1149 |
| PGC1a (i.e., PGC1α1) | Peroxisome proliferative activated receptor, gamma, coactivator 1 alpha | e.g., NM_008904.2 and NM_013261.3 | e.g., NP_032930.1 and NP_037393.1 | e.g., 19017 and 10891 |
| Elovl3 | elongation of very long chain fatty acids (FEN1/Elo2, SUR4/Elo3, yeast)-like 3 | e.g., NM_007703.2 and NM_152310.1 | e.g., NP_031729.1 and NP_689523.1 | e.g., 12686 and 83401 |
| C/EBPbeta | CCAAT/enhancer binding protein beta | e.g., NM_009883.3 and NM_005194.2 | e.g., NP_034013.1 and NP_005185.2 | e.g., 12608 and 1051 |
| Cox7a1 | cytochrome c oxidase subunit VIIa polypeptide 1 | e.g., NM_009944.3 and NM_001864.2 | e.g., NP_034074.1 and NP_001855.1 | e.g., 12865 and 1346 |
| Otopetrin | Otopetrin 1 | e.g., NM_172709.3 and NM_177998.1 | e.g., NP_766297.2 and NP_819056.1 | e.g., 21906 and 133060 |
| Type II deiodinase | Deiodinase, iodothyronine, type II | e.g., NM_010050.2 and NM_000793.4 and NM_001007023.2 and NM_013989.3 | e.g., NP_034180.1 and NP_000784.2 and NP_001007024.1 and NP_054644.1 | e.g., 13371 and 1734 |
| cytochrome C | cytochrome c | e.g., NM_009989.2 and NM_018947.4 | e.g., NP_034119.1 and NP_061820.1 | e.g., 13067 and 54205 |
| cox4i1 | cytochrome c oxidase subunit IV isoform 1 | e.g., NM_009941.2 and NM_001861.2 | e.g., NP_034071.1 and NP_001852.1 | e.g., 12857 and 1327 |
| coxIII | mitochondrially encoded cytochrome c oxidase III | e.g., NC_005089.1 and ENST00000362079 | e.g., NP_904334.1 and ENSP00000354982 | e.g., 17705 and 4514 |
| cox5b | cytochrome c oxidase subunit Vb | e.g., NM_009942.2 and NM_001862.2 | e.g., NP_034072.2 and NP_001853.2 | e.g., 12859 and 1329 |
| cox8b | cytochrome c oxidase subunit 8B, mitochondrial precursor | e.g., NM_007751.3 | e.g., NP_031777.1 | e.g., 12869 and 404544 |
| glut4 | solute carrier family 2 (facilitated glucose transporter), member 4 | e.g., NM_009204.2 and NM_001042.2 | e.g., NP_033230.2 and NP_001033.1 | e.g., 20528 and 6517 |
| atpase b2 | ATPase, H+ transportying, lysosomal 56/58 kDa, V1 subunit B2 | e.g., NM_057213.2 and NM_001693.3 | e.g., NP_476561.1 and NP_001684.2 | e.g., 117596 and 526 |
| coxII | mitochondrially encoded cytochrome c oxidase II | e.g., NC_005089.1 and ENST00000361739 | e.g., NP_904331 and ENSP00000354876 | e.g., 17709 and 4513 |
| atp5o | ATP synthase, H+ transporting, mitochondrial F1 complex, O subunit | e.g., NM_138597.2 and NM_001697.2 | e.g., NP_613063.1 and NP_001688.1 | e.g., 28080 and 539 |
| ndufb5 | NADH dehydrogenase (ubiquinone) 1 beta subcomplex, 5, 16 kDa | e.g., NM_025316.2 and NM_002492.2 | e.g., NP_079592.2 and NP_002483.1 | e.g., 66046 and 4711 |
| Rarres2 | retinoic acid receptor responder (tazarotene induced) 2 | e.g., NM_027852.2 and NM_002889.3 | e.g., NP_082128.1 and NP_002880.1 | e.g., 71660 and 5919 |
| Car3 | carbonic anhydrase 3 | e.g., NM_007606.3 and NM_005181.3 | e.g., NP_031632.2 and NP_005172.1 | e.g., 12350 and 761 |
| Peg 10 | paternally expressed 10 | e.g., NM_001040611.1 and NM_001040152.1 and NM_001172437.1 and NM_001172438.1 and NM_015068.3 | e.g., NP_001035701.1 and NP_001035242.1 and NP_001165908.1 and NP_001165909.1 and NP_055883.2 | e.g., 170676 and 23089 |
| Cidec | Cidec cell death-inducing DFFA-like effector c | e.g., NM_178373.3 and NM_022094.2 | e.g., NP_848460.1 and NP_071377.2 | e.g., 14311 and 63924 |

TABLE 2-continued

| Gene Symbol | Gene Name | GenBank Gene Accession Number | GenBank Protein Accession Number | Gene ID |
|---|---|---|---|---|
| Cd24a | CD24a antigen | e.g., NM_009846.2 and NM_013230.2 | e.g., NP_033976.1 and NP_037362.1 | e.g., 12484 and 100133941 |
| Nr1d2 | nuclear receptor subfamily 1, group D, member 2 | e.g., NM_011584.4 and NM_001145425.1 and NM_005126.4 | e.g., NP_035714.3 and NP_001138897.1 and NP_005117.3 | e.g., 353187 and 9975 |
| Ddx17 | DEAD (Asp-Glu-Ala-Asp) box polypeptide 17 | e.g., NM_001040187.1 and NM_001098504.1 and NM_001098505.1 and NM_006386.4 and NM_030881.3 | e.g., NP_001035277.1 and NP_001091974.1 and NP_001091975.1 and NP_006377.2 and NP_112020.1 | e.g., 67040 and 10521 |
| Aplp2 | amyloid beta (A4) precursor-like protein 2 | e.g., NM_001102455.1 and NM_001142276.1 and NM_001142277.1 and NM_001142278.1 and NM_001642.2 | e.g., NP_001095925.1 and NP_001135748.1 and NP_001135749.1 and NP_001135750.1 and NP_001633.1 | e.g., 11804 and 334 |
| Nr3c1 | nuclear receptor subfamily 3, group C, member 1 | e.g., NM_008173.3 and NM_000176.2 and NM_001018074.1 and NM_001018075.1 and NM_001018076.1 and NM_001018077.1 and NM_001020825.1 and NM_001024094.1 | e.g., NP_032199.3 and NP_000167.1 and NP_001018084.1 and NP_001018085.1 and NP_001018086.1 and NP_001018087.1 and NP_001018661.1 and NP_001019265.1 | e.g., 14815 and 2908 |
| Rybp | RING1 and YY1 binding protein | e.g., NM_019743.3 and NM_012234.4 | e.g., NP_062717.2 and NP_036366.3 | e.g., 56353 and 23429 |
| Txnip | thioredoxin interacting protein | e.g., NM_001009935.2 and NM_006472.3 | e.g., NP_001009935.1 and NP_006463.3 | e.g., 56338 and 10628 |
| Cig30 | Elongation of very long chain fatty acids-like 3 | e.g., NM_152310.1 and NM_007703.1[1] | e.g., NP_689523.1 and NP_031729.1[1] | e.g., 83401 and 12686 |
| Ppar gamma 2 | Peroxisome proliferator-activated receptor gamma 2 | e.g., NM_015869.4 and NM_011146.2[1] | e.g., NP_056953 and NP_035276.1[1] | e.g., 5468 and 19016 |
| Prdm16 | PR domain containing 16 protein | e.g., NM_022114.3 and NM_199454.2 and NM_027504.3 | e.g., NP_071397.3 and NP_955533.2 and NP_081780.3 | e.g., 63976 and 70673 |
| Apt | Fatty acid binding protein 4 | e.g., NM_001442.2 and NM_024406.1 | e.g., NP_001433.1 and NP_077717.1 | e.g., 2167 and 11770 |
| Ndufs2 | NADH dehydrogenase (ubiquinone) Fe-S protein 2, 49 kDa (NADH-coenzyme Q reductase | e.g., NM_001166159.1 and NM_004550.4 and NM_153064.4 | e.g., NP_001159631.1 and NP_004541.1 and NP_694704.1 | e.g., 4720 and 226646 |
| Grp109A | Hydroxycarboxylic acid receptor 2 | e.g., NM_177551 and NM_030701.3 | e.g., NP_808219 and NP_109626.1 | e.g., 338442 and 80885 |
| AcylCoA-thioesterase 4 | Acyl-coenzyme A thioesterase 4 | e.g., NM_152331 and NM_134247.3 | e.g., NP_689544 and NP_599008.3 | e.g., 122970 and 171282 |
| Claudin1 | Claudin1 | e.g., NM_021101.4 and NM_016674.4 | e.g., NP_066924.1 and NP_057883.1 | e.g., 9076 and 12737 |
| PEPCK | Phosphoenolpyruvate carboxykinase (mitochondrial) | e.g., NM_001018073.1 and NM_004563.2 and NM_028994.2 | e.g., NP_001018083.1 and NP_004554.2 and NP_083270.1 | e.g., 5106 and 74551 |
| Fgf21 | Fibroblast growth factor 21 | e.g., NM_019113 and NM_020013.4 | e.g., NP_061986 and NP_064397.1 | e.g., 26291 and 56636 |
| AcyCoA-thioesterase 3 | Acyl-coenzyme A thioesterase 4 | e.g., NM_001037161.1 and NM_134246.3 | e.g., NP_001032238.1 and NP_599007.1 | e.g., 641371 and 171281 |
| Dio2 | Type II iodothyronine deiodinase | e.g., NM_00793.5 and NM_010050.2 | e.g., NP_000784.2 and NP_034180.1 | e.g., 1734 and 13371 |

I. Isolated Nucleic Acids

One aspect of the invention pertains to methods utilizing isolated nucleic acid molecules that encode Metrnl, Metrn, or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Metrnl and/or Metrn nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a muscle cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO: 1, 3, 5, 7, 9, 11, 13, 15, 17, 19, 21, 23, 25, 27, or 29, or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence shown in SEQ ID NOs: 1, 3, 5, 7, 9, 11, 13, 15, 17, 19, 21, 23, 25, 27, or 29, or a portion thereof (i.e., 100, 200, 300, 400, 450, 500, or more nucleotides), can be isolated using standard molecular biology techniques and the sequence information provided herein. For example, a human Metrnl or Metrn cDNA can be isolated from a human muscle cell line (from Stratagene, La Jolla, Calif., or Clontech, Palo Alto, Calif.) using all or portion of SEQ ID NOs: 1, 3, 5, 7, 9, 11, 13, 15, 17, 19, 21, 23, 25, 27, or 29, or fragment thereof, as a hybridization probe and standard hybridization techniques (i.e., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989). Moreover, a nucleic acid molecule encompassing all or a portion of SEQ ID NOs: 1, 3, 5, 7, 9, 11, 13, 15, 17, 19, 21, 23, 25, 27, or 29, or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NOs: 1, 3, 5, 7, 9, 11, 13, 15, 17, 19, 21, 23, 25, 27, or 29, or fragment thereof, can be isolated by the polymerase chain reaction using oligonucleotide primers designed based upon the sequence of SEQ ID NOs: 1, 3, 5, 7, 9, 11, 13, 15, 17, 19, 21, 23, 25, 27, or 29, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NOs: 1, 3, 5, 7, 9, 11, 13, 15, 17, 19, 21, 23, 25, 27, or 29, or fragment thereof, or to the homologous nucleotide sequence. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an Metrnl and/or Metrn nucleotide sequence can be prepared by standard synthetic techniques, i.e., using an automated DNA synthesizer.

Probes based on the Metrnl and/or Metrn nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express an Metrnl and/or Metrn protein, such as by measuring a level of an Metrnl-encoding and/or Metrn-encoding nucleic acid in a sample of cells from a subject, i.e., detecting Metrnl and/or Metrn mRNA levels.

Nucleic acid molecules encoding other Metrnl and/or Metrn members and thus which have a nucleotide sequence which differs from the Metrnl and/or Metrn sequences of SEQ ID NOs: 1, 3, 5, 7, 9, 11, 13, 15, 17, 19, 21, 23, 25, 27, or 29, or fragment thereof, are contemplated. Moreover, nucleic acid molecules encoding Metrnl and/or Metrn proteins from different species, and thus which have a nucleotide sequence which differs from the Metrnl sequences of SEQ ID NOs: 1, 3 5, 7, 9, 11, 13, 15, 17, 19, 21, 23, 25, 27, or 29 are also intended to be within the scope of the present invention. For example, chimpanzee or monkey Metrnl and/or Metrn cDNA can be identified based on the nucleotide sequence of a human and/or mouse Metrnl and/or Metrn, respectively.

In one embodiment, the nucleic acid molecule(s) of the invention encodes a protein or portion thereof which includes an amino acid sequence which is sufficiently homologous to an amino acid sequence of SEQ ID NO: 2, 4, 6, 8, 10, 12, 14, 16, 18, 20, 22, 24, 26, 28, or 30, or fragment thereof, such that the protein or portion thereof modulates (e.g., enhance), one or more of the following biological activities: 1) it can modulate the expression of TNF-α, IL-6, IL-β, IL-10, TGF-β, ucp-1, cidea, dio2, pgc1β, err-α, pgc1α and its isoforms (e.g., pgc1α1), bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acyl-CoA-thioesterase 3; 2) it can increase cellular respiration (i.e., total and uncoupled respiration); 3) it can increase thermogenesis of adipose cells; 4) it can increase insulin sensitivity of adipose, muscle and/or hepatic cells; 5) it can decrease hepatosteatosis, obesity, type II diabetes, and/or appetite; 6) it can increase insulin secretion of pancreatic beta cells; 7) it can increase cardiac function to combat cardiac hypertrophy; 8) it can improve muscle hypoplasia; 9) it can reduce the growth and effects of obesity-associated cancer, cachexia, and anorexia; 10) it can treat diseases or disorders characterized by increased PGC-1 expression or activity, e.g., diabetes or obesity; and 11) it can inhibit inflammation of muscle tissue.

Methods and assays for measuring each such biological activity are well-known in the art and representative, non-limiting embodiments are described in the Examples below. For example, evaluating the effect of various chemical agents on animal models of muscular dystrophy can be achieved by injecting mdx mice with an agent and evaluating therapeutic effects by comparing the morphological results between 3 regions of the *triangularis sterni* (TS); the caudal third of the muscle extending toward the xiphoid process, the middle third, and the cephalad third of the muscle since obvious differences between these regions exist in the extent of pathology and the muscle thickness in the TS of mdx mice. In another representative example, assays useful in measuring total mitochondrial oxygen consumption, uncoupled respiration, and total respiration are well known in the art, as described in St-Pierre et al. (2003) *J. Biol. Chem.* 278: 26597-26603.

As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO: 2, 4, 6, 8, 10, 12, 14, 16, 18, 20, 22, 24, 26, 28, or 30, or fragment thereof) amino acid residues to an amino acid sequence of SEQ ID NO: 2, 4, 6, 8, 10, 12, 14, 16, 18, 20, 22, 24, 26, 28, or 30, or fragment thereof, such that the protein or portion thereof modulates (e.g., enhance) one or more of the following biological activities: 1) it can modulate the expression of TNF-α, IL-6, IL-β, IL-10, TGF-β, ucp-1, cidea, dio2, pgc1β, err-α, pgc1α and its isoforms (e.g., pgc1α1), bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acyl-CoA-thioesterase 3; 2) it can increase cellular respiration (i.e., total and uncoupled respiration); 3) it can increase thermogenesis of adipose cells; 4) it can increase insulin sensitivity of adipose, muscle and/or hepatic cells; 5) it can decrease hepatosteatosis, obesity, type II diabetes, and/or appetite; 6) it can increase insulin secretion of pancreatic beta cells; 7) it can increase cardiac function to combat cardiac hypertrophy; 8) it can improve muscle hypoplasia; 9) it can reduce the growth and effects of obesity-associated cancer, cachexia, and anorexia; 10) it can treat diseases or disorders characterized by increased PGC-1 expression or activity, e.g., diabetes or obesity; and 11) it can inhibit inflammation of muscle tissue.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of SEQ ID NO: 2, 4, 6, 8, 10, 12, 14, 16, 18, 20, 22, 24, 26, 28, or 30, or fragment thereof, or a fragment thereof.

Portions of proteins encoded by the Metrnl and/or Metrn nucleic acid molecule of the invention are preferably biologically active portions of the Metrnl and/or Metrn protein. As used herein, the term "biologically active portion of Metrnl and/or Metrn" is intended to include a portion, e.g., a domain/motif, of Metrnl and/or Metrn that has one or more of the biological activities of the full-length Metrnl and/or Metrn protein, respectively.

Standard binding assays, e.g., immunoprecipitations and yeast two-hybrid assays, as described herein, or functional assays, e.g., RNAi or overexpression experiments, can be performed to determine the ability of an Metrnl and/or Metrn protein or a biologically active fragment thereof to maintain a biological activity of the full-length Metrnl and/or Metrn protein.

The invention further encompasses nucleic acid molecules that differ from the nucleotide sequence shown in SEQ ID NO: 1, 3, 5, 7, 9, 11, 13, 15, 17, 19, 21, 23, 25, 27, or 29, or fragment thereof due to degeneracy of the genetic code and thus encode the same Metrnl and/or Metrn protein as that encoded by the nucleotide sequence shown in SEQ ID NO: 1, 3, 5, 7, 9, 11, 13, 15, 17, 19, 21, 23, 25, 27, or 29, for fragment thereof. In another embodiment, an isolated nucleic acid molecule of the invention has a nucleotide sequence encoding a protein having an amino acid sequence shown in SEQ ID NO: 2, 4, 6, 8, 10, 12, 14, 16, 18, 20, 22, 24, 26, 28, or 30, or fragment thereof, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of SEQ ID NO: 2, 4, 6, 8, 10, 12, 14, 16, 18, 20, 22, 24, 26, 28, or 30, or fragment thereof, or a fragment thereof, or differs by at least 1, 2, 3, 5 or 10 amino acids but not more than 30, 20, 15 amino acids from SEQ ID NO: 2, 4, 6, 8, 10, 12, 14, 16, 18, 20, 22, 24, 26, 28, or 30. In another embodiment, a nucleic acid encoding an Metrnl and/or Metrn polypeptide consists of nucleic acid sequence encoding a portion of a full-length Metrnl and/or Metrn fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of Metrnl and/or Metrn may exist within a population (e.g., a mammalian population, e.g., a human population). Such genetic polymorphism in the Metrnl and/or Metrn gene may exist among individuals within a population due to natural allelic variation. As used herein, the terms "gene" and "recombinant gene" refer to nucleic acid molecules comprising an open reading frame encoding an Metrnl and/or Metrn protein, preferably a mammalian, e.g., human, Metrnl and/or Metrn protein. Such natural allelic variations can typically result in 1-5% variance in the nucleotide sequence of the Metrnl and/or Metrn gene. Any and all such nucleotide variations and resulting amino acid polymorphisms in Metrnl and/or Metrn that are the result of natural allelic variation and that do not alter the functional activity of Metrnl and/or Metrn are intended to be within the scope of the invention. Moreover, nucleic acid molecules encoding Metrnl and/or Metrn proteins from other species, and thus which have a nucleotide sequence which differs from the human or mouse sequences of SEQ ID NO: 1, 3, 5, 7, 15, 17, or 19, are intended to be within the scope of the invention. Nucleic acid molecules corresponding to natural allelic variants and homologues of the human or mouse Metrnl and/or Metrn cDNAs of the invention can be isolated based on their homology to the human or mouse Metrnl and/or Metrn nucleic acid sequences disclosed herein using the human or mouse cDNA, or a portion thereof, as a hybridization probe according to standard hybridization techniques under stringent hybridization conditions (as described herein).

In addition to naturally-occurring allelic variants of the Metrnl and/or Metrn sequence that may exist in the population, the skilled artisan will further appreciate that changes can be introduced by mutation into the nucleotide sequence of SEQ ID NO: 1, 3, 5, 7, 9, 11, 13, 15, 17, 19, 21, 23, 25, 27, or 29, or fragment thereof, thereby leading to changes in the amino acid sequence of the encoded Metrnl and/or Metrn protein, without altering the functional ability of the Metrnl and/or Metrn protein. For example, nucleotide substitutions leading to amino acid substitutions at "non-essential" amino acid residues can be made in the sequence of SEQ ID NO: 1, 3, 5, 7, 9, 11, 13, 15, 17, 19, 21, 23, 25, 27, or 29, or fragment thereof. A "non-essential" amino acid residue is a residue that can be altered from the wild-type sequence of Metrnl and/or Metrn (e.g., the sequence of SEQ ID NO: 2, 4, 6, 8, 10, 12, 14, 16, 18, 20, 22, 24, 26, 28, or 30, or fragment thereof) without significantly altering the activity of Metrnl and/or Metrn, whereas an "essential" amino acid residue is required for Metrnl and/or Metrn activity. Other amino acid residues, however, (e.g., those that are not conserved or only semi-conserved between mouse and human) may not be essential for activity and thus are likely to be amenable to alteration without altering Metrnl and/or Metrn activity. Furthermore, amino acid residues that are essential for Metrnl and/or Metrn functions related to thermogenesis and/or adipogenesis, but not essential for Metrnl and/or Metrn functions related to gluconeogenesis, are likely to be amenable to alteration.

Accordingly, another aspect of the invention pertains to nucleic acid molecules encoding Metrnl and/or Metrn proteins that contain changes in amino acid residues that are not essential for Metrnl and/or Metrn activity. Such Metrnl and/or Metrn proteins differ in amino acid sequence from SEQ ID NO: 2, 4, 6, 8, 10, 12, 14, 16, 18, 20, 22, 24, 26, 28, or 30, or fragment thereof, yet retain at least one of the Metrnl and/or Metrn activities described herein. In one embodiment, the isolated nucleic acid molecule comprises a nucleotide sequence encoding a protein, wherein the protein lacks one or more Metrnl and/or Metrn domains (e.g., a signal peptide).

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm.

Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a Metrnl and/or Metrn protein homologous to the protein of SEQ ID NO: 2, 4, 6, 8, 10, 12, 14, 16, 18, 20, 22, 24, 26, 28, or 30, or fragment thereof, can be created by introducing one or more nucleotide substitutions, additions or deletions into the nucleotide sequence of SEQ ID NO: 1, 3, 5, 7, 9, 11, 13, 15, 17, 19, 21, 23, 25, 27, or 29, or fragment thereof, or a homologous nucleotide sequence such that one or more amino acid substitutions, additions or deletions are introduced into the encoded protein. Mutations can be introduced into SEQ ID NO: 1, 3, 5, 7, 9, 11, 13, 15, 17, 19, 21, 23, 25, 27, or 29, or fragment thereof, or the homologous nucleotide sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), bet217-420ranched side chains (e.g., threonine, valine, isoleucine) and aromatic side chains (e.g., tyrosine, phenylalanine, tryptophan, histidine). Thus, a predicted nonessential amino acid residue in Metrnl and/or Metrn is preferably replaced with another amino acid residue from the same side chain family. Alternatively, in another embodiment, mutations can be introduced randomly along all or part of a Metrnl and/or Metrn coding sequence, such as by saturation mutagenesis, and the resultant mutants can be screened for a Metrnl and/or Metrn activity described herein to identify mutants that retain Metrnl and/or Metrn activity. Following mutagenesis of SEQ ID NO: 1, 3, 5, 7, 9, 11, 13, 15, 17, 19, 21, 23, 25, 27, or 29, or fragment thereof, the encoded protein can be expressed recombinantly (as described herein) and the activity of the protein can be determined using, for example, assays described herein.

Metrnl and/or Metrn levels may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, Metrnl and/or Metrn levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the Metrnl and/or Metrn mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding Metrnl and/or Metrn. Other suitable probes for use in the diagnostic assays of the invention are described herein. Hybridization of an mRNA with the probe indicates that Metrnl and/or Metrn is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the Metrnl and/or Metrn mRNA expression levels.

An alternative method for determining the Metrnl and/or Metrn mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self-sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the Metrnl and/or Metrn mRNA.

As an alternative to making determinations based on the absolute Metrnl and/or Metrn expression level, determinations may be based on the normalized Metrnl and/or Metrn expression level. Expression levels are normalized by correcting the absolute Metrnl and/or Metrn expression level by comparing its expression to the expression of a non-Metrnl and/or non-Metrn gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a Metrnl and/or Metrn protein can also be detected and/or quantified by detecting or quantifying the expressed polypeptide. The Metrnl and/or Metrn polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express Metrnl and/or Metrn.

In addition to the nucleic acid molecules encoding Metrnl and/or Metrn proteins described above, another aspect of the invention pertains to isolated nucleic acid molecules which are antisense thereto. An "antisense" nucleic acid comprises a nucleotide sequence which is complementary to a "sense" nucleic acid encoding a protein, i.e., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Metrnl and/or Metrn coding strand, or to only a portion thereof. In one embodiment, an antisense nucleic acid molecule is antisense to a "coding region" of the coding strand of a nucleotide sequence encoding Metrnl and/or Metrn. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding Metrnl and/or Metrn. The term "noncoding region" refers to 5' and 3' sequences which flank the coding region that are not translated into amino acids (i.e., also referred to as 5' and 3' untranslated regions).

In some embodiments, Metrnl and/or Metrn expression can be reduced using nucleic acid compositions described herein. For example, an "RNA interfering agent," as used herein, is defined as any agent which interferes with or inhibits expression of a target gene, e.g., Metrnl and/or Metrn, by RNA interference (RNAi). Such RNA interfering agents include, but are not limited to, nucleic acid molecules including RNA molecules which are homologous to the target gene or a fragment thereof, short interfering RNA (siRNA), and small molecules which interfere with or inhibit expression of a target gene by RNA interference (RNAi).

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) *J. of Virology* 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene or protein encoded by the target gene. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a subject having or at risk for a condition described herein mediated by Metrnl and/or Metrn, to inhibit expression of Metrnl and/or Metrn to thereby treat, prevent, or inhibit the condition in the subject.

II. Recombinant Expression Vectors and Host Cells

Another aspect of the invention pertains to the use of vectors, preferably expression vectors, containing a nucleic acid encoding Metrnl and/or Metrn (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising a Metrnl and/or Metrn nucleic acid molecule are used.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of Metrnl and/or Metrn in prokaryotic or eukaryotic cells. For example, Metrnl and/or Metrn can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the Metrnl and/or Metrn is cloned into a pGEX expression vector to create a vector encoding a fusion protein comprising, from the N-terminus to the C-terminus, and/or GST-thrombin cleavage site-Metrnl and/or -Metrn. The fusion protein can be purified by affinity chromatography using glutathione-agarose resin. Recombinant Metrnl and/or Metrn unfused to GST can be recovered by cleavage of the fusion protein with thrombin.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the Metrnl and/or Metrn expression vector is a yeast expression vector. Examples of vectors for expression in yeast *S. cerivisae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, Metrnl and/or Metrn can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a nucleic acid molecule of the invention cloned into the expression vector in an antisense orientation. That is, the DNA molecule is operatively linked to a regulatory sequence in a manner which allows for expression (by transcription of the DNA molecule) of an RNA molecule which is antisense to Metrnl and/or Metrn mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, Metrnl and/or Metrn protein can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

A cell culture includes host cells, media and other byproducts. Suitable media for cell culture are well known in the art. A Metrnl and/or Metrn polypeptide or fragment thereof, may be secreted and isolated from a mixture of cells and medium containing the polypeptide. Alternatively, a Metrnl and/or Metrn polypeptide or fragment thereof, may be retained cytoplasmically and the cells harvested, lysed and the protein or protein complex isolated. A Metrnl and/or Metrn polypeptide or fragment thereof, may be isolated from cell culture medium, host cells, or both using techniques known in the art for purifying proteins, including ion-exchange chromatography, gel filtration chromatography, ultrafiltration, electrophoresis, and inmmunoaffinity purification with antibodies specific for particular epitopes of Metrnl, Metrn. or a fragment thereof. In other embodiments, heterologous tags can be used for purification purposes (e.g., epitope tags and FC fusion tags), according to standards methods known in the art.

Thus, a nucleotide sequence encoding all or a selected portion of a Metrnl and/or Metrn polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant Metrnl and/or Metrn polypeptides, or fragments thereof, by microbial means or tissue-culture technology in accord with the subject invention.

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

In certain embodiments, the Metrnl and/or Metrn polypeptide, or fragment thereof, may be synthesized chemically, ribosomally in a cell free system, or ribosomally within a cell. Chemical synthesis may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding Metrnl and/or Metrn or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) Metrnl and/or Metrn protein. Accordingly, the invention further provides methods for producing Metrnl and/or Metrn protein using the host cells of the invention. In one embodiment, the method comprises culturing the host cell of invention (into which a recombinant expression vector encoding Metrnl has been introduced) in a suitable medium until Metrnl and/or Metrn is produced. In another embodiment, the method further comprises isolating Metrnl and/or Metrn from the medium or the host cell.

The host cells of the invention can also be used to produce nonhuman transgenic animals that, for example, overexpress Metrnl and/or Metrn, oversecrete Metrnl and/or Metrn, underexpress Metrnl and/or Metrn, or undersecrete Metrnl and/or Metrn. The nonhuman transgenic animals can be used in screening assays designed to identify agents or compounds, e.g., drugs, pharmaceuticals, etc., which are capable of ameliorating detrimental symptoms of selected disorders such as glucose homeostasis disorders, weight disorders, disorders associated with insufficient insulin activity, or inflammation-related muscle disorders. For example, in one embodiment, a host cell of the invention is a fertilized oocyte or an embryonic stem cell into which Metrnl- and/or Metrn-encoding sequences, or fragments thereof, have been introduced. Such host cells can then be used to create non-human transgenic animals in which exogenous Metrnl and/or Metrn sequences have been introduced into their genome or homologous recombinant animals in which endogenous Metrnl and/or Metrn sequences have been altered. Such animals are useful for studying the function and/or activity of Metrnl and/or Metrn, or fragments thereof, and for identifying and/or evaluating modulators of Metrnl and/or Metrn activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous Metrnl and/or Metrn gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acids encoding Metrnl and/or Metrn, or a fragment thereof, into the male pronuclei of a fertilized oocyte, e.g., by microinjection, retroviral infection, and allowing the oocyte to develop in a pseudopregnant female foster animal. The human Metrnl and/or Metrn cDNA sequence can be introduced as a transgene into the genome of a nonhuman animal. Alternatively, a nonhuman homologue of the human Metrnl and/or Metrn gene can be used as a transgene. Intronic sequences and polyadenylation signals can also be included in the transgene to increase the efficiency of expression of the transgene. A tissue-specific regulatory sequence(s) can be operably linked to the Metrnl and/or Metrn transgene to direct expression of Metrnl and/or Metrn protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the Metrnl and/or Metrn transgene in its genome and/or expression of Metrnl and/or Metrn mRNA in tissues or cells of the animals. A transgenic founder animal can then be used to breed additional animals carrying the transgene. Moreover, transgenic animals carrying a transgene encoding Metrnl and/or Metrn can further be bred to other transgenic animals carrying other transgenes.

In some embodiments, transgenic animals can be created in which Metrnl and/or Metrn expression and/or secretion is inhibited by introducing and expressing anti-Metrnl and/or anti-Metrn antisense nucleic acids into the genome of the animal.

To create a homologous recombinant animal, a vector is prepared which contains at least a portion of a Metrnl and/or Metrn gene into which a deletion, addition or substitution has been introduced to thereby alter, e.g., functionally disrupt, the Metrnl and/or Metrn gene. The Metrnl and/or Metrn gene can be a human gene, but more preferably, is a nonhuman homologue of a human Metrnl and/or Metrn gene. For example, a mouse Metrnl and/or Metrn gene can be used to construct a homologous recombination vector suitable for altering an endogenous Metrnl and/or Metrn gene, respectively, in the mouse genome. In a preferred embodiment, the vector is designed such that, upon homologous recombination, the endogenous Metrnl and/or Metrn gene is functionally disrupted (i.e., no longer encodes a functional protein; also referred to as a "knock out" vector). Alternatively, the vector can be designed such that, upon homologous recombination, the endogenous Metrnl and/or Metrn gene is mutated or otherwise altered but still encodes functional protein (e.g., the upstream regulatory region can be altered to thereby alter the expression of the endogenous Metrnl and/or Metrn protein). In the homologous recombination vector, the altered portion of the Metrnl and/or Metrn gene is flanked at its 5' and 3' ends by additional nucleic acid of the Metrnl and/or Metrn gene to allow for homologous recombination to occur between the exogenous Metrnl and/or Metrn gene carried by the vector and an endogenous Metrnl and/or Metrn gene in an embryonic stem cell. The additional flanking Metrnl and/or Metrn nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced Metrnl and/or Metrn gene has homologously recombined with the endogenous Metrnl and/or Metrn gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated Metrnl and/or Metrn Polypeptides, Anti-Metrnl Antibodies, and Anti-Metrn Antibodies The present invention provides soluble, purified and/or isolated forms of Metrnl and/or Metrn, or fragments thereof.

In one aspect, a Metrnl and/or Metrn polypeptide may comprise a full-length Metrnl and/or Metrn amino acid sequence or a full-length Metrnl and/or Metrn amino acid sequence with 1 to about 20 conservative amino acid substitutions Amino acid sequence of any Metrnl and/or Metrn polypeptide described herein can also be at least 50, 55, 60, 65, 70, 75, 80, 85, 90, 91, 92, 93, 94, 95, 96, 97, 98, 99, or 99.5% identical to a Metrnl and/or Metrn polypeptide sequence of interest, described herein, well known in the art, or a fragment thereof. In addition, any Metrnl and/or Metrn polypeptide, or fragment thereof, described herein has modulates (e.g., enhance) one or more of the following biological activities: 1) it can modulate the expression of TNF-α, IL-6, IL-β, IL-10, TGF-β, ucp-1, cidea, dio2, pgc1β, err-α, pgc1α and its isoforms (e.g., pgc1α1), bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acyl-CoA-thioesterase 3; 2) it can increase cellular respiration (i.e., total and uncoupled respiration); 3) it can increase thermogenesis of adipose cells; 4) it can increase insulin sensitivity of adipose, muscle and/or hepatic cells; 5) it can decrease hepatosteatosis, obesity, type II diabetes, and/or appetite; 6) it can increase insulin secretion of pancreatic beta cells; 7) it can increase cardiac function to combat cardiac hypertrophy; 8) it can improve muscle hypoplasia; 9) it can reduce the growth and effects of obesity-associated cancer, cachexia, and anorexia; 10) it can treat diseases or disorders characterized by increased PGC-1 expression or activity, .g., diabetes or obesity; and 11) it can inhibit inflammation of muscle tissue. In another aspect, the present invention contemplates a composition comprising an isolated Metrnl and/or Metrn polypeptide and less than about 25%, or alternatively 15%, or alternatively 5%, contaminating biological macromolecules or polypeptides.

The present invention further provides compositions related to producing, detecting, or characterizing a Metrnl and/or Metrn polypeptide, or fragment thereof, such as nucleic acids, vectors, host cells, and the like. Such compositions may serve as compounds that modulate a Metrnl and/or Metrn polypeptide's expression and/or activity, such as antisense nucleic acids.

In certain embodiments, a Metrnl and/or Metrn polypeptide of the invention may be a fusion protein containing a domain which increases its solubility and bioavailability and/or facilitates its purification, identification, detection, and/or structural characterization. In some embodiments, it may be useful to express Metrnl and/or Metrn fusion polypeptides in which the fusion partner enhances fusion protein stability in blood plasma and/or enhances systemic bioavailability. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, n Metrnl and/or Metrn polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In one embodiment, the linker is a linker described herein, e.g., a linker of at least 1, 2, 3, 4, 5, 6, 7, 8, 9, 10, 15, 20 or more amino acids. The linker can be, e.g., an unstructured recombinant polymer (URP), e.g., a URP that is 9, 10, 11, 12, 13, 14, 15, 20 amino acids in length, i.e., the linker has limited or lacks secondary structure, e.g., Chou-Fasman algorithm. An exemplary linker comprises (e.g., consists of) the amino acid sequence GGGGAGGGG (SEQ ID NO:15). In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, Metrnl and/or Metrn polypeptides, or fragments thereof, are fused to an antibody (e.g., IgG 1, IgG2, IgG3, IgG4) fragment (e.g., Fc polypeptides). Techniques for preparing these fusion proteins are known, and are described, for example, in WO 99/31241 and in Cosman et al. (2001) *Immunity* 14:123-133. Fusion to an Fc polypeptide offers the additional advantage of facilitating purification by affinity chromatography over Protein A or Protein G columns.

In still another embodiment, a Metrnl and/or Metrn polypeptide may be labeled with a fluorescent label to facilitate their detection, purification, or structural characterization. In an exemplary embodiment, a Metrnl and/or Metrn polypeptide of the invention may be fused to a heterologous polypeptide sequence which produces a detectable fluorescent signal, including, for example, green fluorescent protein (GFP), enhanced green fluorescent protein (EGFP), *Renilla Reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Another aspect of the invention pertains to the use of isolated Metrnl and/or Metrn proteins, and biologically active portions thereof, as well as peptide fragments suitable for use as immunogens to raise anti-Metrnl and/or anti-Metrn antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of Metrnl and/or Metrn protein in which the protein is separated from cellular components of the cells in which it is naturally or recombinantly produced. In one embodiment, the language "substantially free of cellular material" includes preparations of Metrnl and/or Metrn protein having less than about 30% (by dry weight) of non-Metrnl and/or non-Metrn protein (also referred to herein as a "contaminating protein"), more preferably less than about 20% of non-Metrnl and/or non-Metrn protein, still more preferably less than about 10% of non-Metrnl and/or non-Metrn protein, and most preferably less than about 5% non-Metrnl and/or non-Metrn protein. When the Metrnl and/or Metrn protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of Metrnl and/or Metrn protein in which the protein is separated from chemical precursors or other chemicals which are involved in the synthesis of the protein. In one embodiment, the language "substantially free of chemical precursors or other chemicals" includes preparations of Metrnl and/or Metrn protein having less than about 30% (by dry weight) of chemical precursors of non-Metrnl and/or non-Metrn chemicals, more preferably less than about 20% chemical precursors of non-Metrnl and/or non-Metrn chemicals, still more preferably less than about 10% chemical precursors of non-Metrnl and/or non-Metrn chemicals, and most preferably less than about 5% chemical precursors of non-Metrnl and/or non-Metrn chemicals. In preferred embodiments, isolated proteins or biologically active portions thereof lack contaminating proteins from the same animal from which the Metrnl and/or Metrn protein is derived. Typically, such proteins are produced by recombinant expression of, for example, a human Metrnl and/or Metrn protein in a nonhuman cell.

In preferred embodiments, the protein or portion thereof comprises an amino acid sequence which is sufficiently homologous to an amino acid sequence of SEQ ID NO: 2, 4, 6, 8, 10, 12, 14, 16, 18, 20, 22, 24, 26, 28, or 30, or fragment thereof, such that the protein or portion thereof maintains one or more of the following biological activities or, in complex, modulates (e.g., enhance) one or more of the following biological activities: 1) it can modulate the expression of TNF-α, IL-6, IL-β, IL-10, TGF-β, ucp-1, cidea, dio2, pgc1β, err-α, pgc1α and its isoforms (e.g., pgc1α1), bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acylCoA-thioesterase 3; 2) it can increase cellular respiration (i.e., total and uncoupled respiration); 3) it can increase thermogenesis of adipose cells; 4) it can increase insulin sensitivity of adipose, muscle and/or hepatic cells; 5) it can decrease hepatosteatosis, obesity, type II diabetes, and/or appetite; 6) it can increase insulin secretion of pancreatic beta cells; 7) it can increase cardiac function to combat cardiac hypertrophy; 8) it can improve muscle hypoplasia; 9) it can reduce the growth and effects of obesity-associated cancer, cachexia, and anorexia; 10) it can treat diseases or disorders characterized by increased PGC-1 expression or activity, e.g., diabetes or obesity; and 11) it can inhibit inflammation of muscle tissue. The portion of the protein is preferably a biologically active portion as described herein. In another preferred embodiment, the Metrnl and/or Metrn protein has an amino acid sequence shown in SEQ ID NO: 2, 4, 6, 8, 10, 12, 14, 16, 18, 20, 22, 24, 26, 28, or 30, or fragment thereof, respectively, or an amino acid sequence which is at least about 50%, 55%, 60%, 65%, 70%, 75%, 80%, 85%, 90%, 91%, 92%, 93%, 94%, 95%, 96%, 97%, 98%, 99% or more homologous to the amino acid sequence shown in SEQ ID NO: 2, 4, 6, 8, 10, 12, 14, 16, 18, 20, 22, 24, 26, 28, or 30, or fragment thereof. In yet another preferred embodiment, the Metrnl and/or Metrn protein has an amino acid sequence which is encoded by a nucleotide sequence which hybridizes, e.g., hybridizes under stringent conditions, to the nucleotide sequence of SEQ ID NO:1, 3, 5, 7, 9, 11, 13, 15, 17, 19, 21, 23, 25, 27, or 29, or fragment thereof, or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO: 1, 3, 5, 7, 9, 11, 13, 15, 17, 19, 21, 23, 25, 27, or 29, or fragment thereof. The preferred Metrnl and/or Metrn proteins of the present invention also preferably possess at least one of the Metrnl and/or Metrn biological activities, or activities associated with the complex, described herein. For example, a preferred Metrnl and/or Metrn protein of the present invention includes an amino acid sequence encoded by a nucleotide sequence which hybridizes, e.g., hybridizes under stringent conditions, to the nucleotide sequence of SEQ ID NO:1, 3, 5, 7, 9, 11, 13, 15, 17, 19, 21, 23, 25, 27, or 29, or fragment thereof and which can maintain one or more of the following biological activities or, in complex, modulates (e.g., enhance) one or more of the following biological activities: 1) it can modulate the expression of TNF-α, IL-6, IL-β, IL-10, TGF-β, ucp-1, cidea, dio2, pgc1β, err-α, pgc1α and its isoforms (e.g., pgc1α1), bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acylCoA-thioesterase 3; 2) it can increase cellular respiration (i.e., total and uncoupled respiration); 3) it can increase thermogenesis of adipose cells; 4) it can increase insulin sensitivity of adipose, muscle and/or hepatic cells; 5) it can decrease hepatosteatosis, obesity, type II diabetes, and/or appetite; 6) it can increase insulin secretion of pancreatic beta cells; 7) it can increase cardiac function to combat cardiac hypertrophy; 8) it can improve muscle hypoplasia; 9) it can reduce the growth and effects of obesity-associated cancer, cachexia, and anorexia; 10) it can treat diseases or disorders characterized by increased PGC-1 expression or activity, e.g., diabetes or obesity; and 11) it can inhibit inflammation of muscle tissue.

Biologically active portions of the Metrnl and/or Metrn protein include peptides comprising amino acid sequences derived from the amino acid sequence of the Metrnl and/or Metrn protein, e.g., the amino acid sequence shown in SEQ ID NO: 2, 4, 6, 8, 10, 12, 14, 16, 18, 20, 22, 24, 26, 28, or 30, or fragment thereof, or the amino acid sequence of a protein homologous to the Metrnl and/or Metrn protein, which include fewer amino acids than the full length Metrnl and/or Metrn protein or the full length protein which is homologous to the Metrnl and/or Metrn protein, and exhibit at least one activity of the Metrnl and/or Metrn protein, or complex thereof. Typically, biologically active portions (peptides, e.g., peptides which are, for example, 50, 55, 60, 65, 70, 75, 80, 85, 90, 95, 100 or more amino acids in length) comprise a domain or motif, e.g., the full-length protein minus the signal peptide). In a preferred embodiment, the biologically active portion of the protein which includes one or more the domains/motifs described herein can modulate brown fat gene expression programs and/or thermogenesis in adipose tissue (e.g., white fat cells) and/or inhibit inflammation in muscle tissue (e.g., skeletal muscle cells). Moreover, other biologically active portions, in which other regions of the protein are deleted, can be prepared by recombinant techniques and evaluated for one or more of the activities described herein. Preferably, the biologically active portions of the Metrnl and/or Metrn protein include one or more selected domains/motifs or portions thereof having biological activity. In one embodiment, a Metrnl and/or Metrn fragment consists of a portion of a full-length Metrnl and/or Metrn fragment of interest that is less than 300, 290, 280, 270, 260, 250, 240, 230, 220, 210, 200, 195, 190, 185, 180, 175, 170, 165, 160, 155, 150, 145, 140, 135, 130, 125, 120, 115, 110, 105, 100, 95, 90, 85, 80, 75, or 70 amino acids in length. Metrnl and/or Metrn proteins can be produced by recombinant DNA techniques.

For example, a nucleic acid molecule encoding the protein is cloned into an expression vector (as described above), the expression vector is introduced into a host cell (as described above) and the Metrnl and/or Metrn protein is expressed in the host cell. The Metrnl and/or Metrn protein can then be isolated from the cells by an appropriate purification scheme using standard protein purification techniques. Alternative to recombinant expression, a Metrnl and/or Metrn protein, polypeptide, or peptide can be synthesized chemically using standard peptide synthesis techniques. Moreover, native Metrnl and/or Metrn protein can be isolated from cells (e.g., skeletal muscle cells), for example using an anti-Metrnl antibody and/or an anti-Metrn antibody (described further below).

The invention also provides Metrnl and/or Metrn chimeric or fusion proteins. As used herein, a Metrnl and/or Metrn "chimeric protein" or "fusion protein" comprises a Metrnl and/or Metrn polypeptide operatively linked to a non-Metrnl and/or non-Metrn polypeptide. A "Metrnl or Metrn polypeptide" refers to a polypeptide having an amino acid sequence corresponding to Metrnl and/or Metrn, respectively, whereas a "non-Metrnl or non-Metrn polypeptide" refers to a polypeptide having an amino acid sequence corresponding to a protein which is not substantially homologous to the Metrnl and/or Metrn protein, respectively, e.g., a protein which is different from the Metrnl and/or Metrn protein and which is derived from the same or a different organism. Within the fusion protein, the term "operatively linked" is intended to indicate that the Metrnl and/or Metrn polypeptide and the non-Metrnl polypeptide and/or non-Metrn polypeptide are fused in-frame to each other. The non-Metrnl polypeptide and/or non-Metrn polypeptide can be fused to the N-terminus or C-terminus of the Metrnl polypeptide or Metrn polypeptide, respectively. For example, in one embodiment the fusion protein is a Metrnl-GST and/or Metrnl-Fc fusion protein in which the Metrnl sequences, respectively, are fused to the N-terminus of the GST or Fc sequences. Such fusion proteins can be made using Metrn polypeptides. Such fusion proteins can also facilitate the purification, expression, and/or bioavailability of recombinant Metrnl and/or Metrn. In another embodiment, the fusion protein is a Metrnl and/or Metrn protein containing a heterologous signal sequence at its C-terminus. In certain host cells (e.g., mammalian host cells), expression and/or secretion of Metrnl and/or Metrn can be increased through use of a heterologous signal sequence.

Preferably, a Metrnl and/or Metrn chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. *John Wiley & Sons*: 1992). Moreover, many expression vectors are commercially available that already encode a fusion moiety (e.g., a GST polypeptide). A Metrnl-encoding and/or Metrn-encoding nucleic acid can be cloned into such an expression vector such that the fusion moiety is linked in-frame to the Metrnl and/or Metrn protein.

The present invention also pertains to homologues of the Metrnl and/or Metrn proteins which function as either a Metrnl and/or Metrn agonist (mimetic) or a Metrnl and/or Metrn antagonist. In a preferred embodiment, the Metrnl and/or Metrn agonists and antagonists stimulate or inhibit, respectively, a subset of the biological activities of the naturally occurring form of the Metrnl and/or Metrn protein, respectively. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the Metrnl protein.

Homologues of the Metrnl and/or Metrn protein can be generated by mutagenesis, e.g., discrete point mutation or truncation of the Metrnl and/or Metrn protein, respectively. As used herein, the term "homologue" refers to a variant form of the Metrnl and/or Metrn protein which acts as an agonist or antagonist of the activity of the Metrnl and/or Metrn protein, respectively. An agonist of the Metrnl and/or Metrn protein can retain substantially the same, or a subset, of the biological activities of the Metrnl and/or Metrn protein, respectively. An antagonist of the Metrnl and/or Metrn protein can inhibit one or more of the activities of the naturally occurring form of the Metrnl and/or Metrn protein, by, for example, competitively binding to a downstream or upstream member of the Metrnl and/or Metrn cascade which includes the Metrnl and/or Metrn protein. Thus, the mammalian Metrnl and/or Metrn protein and homologues thereof of the present invention can be, for example, either positive or negative regulators of adipocyte differentiation and/or thermogenesis in brown adipocytes.

In an alternative embodiment, homologues of the Metrnl and/or Metrn protein can be identified by screening combinatorial libraries of mutants, e.g., truncation mutants, of the Metrnl and/or Metrn protein for Metrnl and/or Metrn protein agonist or antagonist activity. In one embodiment, a variegated library of Metrnl and/or Metrn variants is generated by combinatorial mutagenesis at the nucleic acid level and is encoded by a variegated gene library. A variegated library of Metrnl and/or Metrn variants can be produced by, for example, enzymatically ligating a mixture of synthetic oligonucleotides into gene sequences such that a degenerate set of potential Metrnl and/or Metrn sequences is expressible as individual polypeptides, or alternatively, as a set of larger fusion proteins (e.g., for phage display) containing the set of Metrnl and/or Metrn sequences therein. There are a variety of methods which can be used to produce libraries of potential Metrnl homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Metrnl and/or Metrn sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the Metrnl and/or Metrn protein coding can be used to generate a variegated population of Metrnl and/or Metrn fragments for screening and subsequent selection of homologues of a Metrnl and/or Metrn protein. In one embodiment, a library of coding sequence fragments can be generated by treating a double stranded PCR fragment of a Metrnl and/or Metrn coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the Metrnl and/or Metrn protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Metrnl and/or Metrn homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify Metrnl and/or Metrn homologues (Arkin and Youvan (1992) *Proc. Natl. Acad. Sci. USA* 89:7811-7815; Delagrave et al. (1993) *Protein Engineering* 6(3):327-331).

In another aspect, an isolated Metrnl and/or Metrn protein, or a fragment thereof, can be used as an immunogen to generate antibodies that bind Metrnl and/or Metrn, respectively, or the complex thereof, using standard techniques for polyclonal and monoclonal antibody preparation. The full-length Metrnl and/or Metrn protein can be used or, alternatively, antigenic peptide fragments of Metrnl and/or Metrn, or peptides in complex, can be used as immunogens. A Metrnl and/or Metrn immunogen typically is used to prepare antibodies by immunizing a suitable subject, (e.g., rabbit, goat, mouse or other mammal) with the immunogen. An appropriate immunogenic preparation can contain, for example, recombinantly expressed Metrnl and/or Metrn protein or a chemically synthesized Metrnl and/or Metrn peptide. The preparation can further include an adjuvant, such as Freund's complete or incomplete adjuvant, or similar immunostimulatory agent. Immunization of a suitable subject with an immunogenic Metrnl and/or Metrn preparation induces a polyclonal anti-Metrnl and/or anti-Metrn antibody response.

Accordingly, another aspect of the invention pertains to the use of anti-Metrnl antibodies and/or anti-Metrn antibodies. The term "antibody" as used herein refers to immunoglobulin molecules and immunologically active portions of immunoglobulin molecules, i.e., molecules that contain an antigen binding site which specifically binds (immunoreacts with) an antigen, such as Metrnl and/or Metrn. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind Metrnl and/or Metrn. The term "monoclonal antibody" or "monoclonal antibody composition", as used herein, refers to a population of antibody molecules that contain only one species of an antigen binding site capable of immunoreacting with a particular epitope of Metrnl and/or Metrn. A monoclonal antibody composition thus typically displays a single binding affinity for a particular Metrnl and/or Metrn protein with which it immunoreacts.

Polyclonal anti-Metrnl antibodies and/or anti-Metrn antibodies can be prepared as described above by immunizing a suitable subject with a Metrnl and/or Metrn immunogen, or fragment thereof. The anti-Metrnl antibody and/or anti-Metrn antibody titer in the immunized subject can be monitored over time by standard techniques, such as with an enzyme linked immunosorbent assay (ELISA) using immobilized Metrnl and/or Metrn. If desired, the antibody molecules directed against Metrnl and/or Metrn can be isolated from the mammal (e.g., from the blood) and further purified by well-known techniques, such as protein A chromatography to obtain the IgG fraction. At an appropriate time after immunization, i.e., when the anti-Metrnl antibody and/or anti-Metrn antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a Metrnl and/or Metrn immunogen as described above, and the culture supernatants of the resulting hybridoma cells are screened to identify a hybridoma producing a monoclonal antibody that binds Metrnl and/or Metrn.

Any of the many well-known protocols used for fusing lymphocytes and immortalized cell lines can be applied for the purpose of generating an anti-Metrnl monoclonal antibody and/or anti-Metrn monoclonal antibody (see, i.e., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Metrnl and/or Metrn, i.e., using a standard ELISA assay.

As an alternative to preparing monoclonal antibody-secreting hybridomas, a monoclonal anti-Metrnl antibody and/or monoclonal anti-Metrn antibody can be identified and isolated by screening a recombinant combinatorial immunoglobulin library (e.g., an antibody phage display library) with Metrnl and/or Metrn, respectively, to thereby isolate immunoglobulin library members that bind Metrnl and/or Metrn. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-Metrnl antibodies and/or anti-Metrn antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-Metrnl antibody and/or anti-Metrn antibody (e.g., monoclonal antibody) can be used to isolate Metrnl and/or Metrn by standard techniques, such as affinity chromatography or immunoprecipitation. An anti-Metrnl antibody and/or anti-Metrn antibody can facilitate the purification of natural Metrnl and/or Metrn from cells and of recombinantly produced Metrnl and/or Metrn expressed in host cells. Moreover, an anti-Metrnl antibody and/or anti-Metrn antibody can be used to detect Metrnl and/or Metrn protein (e.g., in a cellular lysate or cell supernatant) in order to evaluate the abundance and pattern of expression of the Metrnl and/or Metrn protein. Anti-Metrnl antibodies and/or anti-Metrn antibodies can be used to monitor protein levels in a cell or tissue, e.g., adipose cells or tissue, as part of a clinical testing procedure, e.g., in order to monitor a safe dosage of an uncoupling agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

In vivo techniques for detection of Metrnl and/or Metrn protein include introducing into a subject a labeled antibody directed against the protein. For example, the antibody can be labeled with a radioactive marker whose presence and location in a subject can be detected by standard imaging techniques.

IV. Identification of Compounds that Modulate Metrnl and/or Metrn

The Metrnl and/or Metrn nucleic acid and polypeptide molecules described herein may be used to design modulators of one or more of biological activities of the complex or complex polypeptides. In particular, information useful for the design of therapeutic and diagnostic molecules, including, for example, the protein domain, structural information, and the like for polypeptides of the invention is now available or attainable as a result of the ability to prepare, purify and characterize the complexes and complex polypeptides, and domains, fragments, variants and derivatives thereof.

In one aspect, modulators, inhibitors, or antagonists against the polypeptides of the invention, biological complexes containing them, or orthologs thereof, may be used to treat any disease or other treatable condition of a patient (including humans and animals), including, for example, metabolic disorders.

Modulators of Metrnl and/or Metrn nucleic acid and polypeptide molecules, may be identified and developed as set forth below using techniques and methods known to those of skill in the art. The modulators of the invention may be employed, for instance, to inhibit and treat Metrnl-mediated and/or Metrn-mediated diseases or disorders. The modulators of the invention may elicit a change in one or more of the following activities: (a) a change in the level and/or rate of formation of an Metrnl-receptor and/or Metrn-receptor complex, (b) a change in the activity of a Metrnl and/or Metrn nucleic acid and/or polypeptide, (c) a change in the stability of a Metrnl and/or Metrn nucleic acid and/or polypeptide, (d) a change in the conformation of a Metrnl and/or Metrn nucleic acid and/or polypeptide, or (e) a change in the activity of at least one polypeptide contained in a Metrnl and/or Metrn complex (e.g., a receptor for secreted Metrnl and/or Metrn). A number of methods for identifying a molecule which modulates a Metrnl and/or Metrn nucleic acid and/or polypeptide are known in the art. For example, in one such method, a Metrnl and/or Metrn nucleic acid and/or polypeptide, is contacted with a test compound, and the activity of the Metrnl and/or Metrn nucleic acid and/or polypeptide is determined in the presence of the test compound, wherein a change in the activity of the Metrnl and/or Metrn nucleic acid and/or polypeptide in the presence of the compound as compared to the activity in the absence of the compound (or in the presence of a control compound) indicates that the test compound modulates the activity of the Metrnl and/or Metrn nucleic acid and/or polypeptide.

Compounds to be tested for their ability to act as modulators of Metrnl and/or Metrn nucleic acids and/or polypeptides, can be produced, for example, by bacteria, yeast or other organisms (e.g. natural products), produced chemically (e.g. small molecules, including peptidomimetics), or produced recombinantly. Compounds for use with the above-described methods may be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide. In some embodiments, said polynucleotide is an antisense nucleic acid. In other embodiments, said polynucleotide is an siRNA. In certain embodiments, the compound comprises a biologically active fragment of a Metrnl and/or Metrn polypeptide (e.g., a dominant negative form that binds to, but does not activate, a Metrnl receptor and/or Metrn receptor).

A variety of assay formats will suffice and, in light of the present disclosure, those not expressly described herein may nevertheless be comprehended by one of ordinary skill in the art based on the teachings herein. Assay formats for analyzing Metrnl-receptor and/or Metrn-receptor complex formation and/or activity of a Metrnl and/or Metrn nucleic acid and/or polypeptide, may be generated in many different forms, and include assays based on cell-free systems, e.g. purified proteins or cell lysates, as well as cell-based assays which utilize intact cells. Simple binding assays can also be used to detect agents which modulate a Metrnl and/or Metrn, for example, by enhancing the formation of a Metrnl complex and/or Metrn complex, by enhancing the binding of Metrnl and/or Metrn to a substrate, and/or by enhancing the binding of a Metrnl and/or Metrn polypeptide to a substrate. Another example of an assay useful for identifying a modulator of Metrnl and/or Metrn is a competitive assay that combines one or more Metrnl and/or Metrn polypeptides with a potential modulator, such as, for example, polypeptides, nucleic acids, natural substrates or ligands, or substrate or ligand mimetics, under appropriate conditions for a competitive inhibition assay. Metrnl and/or Metrn polypeptides can be labeled, such as by radioactivity or a colorimetric compound, such that Metrnl-receptor complex and/or Metrn-receptor formation and/or activity can be determined accurately to assess the effectiveness of the potential modulator.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. Assays may also employ any of the methods for isolating, preparing and detecting Metrnl and/or Metrn, or complex polypeptides, as described above.

Complex formation between a Metrnl polypeptide and/or Metrn, or fragment thereof, and a binding partner (e.g., Metrnl receptor and/or Metrn receptor) may be detected by a variety of methods. Modulation of the complex's formation may be quantified using, for example, detectably labeled proteins such as radiolabeled, fluorescently labeled, or enzymatically labeled polypeptides or binding partners, by immunoassay, or by chromatographic detection. Methods of isolating and identifying Metrnl-receptor complexes and/or Metrn-receptor complexes described above may be incorporated into the detection methods.

In certain embodiments, it may be desirable to immobilize a Metrnl polypeptide and/or Metrn polypeptide to facilitate separation of Metrnl complexes and/or Metrn complexes from uncomplexed forms of one or both of the proteins, as well as to accommodate automation of the assay. Binding of a Metrnl polypeptide and/or Metrn polypeptide to a binding partner may be accomplished in any vessel suitable for containing the reactants. Examples include microtiter plates, test tubes, and micro-centrifuge tubes. In one embodiment, a fusion protein may be provided which adds a domain that allows the protein to be bound to a matrix. For example, glutathione-S-transferase/polypeptide (GST/polypeptide) fusion proteins may be adsorbed onto glutathione sepharose beads (Sigma Chemical, St. Louis, Mo.) or glutathione derivatized microtiter plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes may be dissociated from the matrix, separated by SDS-PAGE, and the level of Metrnl polypeptides and/or Metrn polypeptides found in the bead fraction quantified from the gel using standard electrophoretic techniques such as described in the appended examples.

Other techniques for immobilizing proteins on matrices are also available for use in the subject assay. For instance, a Metrnl polypeptide and/or Metrn polypeptide may be immobilized utilizing conjugation of biotin and streptavidin. For instance, biotinylated polypeptide molecules may be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptide may be derivatized to the wells of the plate, and polypeptide trapped in the wells by antibody conjugation. As above, preparations of a binding partner and a test compound are incubated in the polypeptide presenting wells of the plate, and the amount of complex trapped in the well may be quantified. Exemplary methods for detecting such complexes, in addition to those described above for the GST-immobilized complexes, include immunodetection of complexes using antibodies reactive with the binding partner, or which are reactive with the Metrnl polypeptide and/or Metrn polypeptide and compete with the binding partner; as well as enzyme-linked assays which rely on detecting an enzymatic activity associated with the binding partner, either intrinsic or extrinsic activity. In the instance of the latter, the enzyme may be chemically conjugated or provided as a fusion protein with the binding partner. To illustrate, the binding partner may be chemically cross-linked or genetically fused with horseradish peroxidase, and the amount of Metrnl polypeptide and/or Metrn polyeptdie trapped in the Metrnl complex and/or Metrn complex, respectively, may be assessed with a chromogenic substrate of the enzyme, e.g. 3,3'-diamino-benzadine terahydrochloride or 4-chloro-1-napthol. Likewise, a fusion protein comprising the Metrnl polypeptide and/or Metrn polypeptide and glutathione-S-transferase may be provided, and Metrnl and/or Metrn complex formation quantified by detecting the GST activity using 1-chloro-2,4-dinitrobenzene (Habig et al (1974) J Biol Chem 249:7130).

Antibodies against the Metrnl and/or Metrn polypeptide can be used for immunodetection purposes. Alternatively, the Metrnl and/or Metrn polypeptide to be detected may be "epitope-tagged" in the form of a fusion protein that includes, in addition to the polypeptide sequence, a second polypeptide for which antibodies are readily available (e.g. from commercial sources). For instance, the GST fusion proteins described above may also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, N.J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system may be derived to favor discovery of modulators of particular intermediate states of the protein-protein interaction. For instance, a reconstituted protein assay may be carried out both in the presence and absence of a candidate agent, thereby allowing detection of a modulator of a given protein-substrate, protein-protein, or nucleic acid-protein interaction.

Assaying biological activity resulting from a given protein-substrate, protein-protein or nucleic acid-protein interaction, in the presence and absence of a candidate modulator, may be accomplished in any vessel suitable for containing the reactants. Examples include microtiter plates, test tubes, and micro-centrifuge tubes.

In yet another embodiment, a Metrnl and/or Metrn polypeptide may be used to generate a two-hybrid or interaction trap assay (see also, U.S. Pat. No. 5,283,317; Zervos et al. (1993) Cell 72:223-232; Madura et al. (1993) J. Biol Chem 268:12046-12054; Bartel et al. (1993) Biotechniques 14:920-924; and Iwabuchi et al. (1993) Oncogene 8:1693-1696), for subsequently detecting agents which disrupt binding of the interaction components to one another.

In particular, the method makes use of chimeric genes which express hybrid proteins. To illustrate, a first hybrid gene comprises the coding sequence for a DN217-420inding domain of a transcriptional activator may be fused in frame to the coding sequence for a "bait" protein, e.g., a Metrnl and/or Metrn polypeptide of sufficient length to bind to a potential interacting protein. The second hybrid protein encodes a transcriptional activation domain fused in frame to a gene encoding a "fish" protein, e.g., a potential interacting protein of sufficient length to interact with the protein-protein interaction component polypeptide portion of the bait fusion protein. If the bait and fish proteins are able to interact, e.g., form a protein-protein interaction component complex, they bring into close proximity the two domains of the transcriptional activator. This proximity causes transcription of a reporter gene which is operably linked to a transcriptional regulatory site responsive to the transcriptional activator, and expression of the reporter gene may be detected and used to score for the interaction of the bait and fish proteins. The host cell also contains a first chimeric gene which is capable of being expressed in the host cell. The gene encodes a chimeric protein, which comprises (a) a DNA binding domain that recognizes the responsive element on the reporter gene in the host cell, and (b) a bait protein (e.g., a Metrnl and/or Metrn polypeptide). A second chimeric gene is also provided which is capable of being expressed in the host cell, and encodes the "fish" fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

The DNA binding domain of the first hybrid protein and the transcriptional activation domain of the second hybrid protein may be derived from transcriptional activators having separable DNA binding and transcriptional activation domains. For instance, these separate DNA binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally-inert DNA binding domains may be used in the subject constructs; such as domains of ACE1, λcI, lac repressor, jun or fos. In another embodiment, the DNA binding domain and the transcriptional activation domain may be from different proteins. The use of a LexA DNA binding domain provides certain advantages. For example, in yeast, the LexA moiety contains no activation function and has no known effect on transcription of yeast genes. In addition, use of LexA allows control over the sensitivity of the assay to the level of interaction (see, for example, PCT publication WO 94/10300).

In certain embodiments, any enzymatic activity associated with the bait or fish proteins is inactivated, e.g., dominant negative or other mutants of a protein-protein interaction component can be used.

Continuing with the illustrative example, formation of a complex between the bait and fish fusion proteins in the host cell, causes the activation domain to activate transcription of the reporter gene. The method is carried out by introducing the first chimeric gene and the second chimeric gene into the host cell, and subjecting that cell to conditions under which the bait and fish fusion proteins and are expressed in sufficient quantity for the reporter gene to be activated. The formation of a complex results in a detectable signal produced by the expression of the reporter gene.

In still further embodiments, the Metrnl and/or Metrn polypeptide, or complexes thereof, of interest may be generated in whole cells, taking advantage of cell culture techniques to support the subject assay. For example, the Metrnl and/or Metrn polypeptide, or complexes thereof, may be constituted in a prokaryotic or eukaryotic cell culture system. Advantages to generating the Metrnl and/or Metrn polypeptide, or complexes thereof, in an intact cell includes the ability to screen for modulators of the level and/or activity of the Metrnl and/or Metrn polypeptides, or complexes thereof, which are functional in an environment more closely approximating that which therapeutic use of the modulator would require, including the ability of the agent to gain entry into the cell. Furthermore, certain of the in vivo embodiments of the assay are amenable to high through-put analysis of candidate agents.

The Metrnl and/or Metrn nucleic acids and/or polypeptide can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high throughput analysis in that proliferation of the cell can provide a simple measure of the protein-protein interaction.

The amount of transcription from the reporter gene may be measured using any method known to those of skill in the art to be suitable. For example, specific mRNA expression may be detected using Northern blots or specific protein product may be identified by a characteristic stain, western blots or an intrinsic activity. In certain embodiments, the product of the reporter gene is detected by an intrinsic activity associated with that product. For instance, the reporter gene may encode a gene product that, by enzymatic activity, gives rise to a detection signal based on color, fluorescence, or luminescence.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target. Accordingly, potential modulators of Metrnl and/or Metrn may be detected in a cell-free assay generated by constitution of a functional Metrnl and/or Metrn in a cell lysate. In an alternate format, the assay can be derived as a reconstituted protein mixture which, as described below, offers a number of benefits over lysate-based assays.

The activity of a Metrnl and/or Metrn polypeptide may be identified and/or assayed using a variety of methods well known to the skilled artisan. For example, the activity of a Metrnl and/or Metrn nucleic acid and/or polypeptide may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes.

In other embodiments, the biological activity of a Metrnl and/or Metrn nucleic acid and/or polypeptide may be assessed by monitoring changes in the phenotype of a targeted cell. For example, the detection means can include a reporter gene construct which includes a transcriptional regulatory element that is dependent in some form on the level and/or activity of a Metrnl and/or Metrn nucleic acid and/or polypeptide. The Metrnl and/or Metrn nucleic acid and/or polypeptide may be provided as a fusion protein with a domain that binds to a DNA element of a reporter gene construct. The added domain of the fusion protein can be one which, through its DNA binding ability, increases or decreases transcription of the reporter gene. Whichever the case may be, its presence in the fusion protein renders it responsive to a Metrnl and/or Metrn nucleic acid and/or polypeptide. Accordingly, the level of expression of the reporter gene will vary with the level of expression of a Metrnl and/or Metrn nucleic acid and/or polypeptide.

Moreover, in the whole cell embodiments of the subject assay, the reporter gene construct can provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene can be an enzyme which confers resistance to an antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of a Metrnl and/or Metrn nucleic acid and/or polypeptide present in the cell. Such embodiments of the subject assay are particularly amenable to high through-put analysis in that proliferation of the cell can provide a simple measure of inhibition of the Metrnl and/or Metrn nucleic acid and/or polypeptide.

V. Methods of the Invention

The methods of the invention relate to the expression and/or activity of Metrnl and/or Metrn sufficient to modulate (e.g., induce or repress) brown fat gene expression programs (e.g., one or more genes indicative of brown fat relative to white fat) and/or thermogenesis in adipose tissue and inflammation in muscle tissue, wherein increases in Metrnl and/or Metrn expression and/or activity promote brown fat gene expression and/or thermogenesis in adipose tissue so as to increase energy expenditure and can therefore be used to treat metabolic disorders such as obesity, cardiac hypertrophy, type II diabetes, and in patients in need of more exercise; and, wherein decreases in Metrnl and/or Metrn expression and/or activity promote brown fat gene expression and/or thermogenesis in adipose tissue so as to decrease energy expenditure and can therefore be used to treat the effects of such conditions as cachexia, anorexia, and obesity-associated cancer. Similarly, increases in Metrnl and/or Metrn expression and/or activity inhibit inflammation in muscle tissue (e.g., skeletal muscle cells) and thus are useful in treating inflammation-related muscle disorders.

The invention also relates to methods for increasing energy expenditure in a mammal comprising inducing expression and/or activity of Metrnl and/or Metrn sufficient to activate a brown fat gene expression program in the mammal, wherein the differentiated brown fat cells promote energy expenditure thereby increasing energy expenditure in the mammal.

The term "sufficient to activate" is intended to encompass any increase in expression and/or activity of Metrnl and/or Metrn that promotes, activates, stimulates, enhances, or results in brown fat gene expression program induction.

In another aspect, the invention relates to methods for treating metabolic disorders or muscle inflammation disorders in a subject comprising administering to the subject an agent that induces expression and/or activity of Metrnl and/or Metrn, wherein expression and/or activity of Metrnl and/or Metrn increases respiration and energy expenditure and/or decreases muscle cell inflammation to thereby treat the metabolic disorder or muscle inflammation disorder. In one embodiment, total respiration is increased following the expression and/or activity of Metrnl and/or Metrn. In another embodiment, uncoupled respiration is increased following the expression and/or activity of Metrnl and/or Metrn. Uncoupled respiration dissipates heat and thereby increases energy expenditure in the subject.

As used herein, the term "agent" and "therapeutic agent" is defined broadly as anything that cells from a subject having a metabolic disorder may be exposed to in a therapeutic protocol. In one embodiment, the agent is a recombinant Metrnl and/or Metrn protein, or fragment thereof, or nucleic acid molecule encoding such a polypeptide. In some embodiments, Metrnl and/or Metrn proteins or nucleic acid molecules encoding same can serve to enhance Metrnl and/or Metrn protein function (e.g., overexpressed Metrnl and/or Metrn, oversecreted Metrnl and/or Metrn, plasma stabilized Metrnl and/or Metrn, etc.), whereas in other embodiments, Metrnl and/or Metrn proteins or nucleic acid molecules encoding same can serve to inhibit Metrnl and/or Metrn protein function (e.g., non-activating Metrnl and/or Metrn polypeptides that bind Metrnl and/or Metrn receptors but do not activate receptor signaling, dominant-negative Metrnl and/or Metrn polypeptides that cannot bind Metrnl and/or Metrn receptors or binding partners). In another embodiment, the agent is an anti-sense nucleic acid molecule having a sequence complementary to Metrnl and/or Metrn (e.g., an RNAi, siRNA, or other RNA inhibiting nucleic acid molecule). In still another embodiment, antibody reagents can be used to sequester Metrnl and/or Metrn from functionally activating Metrnl and/or Metrn receptors or binding partners.

The term "administering" is intended to include routes of administration which allow the agent to perform its intended function of modulating (e.g., increasing or decreasing) expression and/or activity of Metrnl and/or Metrn. Examples of routes of administration which can be used include injection (subcutaneous, intravenous, parenterally, intraperitoneally, intrathecal, etc., such as in a subcutaneous injection into white fate depots), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. Further the agent may be coadministered with a pharmaceutically acceptable carrier. The agent also may be administered as a prodrug, which is converted to its active form in vivo. The agent may also be administered in combination with one or more additional therapeutic agent(s) (e.g., before, after or simultaneously therewith).

The term "effective amount" of an agent that induces expression and/or activity of Metrnl and/or Metrn is that amount necessary or sufficient to modulate (e.g., increase or decrease) expression and/or activity of Metrnl and/or Metrn in the subject or population of subjects. The effective amount can vary depending on such factors as the type of therapeutic agent(s) employed, the size of the subject, or the severity of the disorder.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to, the pharmacodynamic characteristics of the particular respiration uncoupling agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any particular respiration agent to treat a metabolic disorder or muscle inflammation disorder can be monitored by comparing two or more samples obtained from a subject undergoing anti-obesity, obesity-related, or muscle inflammation disorder treatment. In general, it is preferable to obtain a first sample from the subject prior to beginning therapy and one or more samples during treatment. In such a use, a baseline of expression of cells from subjects with the disorder prior to therapy is determined and then changes in the baseline state of expression of cells from subjects with the disorder is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with the disorder is increasing or decreasing.

Another aspect of the invention relates to a method for inducing a brown fat gene expression program in adipose tissue (e.g., white fat cells and preadipocytes), fibroblasts, and the like of a mammal comprising expressing Metrnl and/or Metrn nucleic acid and/or polypeptide molecules in a mammal and monitoring brown fat gene expression or downstream effects of brown fat cells in the mammal Increased brown adipose tissue in the mammal will warm up the body and blood of the mammal resulting in an increased energy expenditure from the cells. The increased energy expenditure will increase the metabolic rate of the subject and may be used for the treatment and/or prevention of obesity and obesity related disorders. The induction of brown fat cells may be monitored by analyzing 1) the expression of TNF-α, IL-6, IL-β, IL-10, TGF-β, ucp-1, cidea, dio2, pgc1β, err-α, pgc1α and its isoforms (e.g., pgc1α1), bmp8b, adiponectin (adipoq), adipsin, otopetrin, type II deiodinase, cig30, ppar gamma 2, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, and acylCoA-thioesterase 3; 2) increases in cellular respiration (i.e., total and uncoupled respiration); 3) increases in thermogenesis of adipose cells; 4) increases in insulin sensitivity of adipose, muscle and/or hepatic cells; 5) decreases in hepatosteatosis, obesity, type II diabetes, and/or appetite; 6) increases in insulin secretion of pancreatic beta cells; 7) increases in cardiac function to combat cardiac hypertrophy; 8) improved muscle hypoplasia; 9) reduction in growth and effects of obesity-associated cancer, cachexia, and anorexia; and/or 10) treatment of diseases or disorders characterized by increased PGC-1 expression or activity, e.g., diabetes or obesity. Alternatively, anti-Metrnl agents and/or anti-Metrn agents, such as antisense or antibody agents, can be used to inhibit a brown fat gene expression program in a mammal to thereby cause the opposite result.

Still another aspect of the invention relates to a method for inhibiting muscle inflammation in a mammal comprising expressing Metrnl and/or Metrn nucleic acid and/or polypeptide molecules in a mammal and monitoring muscle inflammation in the mammal Alternatively, anti-Metrnl agents and/or anti-Metrn agents, such as antisense or antibody agents, can be used to promote muscle inflammation.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Feigner, et al., Ann NY Acad Sci 126-139, 1995). Formulation of DNA, e.g. with various lipid or liposome materials, may then be effected using known methods and materials and delivered to the recipient mammal See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Feigner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant Metrnl and/or Metrn polypeptides, and fragments thereof, can be administered to subjects. In some embodiments, fusion proteins can be constructed and administered which have enhanced biological properties (e.g., Fc fusion proteins discussed above). In addition, the Metrnl and/or Metrn polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

VI. Pharmaceutical Compositions

In another aspect, the present invention provides pharmaceutically acceptable compositions which comprise a therapeutically-effective amount of an agent that modulates (e.g., increases or decreases) Metrnl and/or Metrn expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., enhances) Metrnl and/or Metrn expression and/or activity, or expression and/or activity of the complex, or composition comprising an agent that modulates (e.g., enhances) Metrnl and/or Metrn expression and/or activity, or expression and/or activity of the complex, which is effective for producing some desired therapeutic effect, e.g., weight loss, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., enhances) Metrnl and/or Metrn expression and/or activity, or expression and/or activity of the complex encompassed by the invention. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., enhances) Metrnl and/or Metrn expression and/or activity, or expression and/or activity of the complex. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., increases or decreases) Metrnl and/or Metrn expression and/or activity, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and *acacia* or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and *acacia*) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or *acacia*; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., increases or decreases) Metrnl and/or Metrn expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., increases or decreases) Metrnl and/or Metrn expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., increases or decreases) Metrnl and/or Metrn expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., increases or decreases) Metrnl and/or Metrn expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

EXEMPLIFICATION

This invention is further illustrated by the following examples, which should not be construed as limiting.

Example 1: Materials and *Methods for Examples 2-4*

A. Adenoviral Vectors

The Metrnl expression vector was purchased from OriGene. PCR primers were designed to remove the stop codon and sub-clone it into the pENTR1a vector (Invitrogen). The pENTR vector containing Metrnl cDNA was recombined into the pAd-CMV-DEST-V5 adenoviral vector (Invitrogen) to obtain Metrnl with a C-terminal V5 epitope tag. The sequence of the murine Metrnl cDNA (light grey shading) from the pAD/CMV/V5-DEST adenoviral vector, in which the stop codon was removed and a C-terminal V5 epitope tag (dark grey shading) was added, has the following sequence:

```
ATGCGGGGTGCGGTGTGGGCGGCCCGGAGGCGCGCGGGGCAGCAGTGGCCTCGGTCCCCGGGCCCTGGGC

CGGGTCCGCCCCCGCCGCCACCGCTGCTGTTGCTGCTACTACTGCTGCTGGGCGGCGCGAGCGCTCAGTA

CTCCAGCGACCTGTGCAGCTGGAAGGGGAGTGGGCTCACCCGAGAGGCACGCAGCAAGGAGGTGGAGCAG

GTGTACCTGCGCTGCTCCGCAGGCTCTGTGGAGTGGATGTACCCAACTGGGGCGCTCATTGTTAACCTAC

GGCCCAACACCTTCTCACCTGCCCAGAACTTGACTGTGTGCATCAAGCCTTTCAGGGACTCCTCTGGAGC

CAATATTTATTTGGAAAAAACTGGAGAACTAAGACTGTTGGTGCGGGACATCAGAGGTGAGCCTGGCCAA

GTGCAGTGCTTCAGCCTGGAGCAGGGAGGCTTATTTGTGGAGGCGACACCCCAACAGGACATCAGCAGAA

GGACCACAGGCTTCCAGTATGAGCTGATGAGTGGGCAGAGGGGACTGGACCTGCACGTGCTGTCTGCCCC

CTGTCGGCCTTGCAGTGACACTGAGGTCCTCCTTGCCATCTGTACCAGTGACTTTGTTGTCCGAGGCTTC

ATTGAGGACGTCACACATGTACCAGAACAGCAAGTGTCAGTCATCTACCTGCGGGTGAACAGGCTTCACA

GGCAGAAGAGCAGGGTCTTCCAGCCAGCTCCTGAGGACAGTGGCCACTGGCTGGGCCATGTCACAACACT

GCTGCAGTGTGGAGTACGACCAGGGCATGGGGAATTCCTCTTCACTGGACATGTGCACTTTGGGGAGGCA

CAACTTGGATGTGCCCCACGCTTTAGTGACTTTCAAAGGATGTACAGGAAAGCAGAAGAAATGGGCATAA

ACCCCTGTGAAATCAATATGGAGGACCCAGCTTTCTTGTACAAAGTGGTTGATCTAGAGGGCCCGCGGTT

CGAAGGTAAGCCTATCCCTAACCCTCTCCTCGGTCTCGATTCTACGCGTACCGGTTAGTAATGA
```

The adenovirus was produced using the ViraPower™ system (Invitrogen). Thereafter, virus was concentrated using the Vivapure AdenoPACK™ 100 (Sartorius Stedim Biotech) and buffer exchanged to 10 mM Tris-Cl at pH 8.0, 2 mM $MgCl_2$, and 4% w/v sucrose reaching a concentration of $2-4\times10^8$ infection units (ifu)/µl concentration of 9-10 ifu/µl. A LacZ adenovirus was prepared as a control in parallel.

B. Adenovirus Injections

C57/BL6J mice were fed a high fat (60% kcal) diet (D12492, Research Diets) for 20 weeks, starting at 4 weeks of age. Mice were then injected with $1\times10^{10}$ ifu of adenovirus expressing LacZ or Metrnl. Mice were sacrificed five days post-injection and the subcutaneous inguinal fat pad was harvested to analyze for changes in thermogenic and mitochondrial gene expression programs. All gene expression data were normalized to TATA-Binding Protein (TBP) and quantitative measures were obtained using the del-del$C_T$ method.

Example 2: Muscle-Specific PGC-1α4 Transgenic Mice Exhibit a Lean Phenotype, Increased Thermogenesis, and Increased Browning of White Adipose Tissues Peroxisome proliferator-activated receptor gamma coactivator 1-alpha 4 (PGC-1α4), which is an isoform of PGC-1α, is induced by resistance exercise and regulates skeletal muscle hypertrophy (Ruas et al. (2012) Cell 151:1319-1331). Mice transgenically engineered to express PGC-1α4 specifically within muscles under the control of the myogenin promoter have increased skeletal muscle hypertrophy and strength and are additionally resistant to cancer-induced cachexia (Ruas et al. (2012) Cell 151:1319-1331).

It has now been determined herein that such muscle-specific PGC-1α4 transgenic mice exhibit a lean phenotype, increased thermogenesis, and increased browning of white adipose tissues. For example, subcutaneous inguinal fat pads from muscle-specific PGC-1α4 transgenic mice were analyzed for expression of genes related to a thermogenic gene program and genes characteristic of brown fat development. FIG. 1 shows significantly increased levels of well-known gene expression markers of thermogenesis and brown fat cells in the subcutaneous inguinal fat pads of the transgenic mice relative to those of wild type control animals. Thus, muscle-specific expression of PGC-1α4 drives increased thermogenesis and browning of white adipose tissues (e.g., subcutaneous inguinal fat pads), which contributes to an overall lean phenotype in transgenic mice.

Example 3: Metrnl Promotes Thermogenic Gene Programs in Adipose Tissue

A combination of Affymetrix-based gene expression arrays and an algorithm that predicts protein secretion was then used to search for muscle proteins that could mediate the muscle-fat crosslink resulting in the promotion of browning in adipose tissues of the muscle-specific PGC-1α4 transgenic mice. The search identified Meteorin-like (Metrnl) as a candidate.

Figure 2:
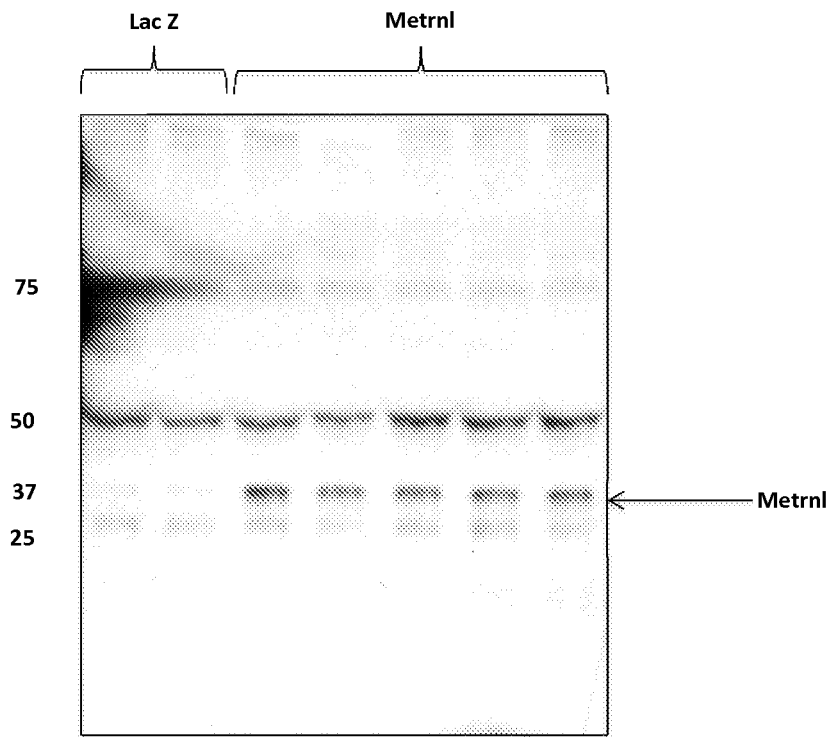
FIG. 2 shows the results of protein and gene expression analyses of plasma and adipose tissue obtained from obese C57/BL6 mice intravenously injected with $1 \times 10^{10}$ LacZ- or Metrnl-expressing adenoviral particles and sacrificed 5 days later (n=5 for each group).
Figure 2:
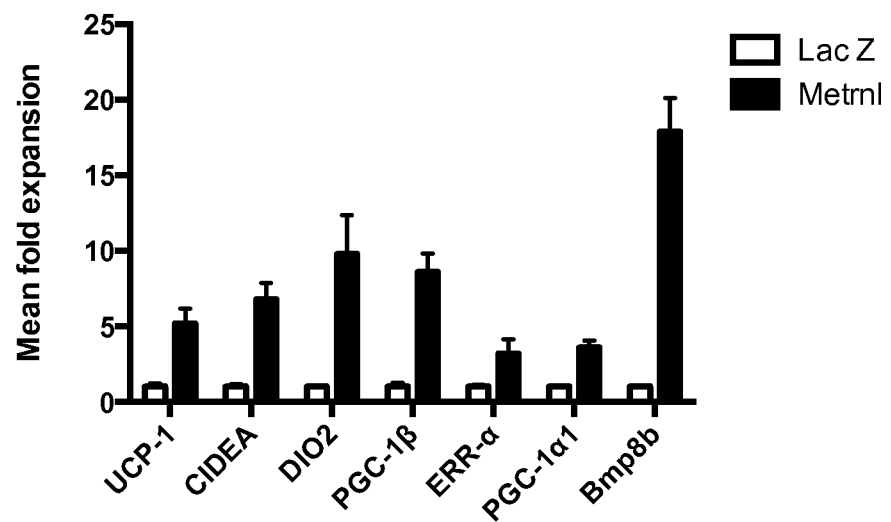

Obese C57/BL6 mice intravenously injected with Metrnl-expressing adenoviral particles exhibited significantly more Metrnl protein expression in plasma relative to control mice injected with LacZ-expressing adenoviral particles (FIG. 2A). An anti-mouse Metrnl polyclonal antibody antigen affinity-purified from sheep was used (Antibody AF6679; R&D Systems). Quantitative polymerase chain reaction (qPCR) results of thermogenesis-related biomarkers in subcutaneous inguinal fat from mice injected with the LacZ- or Metrnl-expressing adenoviral particles demonstrate that Metrnl promotes thermogenic gene programs in adipose tissue (FIG. 2B). Thus, adenoviral-mediated overexpression of Metrnl in mice promotes thermogenic gene programs in adipose tissue.

Example 4: Metrnl Inhibits Inflammation in Skeletal Muscle

Figure 3:
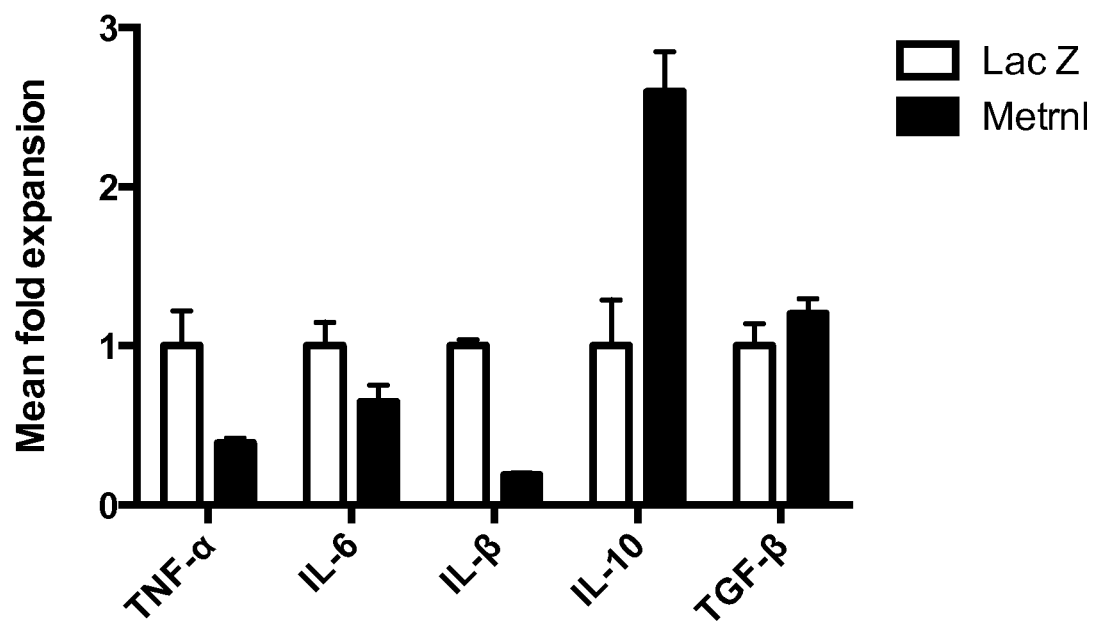
FIG. 3 shows the results of inflammation-related gene expression analyses of skeletal muscle tissue obtained from C57/BL6 mice intravenously injected with $1 \times 10^{10}$ LacZ- or Metrnl-expressing adenoviral particles and sacrificed 5 days later (n=5 for each group). Data shown are representative of two independent experiments and bar graphs are mean+/−standard error of the mean (S.E.M.).

C57/BL6 mice intravenously injected with Metrnl-expressing adenoviral particles also have decreased expression of inflammation-related genes in skeletal muscles (FIG. 3). Thus, adenoviral-mediated overexpression of Metrnl in mice inhibits inflammation in skeletal muscle.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed:

1. A method for increasing thermogenic gene expression in adipose tissue or decreasing expression of at least one inflammation-related gene in skeletal muscle, wherein the inflammation-related gene is selected from the group consisting of tumor necrosis factor alpha (TNF-α), interleukin-6 (IL-6), and interleukin beta (IL-β), in an obese subject in need thereof comprising directly administering to a site of the adipose tissue or the skeletal muscle of the subject an agent, wherein the agent comprises:
   (i) a Metrnl polypeptide having the amino acid sequence of residues 46-311 of SEQ ID NO: 4; or
   (ii) a nucleic acid molecule encoding a Metrnl polypeptide having the amino acid sequences of residues 46-311 of SEQ ID NO: 4, wherein the nucleic acid molecule is operatively linked to a promoter.

2. The method of claim 1, wherein the agent is the Metrnl polypeptide that further comprises a heterologous polypeptide fused thereto.

3. The method of claim 2, wherein the heterologous polypeptide is selected from the group consisting of an Fc domain, a signal peptide, a peptide tag, a dimerization domain, an oligomerization domain, an antibody, and an antibody fragment.

4. The method of claim 3, wherein the heterologous polypeptide is the signal peptide.

5. The method of any one of claims 1-4, wherein
   a) the thermogenic gene is selected from the group consisting of TNF-α, IL-6, IL-P, IL-10, TGF-P, ucp-1, cidea, dio2, pgcip, err-a, pgcla, pgcla isoforms, bmp8b, adiponectin (adipoq), adipsin, otopetrin, type II deiodinase, cig30, ppar gamma 2, elovl3, cAMP, Prdml6, cytochrome C, cox4il, coxIII, cox5b, cox7al, cox8b, glut4, atpase b2, cox II, atp5o, ndufb5, ap2, ndufsl, GRP109A, acylCoA-thioesterase 4, EARA1, claudinl, PEPCK, fgf21, and acylCoA-thioesterase 3; and/or
   b) the subject is a human.

6. The method of claim 1, wherein the agent is the nucleic acid molecule that encodes the Metrnl polypeptide and that further encodes a heterologous polypeptide fused thereto.

7. The method of claim 6, wherein the heterologous polypeptide is selected from the group consisting of an Fc domain, a signal peptide, a peptide tag, a dimerization domain, an oligomerization domain, an antibody, and an antibody fragment.

8. The method of claim 7, wherein the heterologous polypeptide is the signal peptide.

9. The method of any one of claims 6-8, wherein
   a) the thermogenic gene is selected from the group consisting of TNF-α, IL-6, IL-P, IL-10, TGF-P, ucp-1, cidea, dio2, pgcip, err-a, pgcla, pgcla isoforms, bmp8b, adiponectin (adipoq), adipsin, otopetrin, type II deiodinase, cig30, ppar gamma 2, elovl3, cAMP, Prdml6, cytochrome C, cox4il, coxIII, cox5b, cox7al, cox8b, glut4, atpase b2, cox II, atp5o, ndufb5, ap2, ndufsl, GRP109A, acylCoA-thioesterase 4, EARA1, claudinl, PEPCK, fgf21, and acylCoA-thioesterase 3; and/or
   b) the subject is a human.

* * * * *